United States Patent
Uber, III et al.

(10) Patent No.: US 9,629,780 B2
(45) Date of Patent: Apr. 25, 2017

(54) SYSTEM FOR PROCESSING CELLS AND CONTAINER FOR USE THEREWITH

(71) Applicant: MEDRAD, INC., Indianola, PA (US)

(72) Inventors: Arthur E Uber, III, Pittsburgh, PA (US); Mark Trocki, Cheswick, PA (US); Frederick W Trombley, III, Gibsonia, PA (US); Kevin P Cowan, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 983 days.

(21) Appl. No.: 13/845,713

(22) Filed: Mar. 18, 2013

(65) Prior Publication Data

US 2014/0163475 A1 Jun. 12, 2014

Related U.S. Application Data

(62) Division of application No. 12/732,250, filed on Mar. 26, 2010, now Pat. No. 8,414,765, which is a division
(Continued)

(51) Int. Cl.
*A61J 1/00* (2006.01)
*A61J 1/14* (2006.01)
(Continued)

(52) U.S. Cl.
CPC .......... *A61J 1/1443* (2013.01); *A61J 1/1456* (2015.05); *A61J 1/1475* (2013.01); *A61M 5/142* (2013.01);
(Continued)

(58) Field of Classification Search
None
See application file for complete search history.

(56) References Cited

U.S. PATENT DOCUMENTS 2,421,313 A * 5/1947 Brandon .............. B65D 51/002
215/247
2,558,987 A * 7/1951 Shaw .................... A61M 5/165
210/233
(Continued)

FOREIGN PATENT DOCUMENTS

EP 1444003 A1 8/2004
WO 9851369 A1 11/1998
(Continued)

OTHER PUBLICATIONS

Hydromer Coating, Hydromer, Inc. Website (www.hydromer.com/MedicalCoatings.html), as early 1895.
(Continued)

*Primary Examiner* — Terry Cecil
(74) *Attorney, Agent, or Firm* — Joseph L. Kent; David Schramm; James R. Stevenson

(57) ABSTRACT

A container adapted to store and transport an injectate is disclosed. The container includes a divider which extends from an open top end toward a closed bottom end, the divider spaced apart from the closed bottom end to define an opening and separating the container into a first fluid path on a first side of the divider through which fluid can enter the container through the inlet port and a second fluid path on a second side of the divider through which fluid can enter the opening and exit the container through the outlet port. The second fluid path includes at least one filter between the opening and the open top end through which fluid can pass from the first fluid path to the second fluid path but through which at least one component of the injectate cannot pass.

20 Claims, 45 Drawing Sheets

Related U.S. Application Data of application No. 11/460,635, filed on Jul. 28, 2006, now Pat. No. 7,713,232.

(60) Provisional application No. 60/771,206, filed on Feb. 7, 2006, provisional application No. 60/742,224, filed on Dec. 5, 2005, provisional application No. 60/734,035, filed on Nov. 4, 2005.

(51) Int. Cl.

| *B01L 3/00* | (2006.01) |
|---|---|
| *A61M 5/142* | (2006.01) |
| *A61M 5/172* | (2006.01) |
| *A61M 31/00* | (2006.01) |
| *A61M 5/31* | (2006.01) |
| *G06F 19/00* | (2011.01) |

(52) U.S. Cl.
CPC ........ *A61M 5/1723* (2013.01); *A61M 5/3145* (2013.01); *A61M 31/005* (2013.01); *B01L 3/502* (2013.01); *B01L 2300/044* (2013.01); *B01L 2300/0681* (2013.01); *G06F 19/3468* (2013.01)

(56) References Cited

U.S. PATENT DOCUMENTS

| 2,696,818 | A | * | 12/1954 | Van Loghem | A61M 5/1411 210/233 |
| 4,325,368 | A | * | 4/1982 | Kaemmerer | A61J 1/00 215/247 |
| 4,677,980 | A | | 7/1987 | Reilly et al. | |
| 4,803,050 | A | | 2/1989 | Mack | |
| 4,865,993 | A | | 9/1989 | Cassaday | |
| 4,936,829 | A | * | 6/1990 | Zdeb | A61M 5/1409 604/406 |
| 5,219,529 | A | * | 6/1993 | Ngo | B01D 35/303 206/534 |
| 5,383,858 | A | | 1/1995 | Reilly et al. | |
| 5,494,035 | A | | 2/1996 | Leuthold et al. | |
| 5,526,812 | A | | 6/1996 | Dumoulin et al. | |
| 5,618,531 | A | | 4/1997 | Cherksey | |
| 5,690,815 | A | | 11/1997 | Krasnoff et al. | |
| 5,695,653 | A | | 12/1997 | Gsell et al. | |
| 5,720,720 | A | | 2/1998 | Laske et al. | |
| 5,750,103 | A | | 5/1998 | Cherksey | |
| 5,797,870 | A | | 8/1998 | March et al. | |
| 5,808,203 | A | | 9/1998 | Nolan, Jr. et al. | |
| 5,823,993 | A | | 10/1998 | Lemelson | |
| 5,827,216 | A | | 10/1998 | Igo et al. | |
| 5,840,059 | A | | 11/1998 | March et al. | |
| 5,846,225 | A | | 12/1998 | Rosengart et al. | |
| 5,882,343 | A | | 3/1999 | Wilson et al. | |
| 5,997,509 | A | | 12/1999 | Rosengart et al. | |
| 6,060,048 | A | | 5/2000 | Cherksey | |
| 6,122,536 | A | | 9/2000 | Sun et al. | |
| 6,199,554 | B1 | | 3/2001 | Mann et al. | |
| 6,224,566 | B1 | | 5/2001 | Loeb | |
| 6,231,568 | B1 | | 5/2001 | Loeb et al. | |
| 6,319,230 | B1 | | 11/2001 | Palasis et al. | |
| 6,322,536 | B1 | | 11/2001 | Rosengart et al. | |
| 6,344,027 | B1 | | 2/2002 | Goll | |
| 6,387,367 | B1 | | 5/2002 | Davis Sproul et al. | |
| 6,387,369 | B1 | | 5/2002 | Pittenger et al. | |
| 6,416,510 | B1 | | 7/2002 | Altman et al. | |
| 6,464,662 | B1 | | 10/2002 | Raghavan et al. | |
| 6,488,661 | B1 | | 12/2002 | Spohn et al. | |
| 6,520,930 | B2 | | 2/2003 | Critchlow et al. | |
| 6,549,803 | B1 | | 4/2003 | Raghavan et al. | |
| 6,569,127 | B1 | | 5/2003 | Fago et al. | |
| 6,572,579 | B1 | | 6/2003 | Raghavan et al. | |
| 6,585,700 | B1 | | 7/2003 | Trocki et al. | |
| 6,591,129 | B1 | | 7/2003 | Ben Haim et al. | |
| 6,595,979 | B1 | | 7/2003 | Epstein et al. | |
| 6,599,274 | B1 | | 7/2003 | Kucharczyk et al. | |
| 6,602,241 | B2 | | 8/2003 | Makower et al. | |
| 6,605,061 | B2 | | 8/2003 | VanTassel et al. | |
| 6,613,026 | B1 | | 9/2003 | Palasis et al. | |
| 6,652,489 | B2 | | 11/2003 | Trocki et al. | |
| 6,673,033 | B1 | | 1/2004 | Sciulli et al. | |
| 6,749,026 | B2 | | 6/2004 | Smith et al. | |
| 6,749,833 | B2 | | 6/2004 | Raghavan et al. | |
| 6,758,828 | B2 | | 7/2004 | Hammer et al. | |
| 6,796,957 | B2 | | 9/2004 | Carpenter et al. | |
| 6,835,193 | B2 | | 12/2004 | Epstein et al. | |
| 6,855,132 | B2 | | 2/2005 | VanTassel et al. | |
| 6,892,091 | B1 | | 5/2005 | Ben Haim et al. | |
| 6,958,053 | B1 | | 10/2005 | Reilly | |
| 6,958,093 | B2 | | 10/2005 | Vaudo et al. | |
| 7,011,742 | B2 | | 3/2006 | Rosiello | |
| 7,025,876 | B2 | | 4/2006 | Shoji et al. | |
| 7,217,356 | B2 | | 5/2007 | Cork et al. | |
| 7,315,109 | B1 | | 1/2008 | Griffiths et al. | |
| 7,632,245 | B1 | | 12/2009 | Cowan et al. | |
| 7,713,232 | B2 | | 5/2010 | Uber, III et al. | |
| 8,414,765 | B2 | | 4/2013 | Uber et al. | |
| 2002/0010428 | A1 | | 1/2002 | Vedrine et al. | |
| 2002/0082546 | A1 | | 6/2002 | Crank et al. | |
| 2002/0095124 | A1 | | 7/2002 | Palasis et al. | |
| 2003/0028172 | A1 | | 2/2003 | Epstein et al. | |
| 2003/0109849 | A1 | | 6/2003 | Hammer et al. | |
| 2003/0109899 | A1 | | 6/2003 | Fisher et al. | |
| 2003/0219385 | A1 | | 11/2003 | Ahrens | |
| 2003/0225370 | A1 | | 12/2003 | Mueller | |
| 2004/0122366 | A1 | | 6/2004 | Kazemzadeh | |
| 2004/0170597 | A1 | | 9/2004 | Beckman et al. | |
| 2004/0186544 | A1 | | 9/2004 | King | |
| 2004/0191225 | A1 | | 9/2004 | Dinsmore et al. | |
| 2004/0210188 | A1 | | 10/2004 | Glines et al. | |
| 2004/0213756 | A1 | | 10/2004 | Michal et al. | |
| 2004/0228764 | A1 | | 11/2004 | Stephens et al. | |
| 2004/0254525 | A1 | | 12/2004 | Uber et al. | |
| 2005/0070874 | A1 | | 3/2005 | Matsuda et al. | |
| 2005/0075624 | A1 | | 4/2005 | Miesel | |
| 2005/0113744 | A1 | | 5/2005 | Donoghue et al. | |
| 2005/0124975 | A1 | | 6/2005 | Law | |
| 2007/0106208 | A1 | | 5/2007 | Uber, III | |
| 2008/0091147 | A1 | | 4/2008 | Lee | |

FOREIGN PATENT DOCUMENTS

| WO | 9965548 A1 | 12/1999 |
| WO | 0006233 A1 | 2/2000 |
| WO | 0053096 A1 | 9/2000 |
| WO | 0053242 A1 | 9/2000 |
| WO | 0064353 A2 | 11/2000 |
| WO | 0067647 A1 | 11/2000 |
| WO | 0204049 A1 | 1/2002 |
| WO | 02056934 A2 | 7/2002 |
| WO | 02081011 A1 | 10/2002 |
| WO | 02082113 A2 | 10/2002 |
| WO | 03006101 A2 | 1/2003 |
| WO | 03053494 A2 | 7/2003 |
| WO | 03053554 A1 | 7/2003 |
| WO | 03095000 A1 | 11/2003 |
| WO | 2004091688 A1 | 10/2004 |
| WO | 2005072780 A2 | 8/2005 |
| WO | 2005086874 A2 | 9/2005 |
| WO | 2006058280 A2 | 6/2006 |
| WO | 2007053779 A2 | 5/2007 |

OTHER PUBLICATIONS

Visipaque, Amersham Health, a division of GE Healthcare, Website (www.amershamhealth-us.com/visipaque/), as early as 1997.
Aqualon, Hercules, Inc. Website (http://www.sculptra.com/US/Index.jsp), as early as 2002.
PuraMatrix, 3DM Inc. Website, (www.puramatrix.com), as early as 2001.
Burton, A.C., Physiology and Biophysics of the Circulation, 2nd Edition 1972, LC#70-182003, Chapter 5.

(56) References Cited

OTHER PUBLICATIONS

Ensite 3000, Endocardioal Solutions Website (www.endocardioalsolutions.com/patient/index.html) as early as 2000.
CARTO XP System, Biosense Webster/Johnsone & Johnson Website (www.jnjgateway.com), as early as 2000.
Localisa Intracardiac Navigation System, Medtronic Website (www.medtronic.com/epsystems/disclaimer.html), as early as 2000.
Realtime Position Management (RPM) System, Boston Scientific Website (www.bostonscientific.com), as early as 2001.
NAVI-STAR Catheter, Biosense Webster/Johnson & Johnson Website (www.jnjgateway.com), as early as 2000.
Sculptra, Aventis Pharmaceuticals Website (http://www.sculptra.com/US/Inded.jsp) as early as 2002.
Supplementary European Search Report and European Search Report in European Patent Application No. 06836954.5.
International Search Report and Written Opinion and International Preliminary Report on Patentability for International Patent Application No. PCT/US06/43134.
International Search Report and Written Opinion and International Preliminary Report on Patentability for International Patent Application No. PCT/US06/43133.
Aqualon, Hercules, Inc. Website, (http://www.herc.com/aqualon/), as early as 2001.
U.S. Appl. No. 10/916,946, filed Aug. 12, 2004, Griffiths et al.
U.S. Appl. No. 10/921,083, Callen et al., filed Aug. 18, 2004.

\* cited by examiner

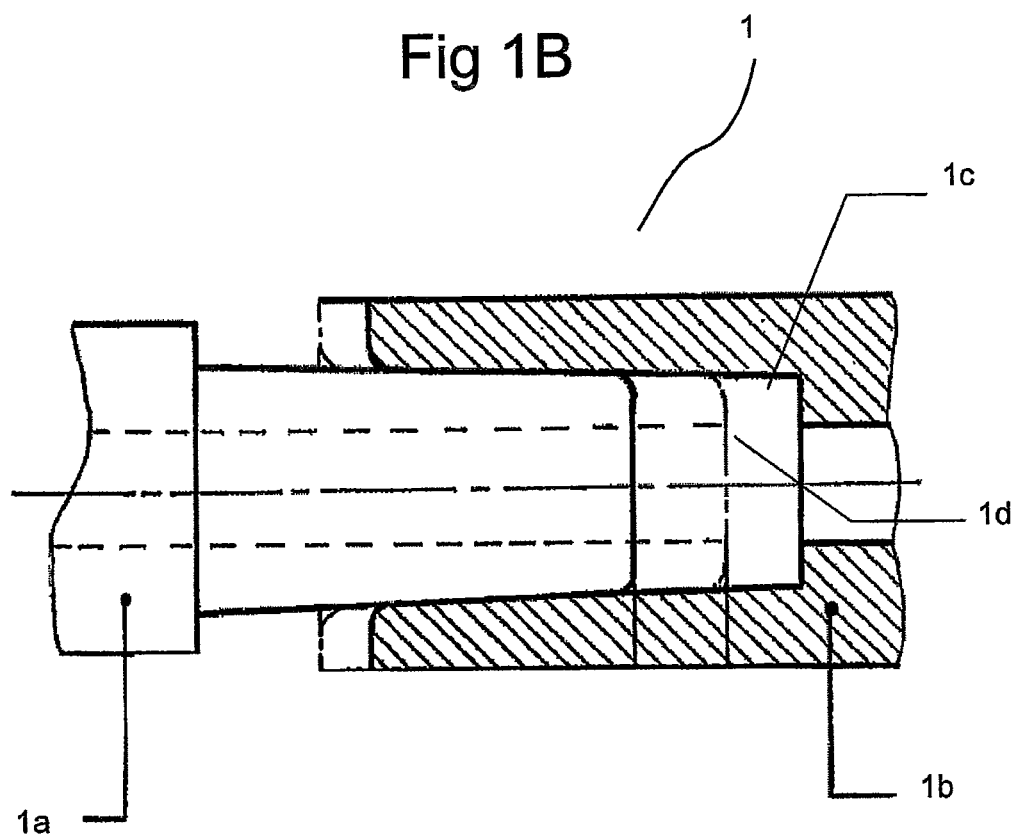

FIG. 5I
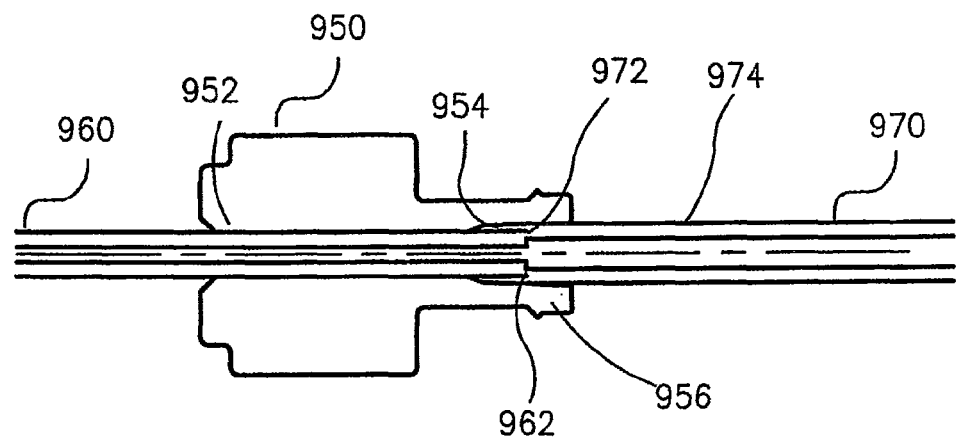
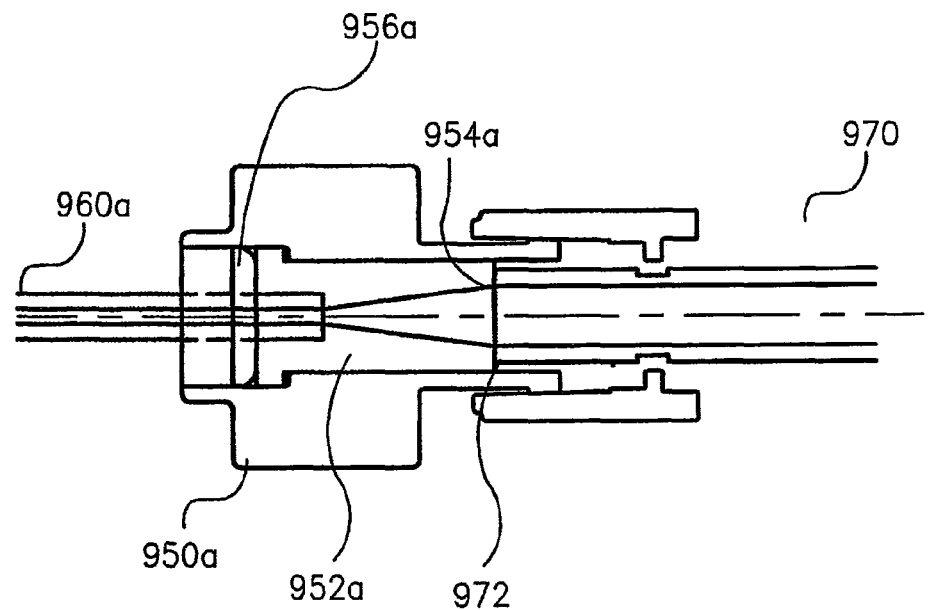
FIG. 5J

FIG.5K
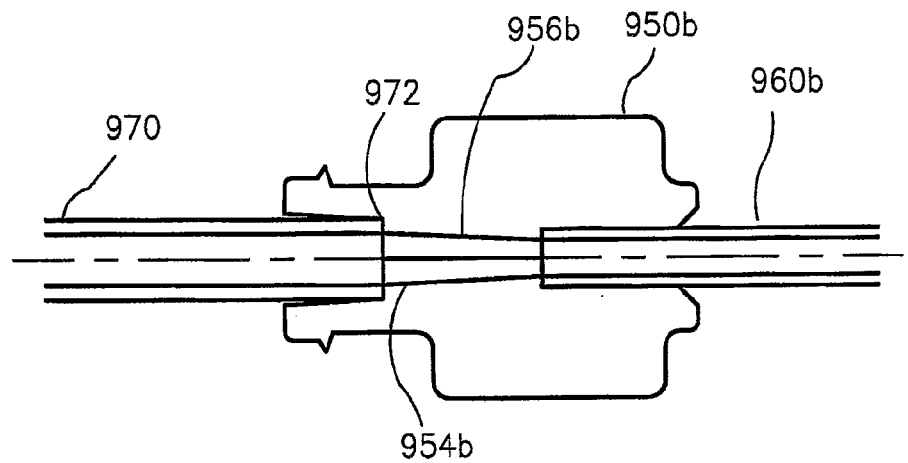
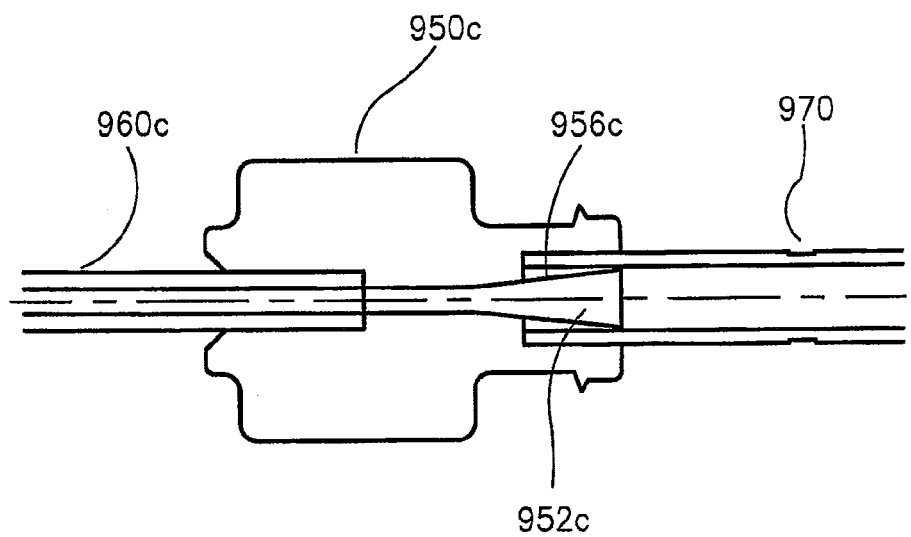
FIG.5L

FIG.6E
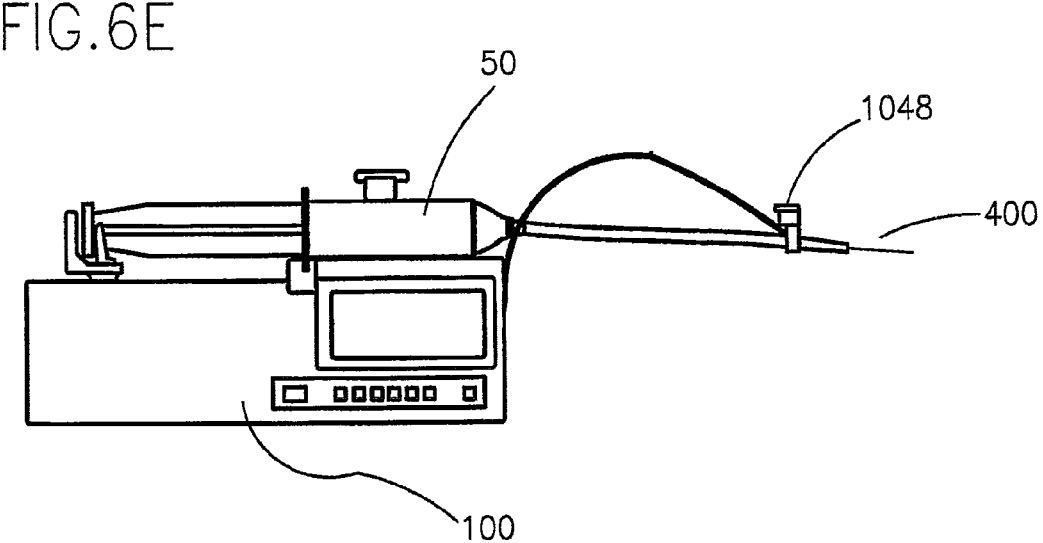
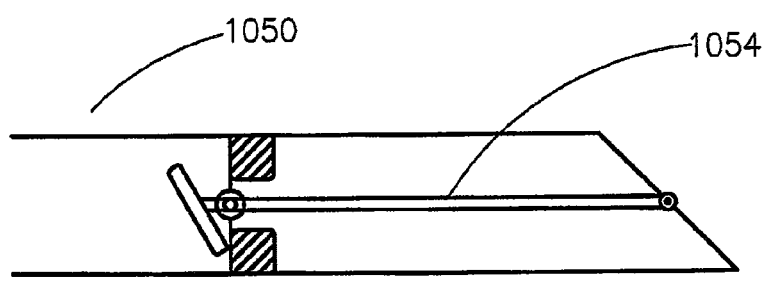
FIG 6F
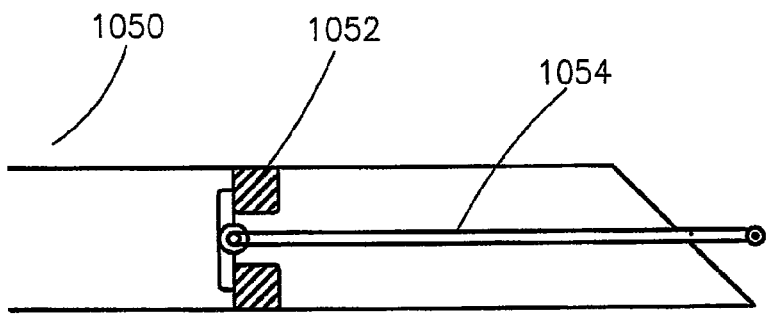
FIG.6G

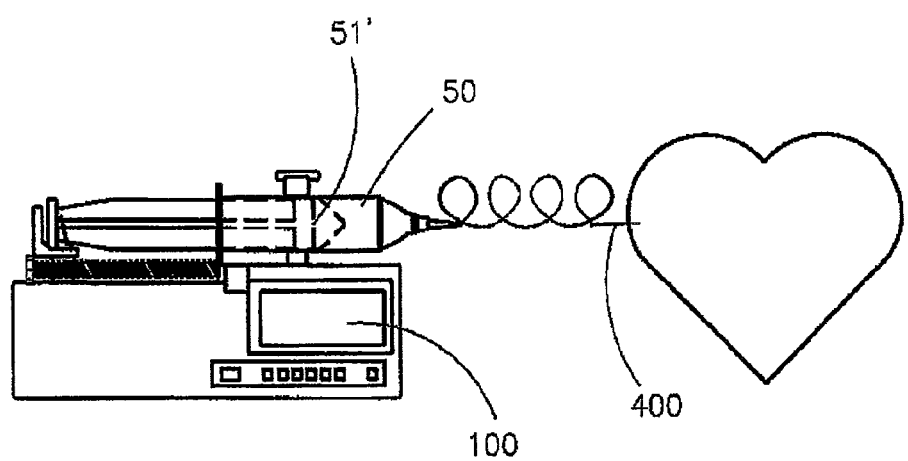
FIG.6O
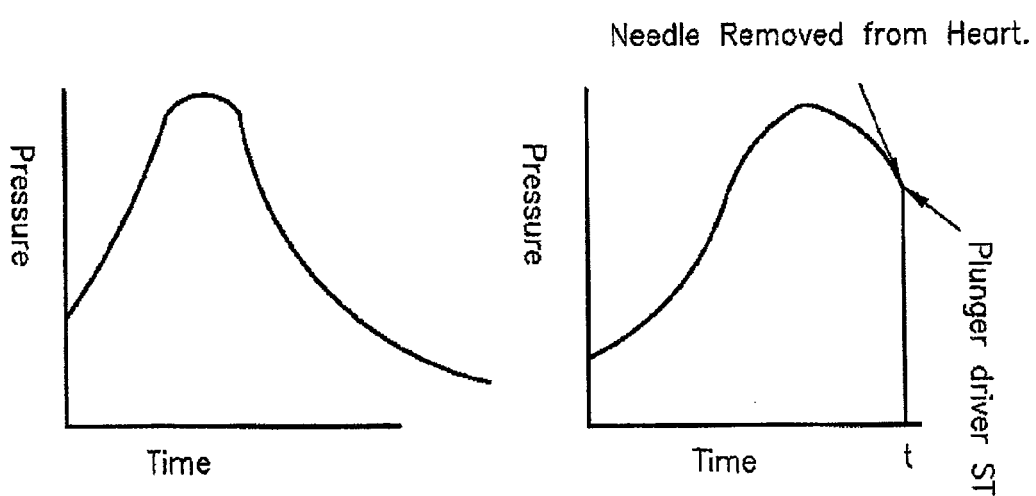
FIG.6P
FIG.6Q

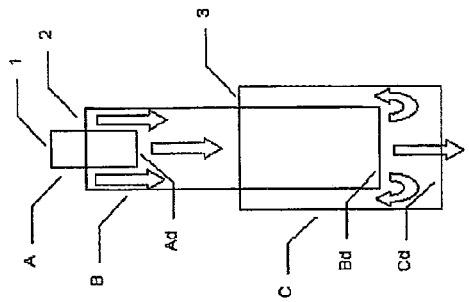
Fig. 7F
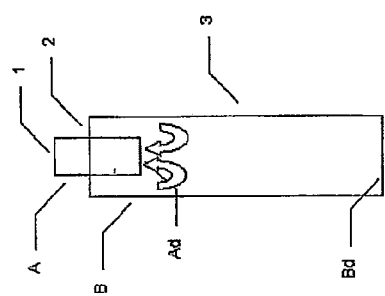
Fig. 7E
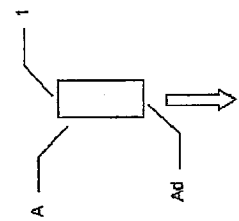
Fig. 7B
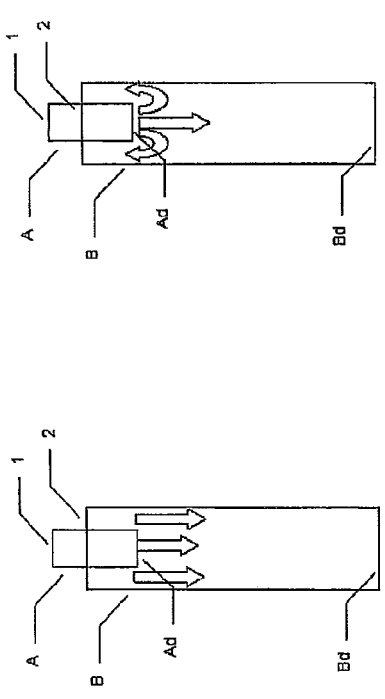
Fig. 7D
Fig. 7C
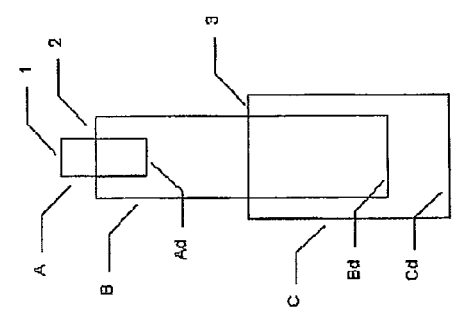
Fig. 7A

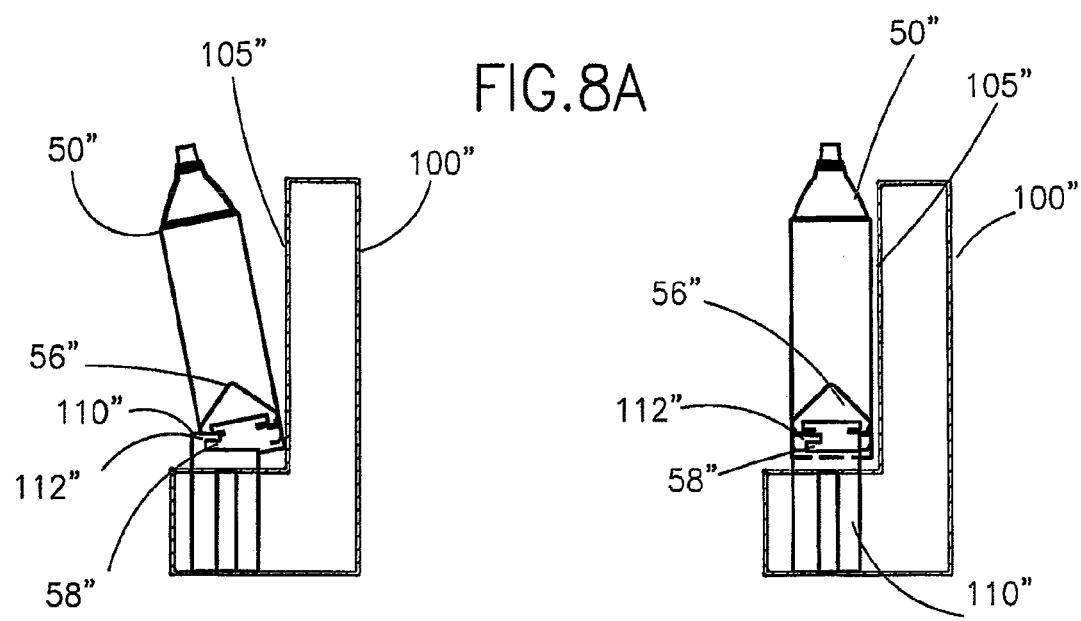
FIG.8A
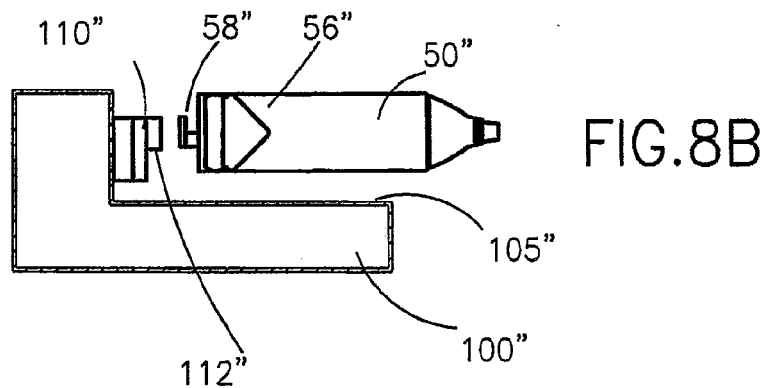
FIG.8B
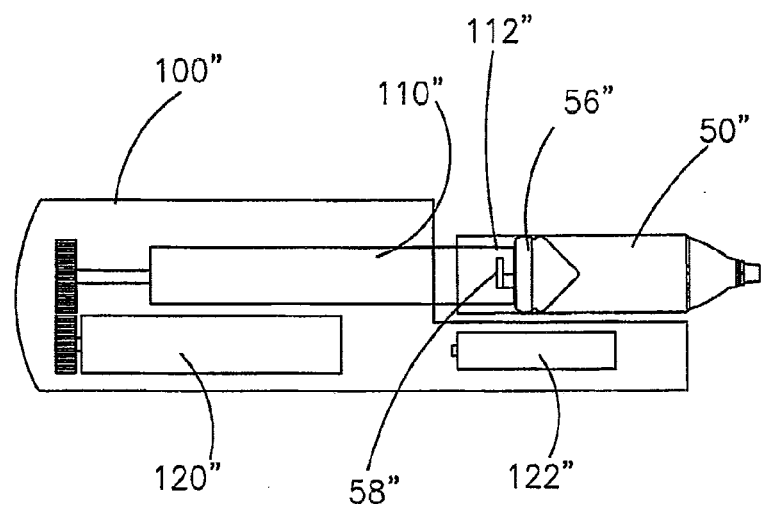

FIG.9D
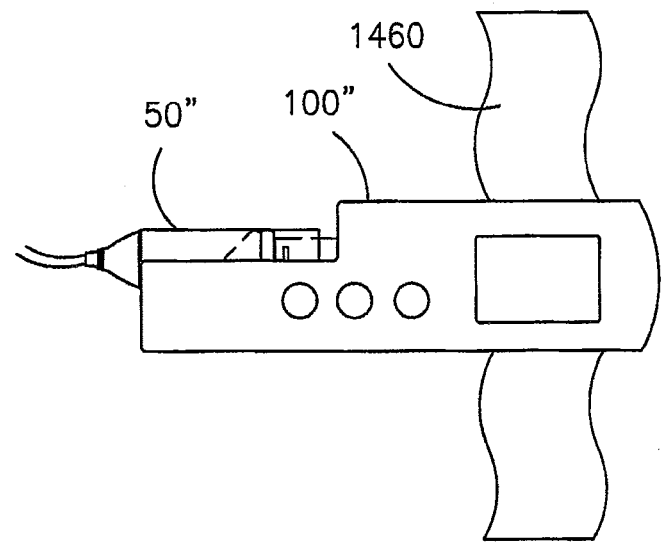
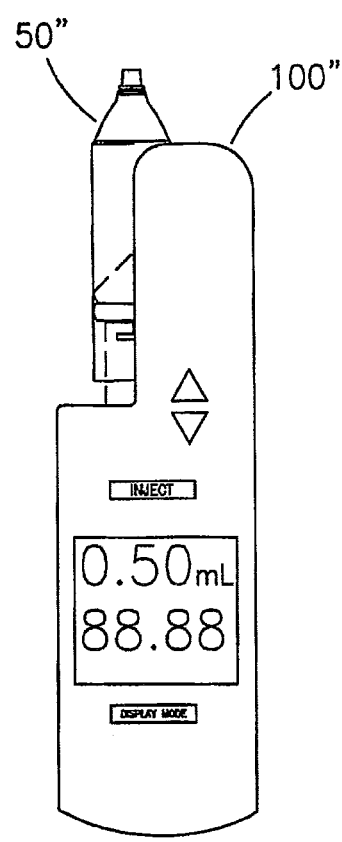
FIG.9E

SYSTEM FOR PROCESSING CELLS AND CONTAINER FOR USE THEREWITH

CROSS-REFERENCE TO RELATED APPLICATION

This application is a divisional of application Ser. No. 12/732,250 filed Mar. 26, 2010, now U.S. Pat. No. 8,414,765, which is a divisional of application Ser. No. 11/460,635, filed Jul. 28, 2006, now U.S. Pat. No. 7,713,232, which claims the benefit of U.S. Provisional Patent Application Ser. No. 60/771,206, filed Feb. 7, 2006, U.S. Provisional Patent Application Ser. No. 60/742,224, filed Dec. 5, 2005, and U.S. Provisional Patent Application Ser. No. 60/734,035, filed Nov. 4, 2005, the disclosures of which are incorporated herein by reference.

BACKGROUND OF THE INVENTION

The present invention relates to the delivery of agents such as therapeutic agents to tissue and, particularly, to the delivery of cells to tissue.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosures of all references cited herein are incorporated by reference.

The treatment of disease by the injection of living cells into a body is expanding rapidly. There are many types of cells being used to treat an equally diverse set of diseases, and both types of cells and disease conditions are expanding rapidly. Xenogeneic cell therapies involve implantation of cells from one species into another. Allogeneic cell therapies involve implantation from one individual of a species into another individual of the same species. Autologous cell therapies involve implantation of cells from one individual into the same individual.

In an example of an allogeneic cell therapy, current phase II clinical trials of SPHERAMINE® by Titan Pharmaceutical of San Francisco, Calif. and Schering AG of Berlin, Germany, retinal pigment epithelial cells are harvested from eyes in eye banks, multiplied many fold in culture medium and placed on 100 micrometer diameter gelatin spheres. The spherical microscopic carriers or microcarriers greatly enhance the cells' survival when injected in the brain. The carriers are injected through needles into the putamen in the brain. The animal precursor work is described in several patents, including U.S. Pat. Nos. 6,060,048, 5,750,103, and 5,618,531, the disclosures of which are incorporated herein by reference. These patents describe many types of cells, carriers, and diseases that can be treated via the disclosed methods. In a rat, about 20 microliters (μl) of injected cells on carriers is sufficient to restore dopamine production to a damaged rat brain. The therapy was injected at the rate of 4 μl/min. This dosage scales to a total injected volume of 0.5 ml in the human brain, although it will have to be distributed over a larger region, probably via multiple individual injections on the order of the 20 μl mentioned above. Cell therapies for the brain and nervous system are discuss further below.

An example of an autologous cell therapy involves the harvesting of mesenchymal stem cell from a patient's bone marrow, concentration of the stem cells, and injection of the cells and other blood components into the heart muscle during open-heart surgery. Further examples include catheter delivered cell therapies, especially to the heart, laparoscopic delivered therapies, and transcutaneous therapies.

In external cell therapy for the heart, volumes of about 0.5 to 1.0 ml are injected into a beating heart. A multi-milliliter syringe is used to hold and deliver the injectate under manual activation. A challenge is presented in that when the heart is contracting, during systole, the tissue becomes relatively hard and tense. In diastole, the tissue relaxes. It is very difficult for a human to time and control a hand injection so that the proper volume is injected all in one period of diastole. In practice, an indeterminate amount of the injectate can squirt or leak out the needle track and is presumably wasted. In addition, it is desirable to uniformly and thoroughly treat the target areas of the heart, and to avoid puncturing the major blood vessels traversing the outside of the heart. These results can also be difficult to achieve with current manual injection practices. With the current state of practice, scar tissue is not injected or treated because it does not respond well, and the growth that does occur can sometimes create dangerous electrical conduction abnormalities.

Cell therapies are generally delivered by hand injection through a needle or catheter. The benefits of hand or manual injection are conceptual simplicity and familiarity for the doctor. However the simplicity is misleading. Many of the parameters of the injection are not and cannot be controlled or even repeated by that doctor, let alone by other doctors. Flow rate is, for example, very difficult to control manually, especially at low flow rates. The stick slip friction of normal syringes exacerbates this problem. Volume accuracy depends upon manual reading of gradations, which is physically difficult while squeezing the syringe and susceptible to human perceptual or mathematical errors. The use of common infusion pumps limits delivery to generally slow and very simple fluid deliveries. Infusion pumps have no ability to provide automatic response or action to the injection based upon any physiological or other measurement or feedback.

Tremendous variations in manually controlled injectate delivery can produce proportionally wide variations in patient outcomes. In clinical trials, this variation is undesirable because it increases the number of patients and thus cost and time needed to establish efficacy. In long term therapeutic use, such variation remains undesirable as some people can receive suboptimal treatment.

FIG. 1A illustrates the current manual state of the art. Cells are taken from a bag or other storage or intermediate container and loaded into a syringe. This procedure involves making and breaking fluid connections in the room air which can compromise sterility, or requires a special biological enclosure to provide class 100 air for handling. The syringe is then connected to a patient interface or applicator, which is commonly a needle, catheter, or tubing that is then connected to a needle or catheter. For many procedures, there is some type of imaging equipment involved in guiding the applicator or effector to the correct part of the body. For example, the imaging equipment can include X-ray fluoroscopy, CT, MR, ultrasound, or an endoscope. The physician views the image and places the applicator by hand. In some neurological procedures, a stereotaxic (or stereotactic) positioner or head frame is used to guide the applicator to the target tissue, deep in the brain, based on coordinates provided by the imaging system. The patient physiological condition is often monitored for safety, especially when the patient is under general anesthesia.

As discussed briefly above, medical research has demonstrated utility of implantation of cells into the brain and central nervous system as treatment for neurodegenerative disorders such as Parkinsons, Alzheimers, stroke, motor neuron dysfunction experienced, for example, by victims of spinal cord injury. As with other cell therapies, the mechanisms of repair are not well understood, but the injection of cells into damaged parenchymal tissue has been shown to recruit the body's natural repair processes and to regenerate new functional tissue as well as the cells themselves living and integrating into the tissue.

As with other cell delivery techniques described above, a long recognized, but unmet need in this field is a set of methods and devices that can provide precise, repeatable and reliable control of dosage of these therapeutic agents in actual clinical settings. Current manual approaches (as summarized above and in connection with FIG. 1A) do not address all of the needs required by new procedures. For example, there are no good methods for ensuring the parameters of cell viability, including spatial distribution, cell quantity, metabolic and electrical activity, in real time during the entire implantation procedure. These variables are affected by cell storage conditions, by the fluid dynamics of an injection (for example, flow, shear stresses or forces, fluid density, viscosity, osmolarity, gas concentration), by the biocompatibility of materials, and by the characteristics of surrounding tissues and fluids.

Deleterious effects of flow of cells through fluid paths are also not well addressed in current techniques. For example, Luer standard connectors are used almost universally in the current medical practice, including in fluid paths for cell delivery. An example of a lure standard connector 1 is show in FIG. 1B. FIG. 1B is taken from the standard ISO 594-1-1986, figure number 2. As the tapered sections of the male 1a and female 1b connectors mate, a dead space is created as indicated by 1c. In addition, the sharp transition in the fluid path at the end of the male luer, as indicated at 1d, can create turbulence and increase shear stress in the fluid and on the cells, resulting in cell damage or even death. Moreover, similar problems exist in commonly used fluid path elements other than connectors.

There are current methods for delivery of chemotherapeutic agents directly to the brain and other central nervous system structures (CNS) including, for example, convection enhanced delivery (CED) and other direct injection by needles, catheters, and syringes into CNS structures. These direct injections are an alternative to less effective intravenous drug delivery methods. Other approaches to drug delivery in the CNS include the placement of drug-impregnated hydrogel wafers (Gliadel®) directly into brain tissue for extended periods of time after tumor excision. In the case of Parkinson's disease treatment, dopamine-producing cells are assembled onto gelatin beads (SPHERAMINE®, Titan Pharmaceuticals), which are hand-injected through precision syringes into the brain. The effectiveness of these methods is typically monitored long after initial treatment with non-invasive imaging (CT, MR).

Examples of systems and methods for convection enhanced delivery to the brain and other solid tissue structures is described in U.S. Pat. No. 5,720,720, the disclosure of which is incorporated herein by reference. Although the '720 patent discloses methods of injecting liquid medications based on a biomechanical model of tissue, it does not address problems unique to the delivery of complex slurries of fragile neural cells. U.S. Pat. No. 6,599,274, the disclosure of which is incorporate herein by reference, discloses methods of cell delivery to the brain using catheter injection systems. Control systems are described in which the distribution and function of therapeutic cells, growth factors, or other proteins are monitored by various techniques of imaging, physical, chemical, and electrical measurement. The '274 patent mentions closed loop, real-time control of the cell infusion process based on imaging and measured properties. However, the '274 patent does not describe how the elements of a controlled cell storage system work together with an injection system to guarantee delivery of viable cells of correct dosage and associated growth factors into tissues of the CNS. U.S. Pat. No. 6,758,828 describes a cell storage system for maintaining the viability of cells injected into tissue, but does not describe an integrated control system for monitoring the viability of cells as they enter the patient and take up residence in the parenchyma, nor does it describe how cell viability can be monitored in vivo.

U.S. Pat. No. 6,749,833 discloses methods to sustain the viability of cells by limiting damage resulting from shear stresses during fluid flow. An apparatus is described which allows for continuous bolus flow or peristaltic flow by reducing these shear forces. It is not clear from the '833 patent how the viability of cells is to be measured after delivery of the cells into living tissue. U.S. Pat. Nos. 6,572,579, 6,549,803 and 6,464,662 attempt to address the problem of distributing a dose of biologically active material into tissue by means of direct catheter injection.

In addition to application of cell therapies to internal tissues such a heart tissue, brain tissue and central nervous system tissue, cell therapies have also recently been applied to skin. Dermatologists have been injecting drugs into the skin for years. Recently, injections of collagen, which can be thought of as a cell-less tissue, have become popular. Moreover, Intercytex of Cambridge UK has developed the ability to inject autologous dermal papilla cells for the growth of hair to treat baldness. The cells are harvested from a person, multiplied in culture, and then reimplanted into the same person. The implantation requires about 1000 injections of 1 microliter each.

Various aspect of delivery of agent to tissue and related aspects are also discussed in U.S. Pat. Nos. 5,720,720, 5,797,870, 5,827,216, 5,846,225, 5,997,509, 6,224,566, 6,231,568, 6,319,230, 6,322,536, 6,387,369, 6,416,510, 6,464,662, 6,549,803, 6,572,579, 6,599,274, 6,591,129, 6,595,979, 6,602,241, 6,605,061, 6,613,026, 6,749,833, 6,758,828, 6,796,957, 6,835,193, 6,855,132, Patent Applications Nos. 2002/0010428, 2002/0082546, 2002/0095124, 2003/0028172, 2003/0109849, 2003/0109899, 2003/0225370, 2004/0191225, 2004/0210188, 2004/0213756, and 2005/0124975, as well as in, PCT Published International Patent Application WO2000/067647, EP1444003, the disclosures of which are incorporated herein by reference.

Although various devices, systems and methods have been developed for delivery of agents, including therapeutic agent, to various types of tissue, it remains desirable to develop improved devices, systems and methods for delivering agents to tissue and, particularly, for delivering therapeutic cells to tissue.

The present invention, along with the attributes and attendant advantages thereof, will best be appreciated and understood in view of the following detailed description taken in conjunction with the accompanying drawings.

SUMMARY OF THE INVENTION

In one aspect, the present invention provides a system for injecting an injectate into patient, including: a first pressurizable container for holding the injectate; a patient interface in fluid connection with the first pressurizable container, the patient interface being adapted to pass the injectate into tissue of the patient; a powered injector in operative connection with the first pressurizable container to pressurize the injectate; a controller system in operative connection with powered injector; and a stereotactic localization frame adapted to be placed in operative connection with the patient interface to assist in controlling localization of the patient interface.

The system can further include a communication system in connection with the controller system. The communication can, for example, provide information to the controller system of at least one measured parameter. The controller system is preferably adapted to transmit a control signal based at least in part on the measure parameter to control the powered injector. The system can also include at least one monitoring system adapted to measure at least one physiological property of the patient. The communication system can be in connection with the monitoring system to provide information of the measured value of the at least one physiological property to the controller system. The controller system can, for example, be adapted to transmit a control signal based at least in part on the measured value of the least one physiological property.

The system can also include an imaging system adapted to image a region of the patient to which the injectate is delivered. The communication system can, for example, be in connection with the imaging system to provide information of a measured property from the imaging system to the controller. In this embodiment, the controller can be adapted to transmit a control signal based at least in part on the measured property from the imaging system.

The system can also include at least one sensor to measure at least one property of the injectate. The sensor being can be connection with the communication system to provide information of the measured injection fluid property to the controller. The at least one property of the injectate can, for example, provides a measurement of shear forces on the injectate. The at least one property of the injectate can, for example, beat least one of flow rate or pressure.

In several embodiments, the first pressurizable container is a first syringe having a first plunger slidably disposed therein to pressurize the injectate. The injector is adapted to effect movement of the first plunger.

The powered injector can, for example, be in operative connection with a second pressurizable container. The second pressurizable container can be in fluid connection with the first pressurizable container such that pressurized fluid from the second pressurizable container is operable to pressurize the injectate within the first pressurizable container. In several embodiments, the first pressurizable container is a first syringe having a first plunger slidably disposed therein to pressurize the injectate, and pressurized fluid from second pressurizable container is operable to effect movement of the first plunger. The second pressurizable container can be a second syringe having a second plunger slidably disposed therein.

The system can also include a sterile containment system adapted to encompass at least a portion of the first pressurizable container and a portion of the powered injector.

In another aspect, the present invention provides a container adapted to store and transport an injectate. The container is adapted to have a fluid introduced therein and effluent removed therefrom to effect processing of the injectate. The container can, for example, be adapted to be subjected to freezing and thawing.

The container can include a first port at a first axial position within the container and at least a second port at a second axial position within the container, wherein the first axial position and the second axial position are different. The first port and the second port can, for example, be formed monolithically with the container. The first port can also be on a distal end of a first tube extending through an end closure of the container, and the second port can be on the distal end of a second tube extending through the end closure the container. In one embodiment, the end closure is a septum, the first tube is a first piercing member and the second tube is a second piercing member. The container can, for example, encompass viable cells within a first fluid. At least one of the first axial position and the second axial position can be above an axial position of cells settled to a bottom of the container. The cells can, for example, be retinal pigment epithelial cells supported on microspheres, mesenchymal stem cells, multipotent adult progenitor cells, embryonic stem cells, cardiac precursor cells, cardiac cells, beta-islet precursor cells, beta-islet cells, neural precursor cells, or neural cells.

In another embodiment, the container includes a divider within the container to create a first fluid path on a first side of the divider via which fluid can enter the container and a second fluid path on a second side of the divider via which fluid can exit the container. The second side fluid path includes at least one filter through which fluid can pass but through which at least one component of the injectate cannot pass. As discussed above, the container can encompasses viable cells within a first fluid. The filter preferably prevents cells from passing therethrough. Once again, the cells can, for example, be retinal pigment epithelial cells supported on microspheres, mesenchymal stem cells, multipotent adult progenitor cells, embryonic stem cells, cardiac precursor cells, cardiac cells, beta-islet precursor cells, beta-islet cells, neural precursor cells, or neural cells.

In a further aspect, the present invention provides a method of processing cells prior to delivery thereof including the step of contacting the cells with at least one fluid to decrease the concentration of a hibernation solution in which the cells are transported wherein the occurrences of exposure of the cells to non-sterile air is minimized and the duration of any occurrence of exposure to non-sterile air is minimized. The cells can be transported in container adapted to store and transport the cells. The container is preferably adapted to have the at least one fluid introduced therein and effluent removed therefrom. The at least one fluid can include a buffer solution. A closed system can, for example, be used in the processing. The closed system can, for example, include a source of the first fluid adapted to be placed in fluid connection the container. As discussed above, the container can include a first port for introduction of the at least one fluid and a second port for removal of effluent.

The closed system can include a pump system to effect flow of the at least on fluid into the container and effluent out of the container. The closed system can further include a first one-way valve in fluid connection with the first port and a second one-way valve in fluid connection with the second port.

The container can further include a third port adapted to provide air into the container and a sterile filter in fluid connection with the third port so that air can move in and out as fluid level changes in the container while maintaining sterility.

In several embodiments, the first port has a first tube extending therethrough to a first length within the container and the second port has a second tube extending therethrough to a second length within the container. The first length is greater than the second length, such that when the container is in a generally upright position and cells are settled to the bottom thereof, the end of the first tube is within the cells and the end of the second tube is above the level of the cells.

In another aspect, the present invention provides a system for use in the processing of cells encompassed in a container. The system includes at least a first fluid path adapted to introduce at least one fluid into the container and at least a second fluid path adapted to remove effluent from the container. The system can further include a pump system to effect flow of the fluid into the container and flow of effluent from the container. The system can also include a valve system to control at least flow of the fluid into the container and flow of effluent from the container. The valve system can include at least a first one way valve in fluid connection with the first fluid path and at least a second one way valve in fluid connection with the second fluid path.

The system can also include a controller in operative connection with at least one of the pump system or the valve system. The controller can, for example, include a computer processor (for example, a microprocessor or a PC).

The system can further include a third fluid path adapted to be placed in fluid connection with the container and be placed in connection with a fluid delivery system in which the cells can be loaded for delivery to a patient. The system can also include at least a fourth fluid path adapted to be placed in fluid connection with the container to remove a sample from the container for analysis. Likewise, the system can also include at least a fifth fluid path adapted to introduce air into the container. A filter can be placed in fluid connection with the fifth fluid path to assist in maintaining sterility.

The system can further include a source of the fluid in fluid connection with the first fluid path.

In another aspect, the present invention provides a system for processing cells (and/or other injectate components) comprising a container and a plunger adapted to be slidably positioned within the container. The system includes at least one inlet port through which a fluid can enter the system and at least one effluent port through which an effluent can exit the system. The plunger section forms a sealing engagement with the inner wall of the container such that rearward motion of the plunger is adapted to draw fluid into the system via the inlet and forward motion of the plunger is adapted to force effluent out of the system via the effluent port.

The effluent port can also be adapted to effect delivery of cells therethrough to a patient. The system can also include an outlet port adapted to effect delivery of cells therethrough to a patient. A filter can be placed in fluid connection with the effluent port to prevent cells from exiting via the effluent port in such an embodiment.

The system can further include a first check valve in fluid connection with the inlet port and a second check valve in fluid connection with the effluent port.

The plunger can include a filter disposed therein that allows fluid to pass therethrough but prevents cells from passing therethrough. The filter can, for example, separate the cells from the effluent port. The filter can also separate the cells from the inlet port.

In embodiments including an outlet as described above, the outlet port can adapted to be closed during processing of the cells during which fluid enters the system via the inlet port and effluent exits the system via the effluent port. Moreover, the effluent port can be adapted to be closed when the outlet port is opened to deliver cells therethrough.

The inlet port can, for example, be in fluid connection with a passage through the plunger so that the fluid can enter the plunger and pass through the filter. The effluent port can likewise be in fluid connection with a passage through the plunger so that the effluent can pass through the filter and exit the effluentport. The plunger includes a sealing member adapted to form a sealing engagement with an interior wall of the container.

In still a further aspect, the present invention provides a plunger for use in connection with a container encompassing cells (and/or other injectate component(s)) to effect processing of the cells (and/or other injectate component(s)). The plunger includes a filter through which fluid can pass but cells cannot pass and a sealing member adapted to form a sealing engagement with an interior wall of the container. The plunger can also include an inlet port to introduce fluid into the plunger to pass through the filter to enter the container and an effluent port through which effluent can flow through the filter to exit the container. The plunger can further include a one way valve in fluid connection with the inlet port. The plunger can likewise include a one way valve in fluid connection with the effluent port.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 1B illustrates an embodiment of a standard luer connector.

FIG. 5I illustrates a luer-type fitting or connector of the present invention that provides for relatively smooth transitions and low fluid loss.

FIG. 5J illustrates another luer-type fitting or connector of the present invention that provides for relatively smooth transitions and low fluid loss.

FIG. 5K illustrates another luer-type fitting or connector of the present invention that provides for relatively smooth transitions and low fluid loss.

FIG. 5L illustrates another luer-type fitting or connector of the present invention that provides for relatively smooth transitions and low fluid loss.

FIG. 6E illustrates a delivery system of the present invention including a normally closed, a push-button valve to activate a pump system or injector system and open fluid passage to a needle.

FIG. 6F illustrates the use of a one-way check valve in a needle of the present invention in which the needle is placed in tissue.

FIG. 6G illustrates the use needle of FIG. 6F in which the needle outside of the tissue.

FIG. 6O illustrates an embodiment of an injector or delivery system of the present invention.

FIG. 6P illustrates a pressure profile of the system of FIG. 6O with system capacitance wherein the patient interface is positioned within tissue.

FIG. 6Q illustrates a pressure profile of the system of FIG. 6O with system capacitance wherein the patient interface is removed from tissue.

FIG. 7A illustrates a schematic diagram of three fluid paths in operative connection as concentric cylinders.

FIG. 7B illustrates a simple fluid path including one fluid path element and one fluid path.

FIG. 7C illustrates a fluid path including two fluid path elements.

FIG. 7D illustrates another fluid path including two fluid path elements.

FIG. 7E illustrates a fluid path in which injectate is pulled back a first fluid path while a purging or physiological solution is injected at the same flow rate down a second fluid path.

FIG. 7F illustrates the fluid path elements of FIG. 7A, with an exemplary fluid flow indicated.

FIG. 8A illustrates an embodiment of an injection system of the present invention in which a disposable container or syringe can be snapped securely and reliably into place with an injector in a simple, two-step operation.

FIG. 8B illustrates a cutaway view of the injector system of FIG. 8A showing the motor and battery power supply.

FIG. 9D illustrates the injector system of FIG. 8A adapted to be worn on the body of an operator.

FIG. 9E illustrates the injector system of FIG. 8A including embodiment of control and display panels.

DETAILED DESCRIPTION OF THE INVENTION

Figure 2:
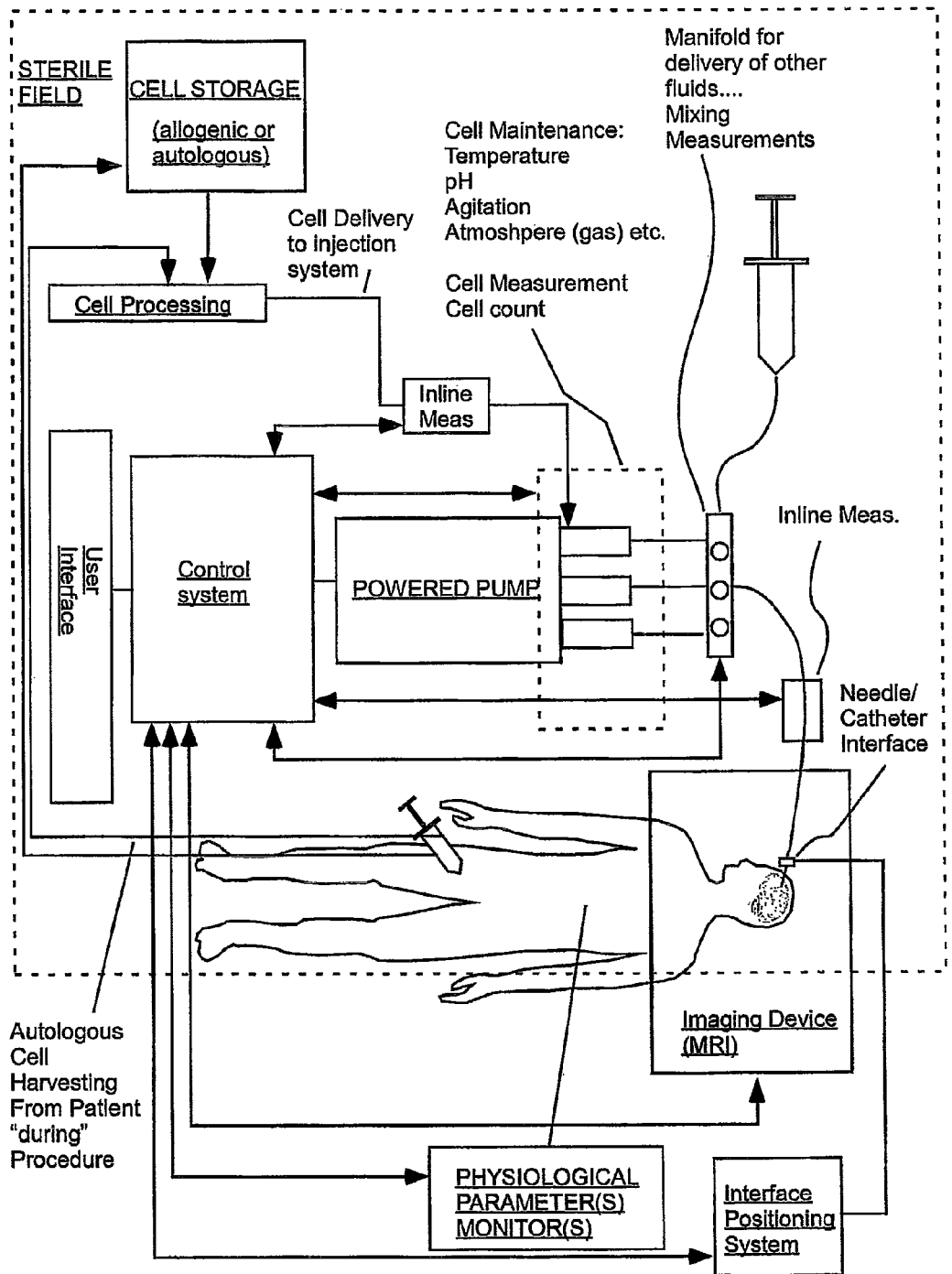
FIG. 2 sets forth several embodiments of systems of the present invention for use in delivery of an injectate or injection fluid, and particularly an injection fluid containing cells, to a brain of a patient FIG. 3 sets forth several other embodiments of systems of the present invention for delivery of an injection fluid, and particularly cells, to the heart of a patient.
Figure 3:
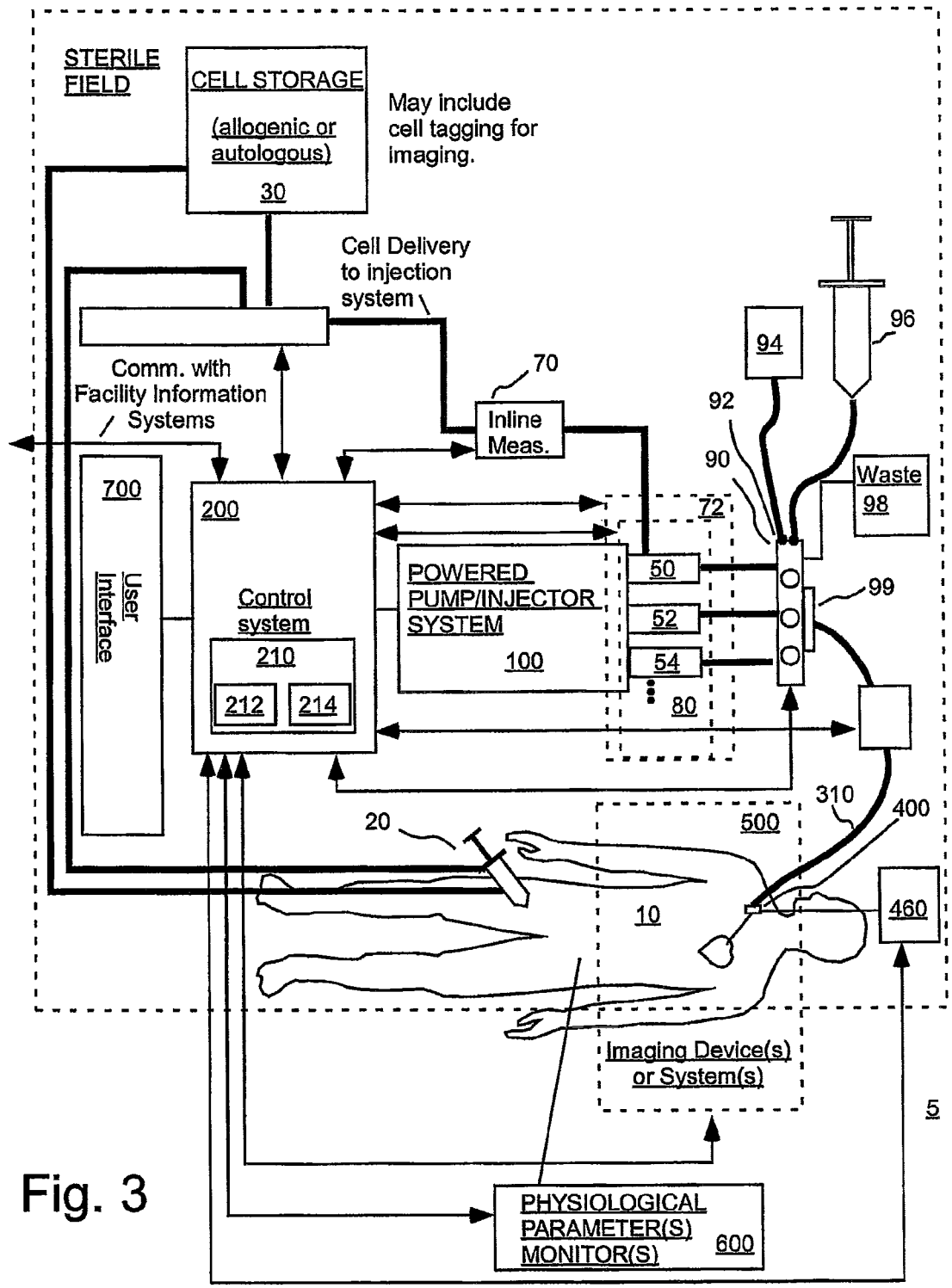

FIG. 2 sets forth several embodiments of systems of the present invention for use in delivery of an injectate or injection fluid, and particularly an injection fluid containing cells, to a brain of a patient. FIG. 3 sets forth several embodiments of systems of the present invention for delivery of an injection fluid, and particularly cells, to the heart of a patient. Several embodiments of the present invention are discussed below in detail with respect to delivery of cells to the brain or external heart of a patient. However, one skilled in the art appreciates that the devices, systems and methods of the present invention can be used to deliver many different types of substances to many different tissues, internal to the body as well as to the skin. Moreover, the devices, systems and methods of the present invention are applicable to open surgery or endoscopic needle-based deliveries as well as to catheter-based deliveries.

The systems of FIGS. 2 and 3 are similar in overall architecture and operation, and the systems of the present invention will be described generally with reference to FIG. 3 and with respect to the delivery of cells through the outer surface to the tissue of the heart.

In general, cell therapies are believed to work by replacing diseased or dysfunctional cells with healthy, functioning ones. However, the mechanisms of the therapies are not well understood. As described above, therapeutic treatment involves harvesting cells from the body (such as adult stem cells) and later implants such cells. As discussed above, the techniques are being applied to a wide range of human diseases, including many types of cancer, neurological diseases such as Parkinson's and Lou Gehrig's disease, spinal cord injuries, and heart disease. Many factors are considered when selecting an autologous or an allogeneic stem cell transplant. In general, autologous stem cell transplants (since the donor and the recipient are the same person and no immunological differences exist) are safer and simpler than allogeneic (donor cells from a healthy donor other than the recipient) stem cell transplant. However, allogenic cells can be better characterized and controlled.

FIG. 3 illustrates, for example, the harvesting of autologous bone marrow cells or other cells from a patient 10 using a harvesting device such as syringe 20 before or during an injection procedure. The harvesting of bone marrow cells from the thigh of a patient is discussed, for example, in U.S. Pat. Nos. 6,595,979 and 6,835,193, the disclosures of which are incorporated herein by reference. Such autologous cells or allogenic cells from a donor can be placed in a cell storage container or facility 30 for use at a later time, which may for example, include incubation, concentration and freezing of the cells and/or other processing. Shortly before delivery to a patient, cells can be removed from cell storage 30 for processing in a cell processing unit 40 and/or other units before delivery (for example, thawing and other processing). Autologous cells can also be harvested and relatively quickly delivered to a patient with or without substantial intervening processing.

In several embodiments of the present invention, cells are delivered to a container 50 (for example, a syringe) in a carrier fluid as known in the art. Cells can also be harvested directly into container 50 from the patient. The contents of container 50 are preferably pressurizable for injection into the tissue of a patient. Prior to delivery of the cell-containing fluid to container 50, measurements relative to effective delivery of cells to heart or other tissue can be made using one or more inline measuring units or systems 70. Measuring unit 70 can, for example, measure cell count, cell viability, injection fluid density, temperature, nutrient level, gas level, composition etc. In FIG. 3, container 50 is illustrated as being connected to a powered pump/injector system 100 which is operable, for example, to pressurize the contents of container 50 for injection into the tissue of the patient. Using, for example, connection mechanisms known in the art, container 50 (for example, a syringe) can be removably connectable to powered pump/injector system 100. Harvesting device 20 can, for example, harvest cells directly into container 50 as described above, and any subsequent storage and/or processing of cells can take place in container 50.

Measuring unit 70 and or other measuring unit(s) or system(s) 72 can remain in operative connection with container 50 while container 50 is operatively connected to pump/injector system 100 to continue to monitor the state of the injection fluid prior to and during injection. Moreover, one or more maintenance units or systems 80 can be placed in operative connection with container 50 while container 50 is in operative connection with pump/injector system 100 to maintain cells in a desirable state. For example, the injection fluid in container 50 can be agitated to maintain the injection fluid in a generally homogeneous state. The agitation of a multi-component fluid is discussed in Published PCT International Patent Application Nos. WO 00/53096, WO 00/53242, WO 00/64353, WO 03/053494, WO 03/053554 and WO 03/095000, the disclosures of which are incorporated herein by reference. Moreover, the viability of cells can be maintained by maintenance unit 80. For example, temperature, pH, pressure, nutrients, gases etc can be maintained within desirable ranges and waste can be removed. Various aspects of cell maintenance are discussed, for example, in U.S. Pat. No. 6,758,828, the disclosure of which is incorporated herein by reference.

Each of the various systems or units of the present invention can, for example, be in unidirectional or bidirectional communication with a control system 200 that can, for example, include one or more control units or controllers including one or more processors or microprocessors 200, which (as known in the control arts) can include one or more processing units 212 and associated memory storage units 214. Control system 200 can be centralize or distributed within system 5. As illustrated in FIG. 3, feedback or closed loop communication paths can, for example, be used to control the various components of system 5 before, during and after an injection procedure to control the various components of system 5. Moreover, communication between facility (for example, hospital) information systems and system 5 can be provided via, for example, control system 200.

As also illustrated in FIG. 3, more than one container (for example, syringe) can be placed in operative connection with pump/injector system 100 to inject more than one fluid in the tissue of patient 10. In FIG. 3, three containers 50, 52 and 54 are illustrated, but less than or more than three containers and associated fluids (which may contain liquid, solid and/or gaseous components) can be provided. Many type of additional fluids including, but not limited to, flushing or diluents fluids such as saline, viscosity adjusting fluids, imaging contrast fluids, and/or nutrient fluids, can be provided. The flow of fluid from various pressurizable containers can, for example, be controlled via a manifold system 90 in fluid connection with containers 50, 52 and 54 and in communicative connection with control system 200. One or more ports 92 can be provided, for example, in manifold system 90 to provide for fluid connection to other fluid sources which can include one or more other powered pump/injector systems 94 and/or one or more manually operated syringes 96. Manifold system 90 can also include one or more ports through which waste (which may present a biohazard) can be transmitted to an appropriate waste container 98. Manifold system 90 can further include or be in fluid communication with one or more mixers or mixing systems 99 to, for example, effect mixing of one or more fluids.

Injection fluid is delivered from manifold system 90 (or directly from container 50 and other containers in case of a system in which manifold system 90 is absent) through one or more fluid path elements 310 (for example, flexible tubing), each of which can include one or more lumens, to a patient interface 400 (for example, a needle or a catheter) for injection into the patient's tissue. One or more measurement units or systems 74 can be provided in connection with fluid path element 310 or in connection with patient interface 400 for measurement of various variables including fluid flow rate, fluid pressure, fluid density, cell count, cell viability, cell maintenance variables etc. Such information can, for example, be transmitted to controls system 200 and the operation of system components including, for example, pump system 100, cell maintenance unit or system 80, manifold 90 and patient interface 400 can be controlled, at least in part, on the basis of such data or information. System 5 can further include a patient interface positioning control system 460 which can operate to facilitate manual positioning or to partially or fully automate the positioning of patient interface 400.

Various other components or systems can be used in connection with the present invention. For example, one or more imaging devices or system(s) 500 (for example, X-ray systems (including, for example, angiography, venography and urography), computed tomography (CT) systems, magnetic resonance imaging (MRI) systems, ultrasonic imaging systems, light based imaging systems, and positron emission tomography (PET) systems) can be used in connection with the present invention. Imaging systems 500 can, for example, be used to track the position and viability of previously tagged cells which are tagged with a marker that is detectible using imaging system 500, to track the position of patient interface 400 or to monitor one or more patient organs. Likewise, one or more physiological parameter monitors or monitoring systems 600 can be provided to monitor patient physiological parameters including, but not limited to, cardiac function, respiration, blood oxygen level, and blood pressure. Data from monitor(s) 600 can be provided to control system 200 and can be used in controlling the operation of one or more of the components of system 5. Monitor(s) 600 can also be used to simply monitor the state of patient 10 and ensure that the injection procedure does not harm patient 10.

System 5 can also include a user interface system 700 that can, for example, be used to provide user input and/or control into system 5 as well as to provide information (for example, using visual, audible and/or tactile indicators) to the user(s).

Details of various embodiments of a number of the components of and the operative connection of such components within system 5 are set forth below. One skilled in the art appreciates that the various components of the systems of the present invention can be arranged or operatively connected in various manners and that various systems of the present invention need not include all of the components set forth in FIG. 2 and/or FIG. 3.

Although headings and subheading are provided in the text of the application for organizational purposes, one skilled in the art will appreciate that concepts discussed under one heading or subheading can have applicability in other headings or subheadings and the use of headings and subheading is not meant to limit the invention in any manner.

Patient Interface

Figure 4:
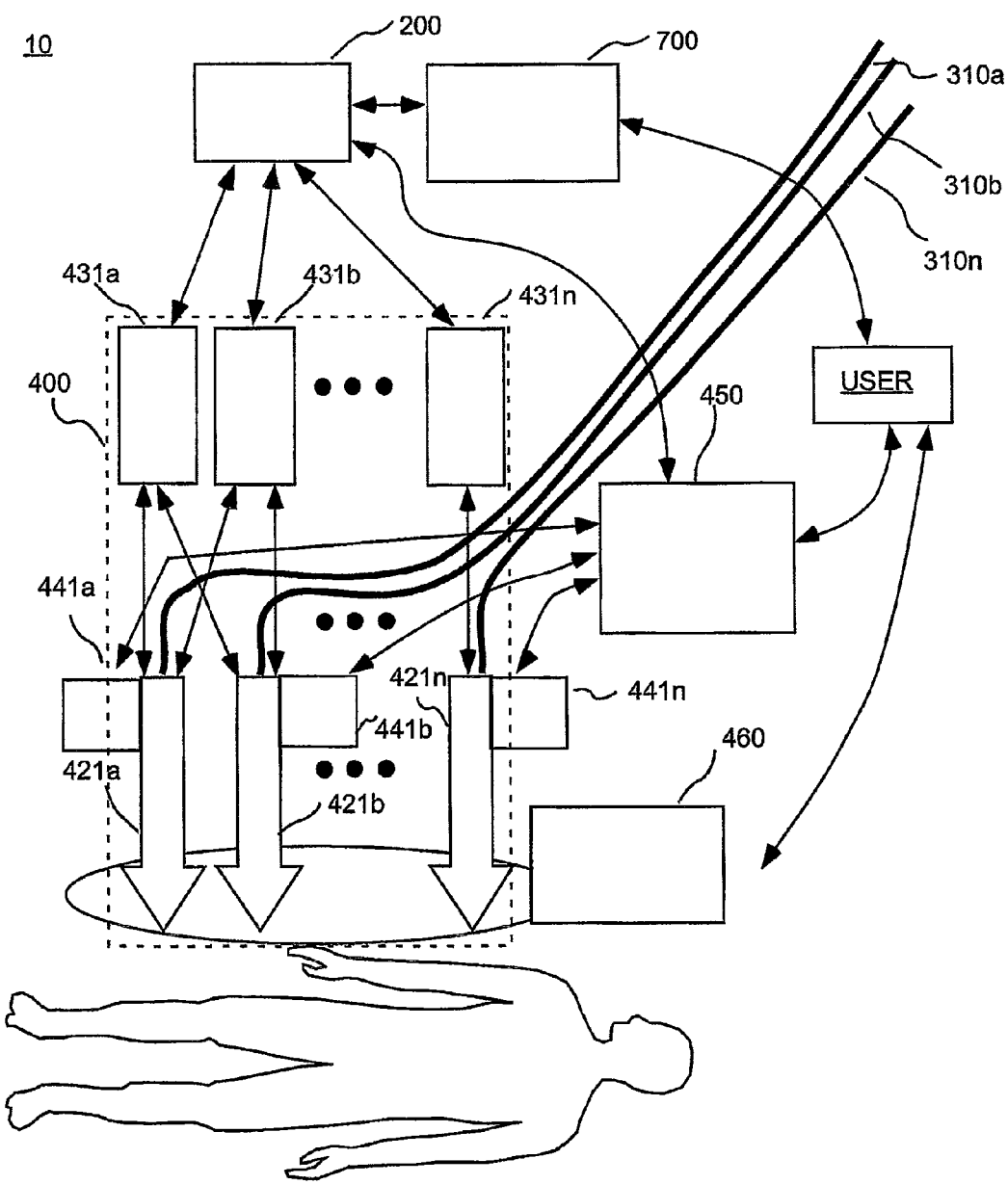
FIG. 4 illustrates a generalized embodiment of a patient interface of the present invention.

In general, patient interface 400 is the component of cell delivery system 5 that interfaces, interacts or interconnects with the patient to deliver a substance to the patient. Patient interface 400 is, for example, shown in operative connection with the patient's heart in FIG. 3 (and in connection with the patient's head/brain in FIG. 2). In a generalized embodiment as illustrated in FIG. 4, patient interface 400 includes one or more effectors 421$a$, 421$b$ . . . 421$n$, which can optionally be moved or otherwise altered by one or more actuators 431$a$, 431$b$ . . . 431$n$ in operative connection with effectors 421$a$, 421$b$ . . . 421$n$. Fluid is brought to effectors 421$a$, 421$b$ . . . 421$n$ through fluid path elements such as conduits 310$a$, 310$b$ . . . 310$n$. Actuators 431$a$, 431$b$ . . . 431$n$ (and effectors 421$a$, 421$b$ . . . 421$n$) are in communicative connection with control system 200. One or more sensors 441$a$, 441$b$ . . . 441$n$ can be in operative connection with effectors 421$a$, 421$b$ . . . 421$n$ and in communicative connection with control system 200 to provide, for example, feedback control of effectors 421*a*, 421*b* . . . 421*n*. Such communication can, for example, be effected via a sensor interface 450, which can be in communication with sensors 441*a*, 441*b* . . . 441*n* and control system 200. Sensor interface 450 can also be integrated with control system 200. Operation of actuators 431*a*, 431*b* . . . 431 and effectors 421*a*, 421*b* . . . 421*n* can also be controlled, at least in part, on the basis of data provided by other systems sensors and monitors (for example, measuring units 70, 72 and/or 74 and physiological parameter monitor(s) 600).

In current manual systems, there is a single effector—a needle, (or a catheter) a single piece of tubing connecting the needle to an injection fluid source and no actuator connected to a control system. The interface positioning system is generally a needle grip or forceps used by the doctor to manually maneuver the needle.

In one embodiment of the present invention, as discussed further below, one effector can be a single lumen needle or catheter and a second effector can be a depth stop mechanism. A fluid path element can be a single piece of tubing in this embodiment and there may be no actuators in operative connection with the control system. In a more sophisticated embodiment of the present invention, as discussed in more detail below, there can be a multi lumen (for example, concentric lumens) needle or catheter with multiple fluid path elements in fluid connection therewith. The depth stop can be operated by an actuator. Another actuator such as a grip, ball screw, and motor can, for example, cause the needle to be withdrawn as the injectate is deposited into the tissue.

Fluid Path and Fluid Flow

A. Cell Protection and Viability in Fluid Path Elements

In general, any component with which the injection fluid comes into contact during the injection procedure is considered part of the fluid path. With reference to FIG. 3, for example, in the fluid delivery stage, the fluid path for the injection fluid (including, for example, cells) can, for example, include container 50, manifold system 90, mixing system 99, conduit 310, fluid contacting portions of inline measurement unit or system 74 (if any), patient interface 400 and any intervening conduits of connectors.

Within the fluid path (in the fluid delivery state or elsewhere—for example, in the cell harvesting, cell storage, cell processing or any intermediate stages) turbulent stresses contribute strongly to mechanical trauma of cells. Conditions that contribute to or promote turbulence include wall irregularities, abrupt changes in tube dimensions, and disturbed flow upstream of a region of interest are common in current practice, as illustrated in the luer connector in FIG. 1B. In this invention, cell damage resulting from hydrodynamic forces during handling and delivery of injection fluid are preferably minimized by reducing the occurrence of or eliminating such conditions to, for example, improve therapeutic value. However, even damaged or dead cells may have therapeutic value in some instances, such as myocardial regeneration, whereas dead cells appear to have no value in other instances, such as the treatment of Parkinson's disease.

Figure 5A:
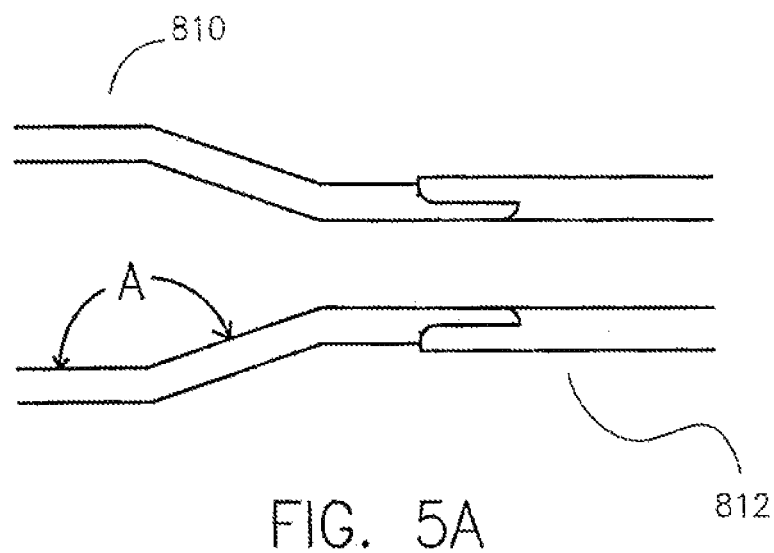
FIG. 5A illustrates an embodiment of a fluid path of the present invention providing for a gradual transition between inner diameters.
Figure 5B:
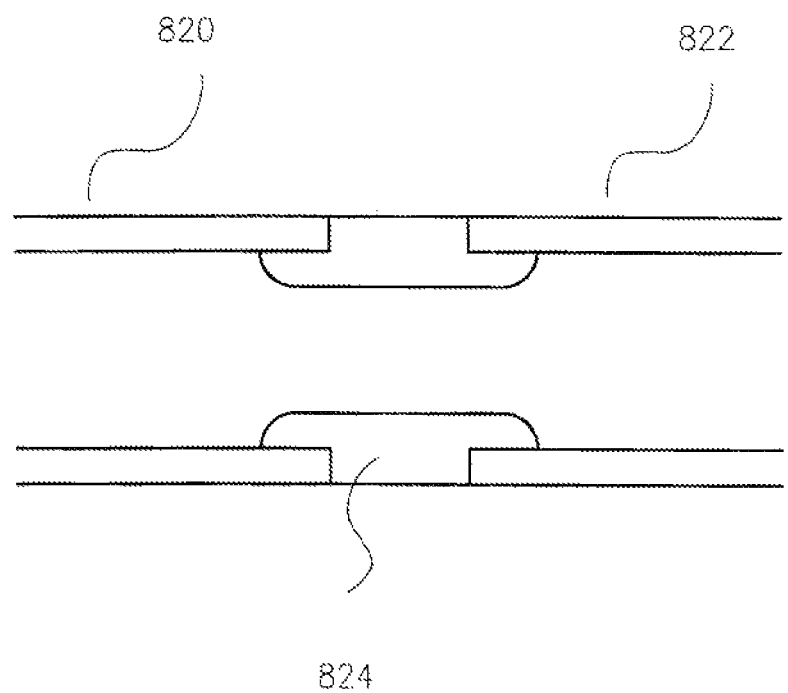
FIG. 5B illustrates an embodiment of a fluid path of the present invention including a connector providing for a curved, rounded or radiused transitions.
Figure 5C:
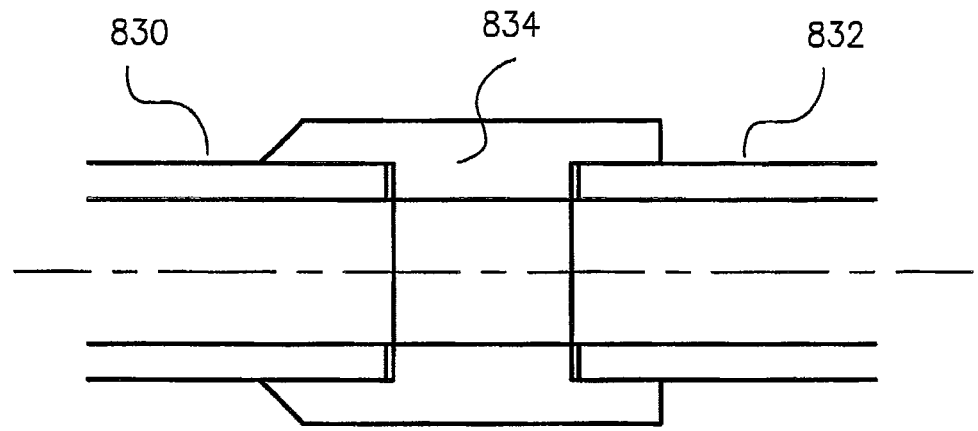
FIG. 5C illustrates the use of an intervening fitting or connector of the present invention to create a smooth transition between tubing and a needle.
Figure 5D:
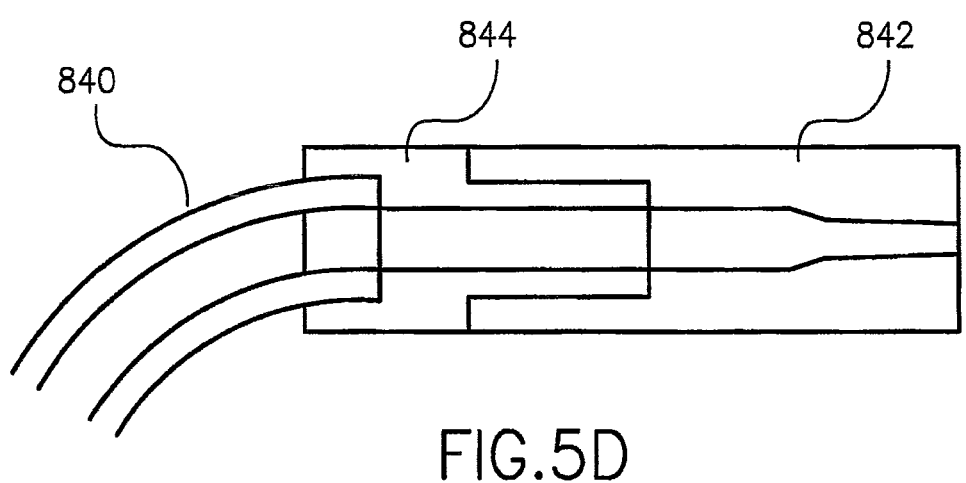
FIG. 5D illustrates use of another fitting, transition or connector of the present invention to connect a first section and a second section to provide for smooth internal diameters in the fluid path.

Hydrodynamic forces can, for example, be produced by providing for gradual transition within and between all fluid path elements. For example, FIG. 5A provides an example of a relatively gradual transition from a large radius section 810 to a smaller radius section 812. All edges or corners are preferably rounded or radiused as illustrated in FIG. 5B, in which a first section 820 is connected to a second section 822 via a connector 824 providing for radiused or rounded edges. In any area in which two fluid path elements are joined, the joints are preferably butted to reduce or eliminates sharp transitions or to provide for smooth internal diameters. For example, FIG. 5C illustrates the use of an intervening fitting 834 to create a smooth transition between tubing 830 and a needle 832. FIG. 5D illustrates the use of another fitting, transition or connector 844 connecting a first section 840 and a second section 842 to provide for smooth internal diameters in the fluid path. To ease the need to have very tight manufacturing tolerances, it is preferable that the fitting be relatively elastic so that it can accommodate the variations in ID and OD of the parts being mated. Alternatively, one of the other fluid path elements can be relatively more flexible and so adapt to the variations in the fitting. Assembly of one or more of the parts via insert molding can provide advantages because the variations can be accommodated in the molding process.

In most medical applications for the injection of fluid, tubing sets have no specific requirements other than containing system pressure without leaking and compatibility with the injection fluids. However, in certain applications that have more specific requirements including, but not limited to, cell delivery, delivery of ultrasound contrast and delivery of nuclear medicine, current tubing sets and connectors for use therewith (for example, Luer fittings) have serious shortfalls.

As described herein, in the case of delivery of cells, there is sensitivity to shear stresses induced in the cells. Moreover, there is sensitivity to lost volume (as relatively small volumes are delivered). Further, trapped material left in a connector can present a biohazard. Similarly, in delivery of ultrasound contrast there is sensitivity to lost volume as small volumes are typically delivered. Moreover, standard or conventional fittings used in the industry have areas where bubbles can collect and not be delivered to the patient. Nuclear medicine also uses relatively small volumes. Moreover, any trapped material left in a connector presents a radioactive hazard.

To limit loss, it is desirable to use the smallest diameter of tubing possible. In the case of cell delivery, however, care must be taken to avoid excessive shear. Currently most low-pressure tubing sets have a bore diameter on the order of approximately 0.060 inches. For certain applications the tube diameter can be on the order of approximately 0.020-inch diameter. This reduction in diameter reduces volumetric loss and increases flow velocity to assist in prevention of adherence of cells (or bubbles etc.) on the walls of the tubing. The length of the tubing is also preferably minimized.

Currently, luer fitting are widely used as connectors in connection with medical tubing sets and other medical components. The design of luer fittings cause the formation of small volumes of fluid that are not in the direct fluid path. That is, there are small volumes in the luer connector wherein material can collect and not be removed by a flush. These common luer fittings are not designed to maintain constant uniform diameter throughout the system.

As illustrated, for example, in FIG. 5E through 5H, the present invention provides a number of other fittings or connectors that provide for relatively low fluid loss. Such connectors also preferably provide for smooth transition between fluid path elements to reduce turbulence. In several embodiments of fittings or connectors of the present invention, a face seal can be used. In such an embodiment, the fitting includes flat faces that are mated together to make a seal. The faces can include compressible sealing elements. To reduce the likelihood of leaking, an annular seal (such as an o-ring) can be used. Use of an annular seal can provide for use of the connector at relatively high pressures with little tightening torque.

Figure 5E:
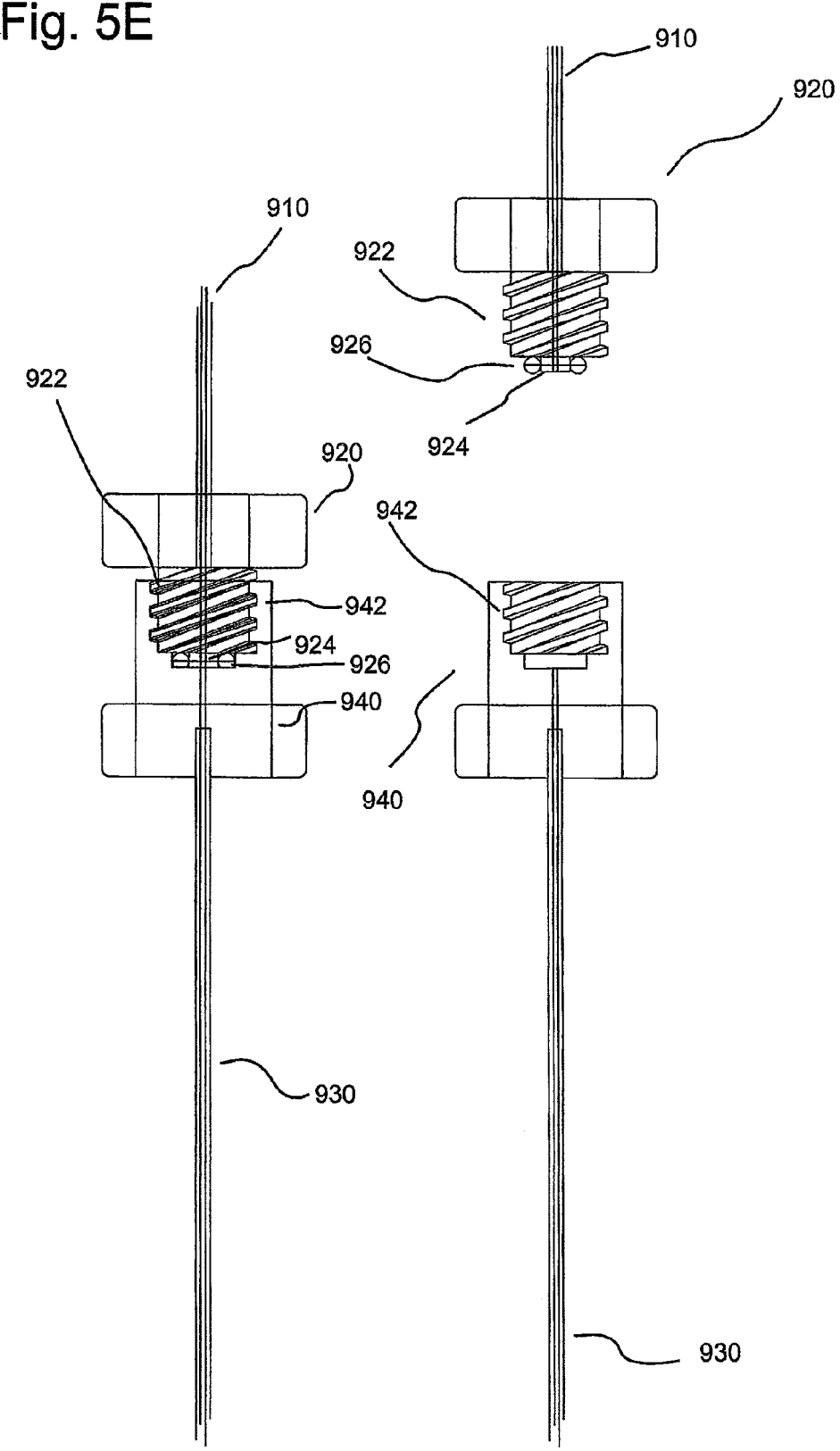
FIG. 5E illustrates a fitting or connector of the present invention that provides for relatively smooth transitions and low fluid loss.

In the embodiment of FIG. 5E, a first tubing section 910 (for example, a small diameter tubing section) is connected to or terminated by a male fitting 920. Male fitting 920 includes, for example, a connection mechanism such as threading 922. An end 924 of male fitting 920 includes (or has in operative connection therewith) a sealing member such as an O-ring 926. A second tubing section 930 (for example, a small diameter tubing section) is connected to or terminated by a female fitting 940. Female fitting 940 includes, for example, a cooperating connection mechanism such as cooperating threading 942. As illustrated in the left side of FIG. 5E, preferably there is no significant area change or change in inner diameter upon connection of male fitting 920 and female fitting 940.

Figure 5F:
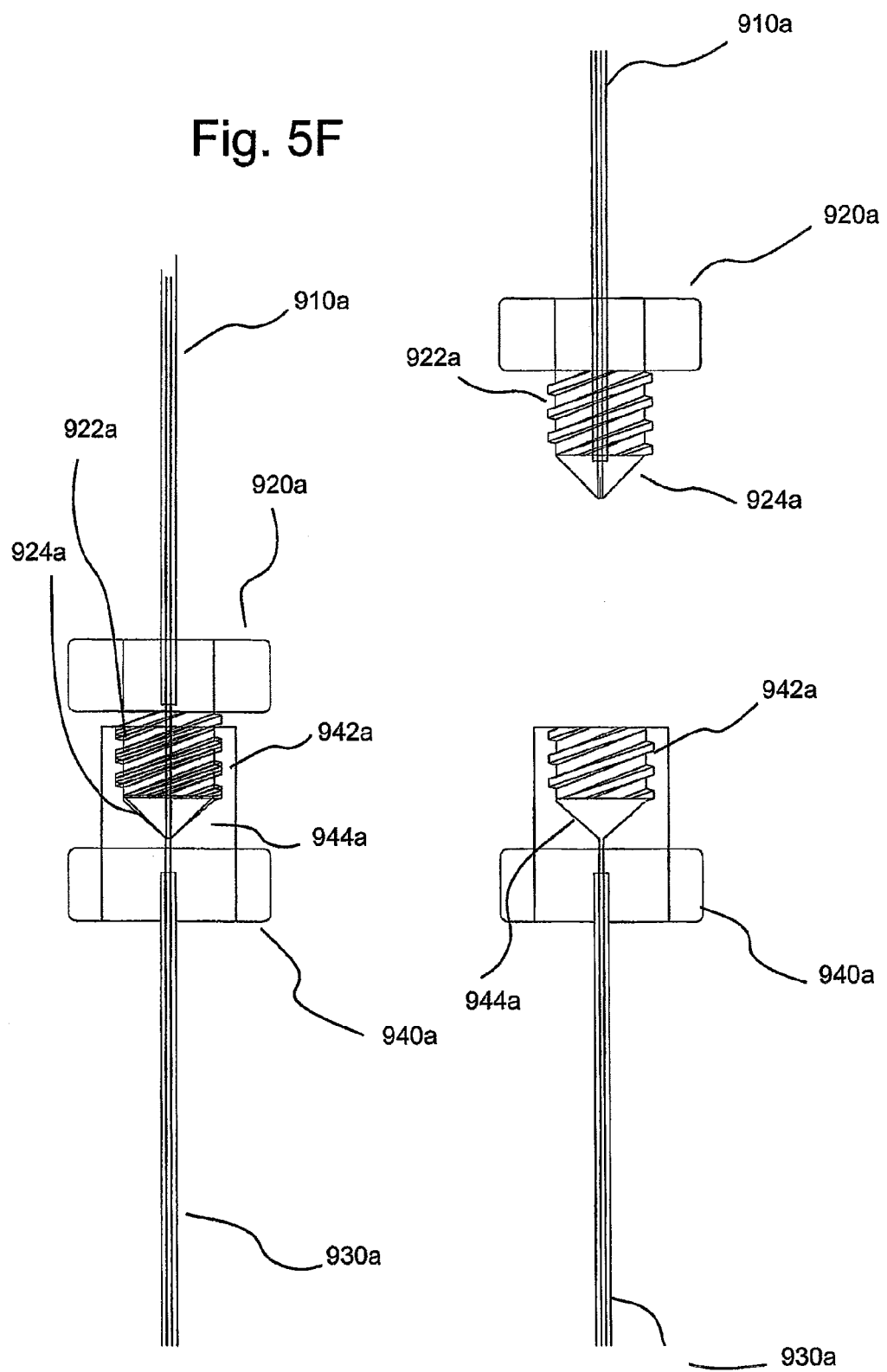
FIG. 5F illustrates another fitting or connector of the present invention that provides for relatively smooth transitions and low fluid loss.

In the embodiment of FIG. 5F, a first tubing section 910a (for example, a small diameter tubing section) is connected to or terminated by a male fitting 920a. Male fitting 920a includes, for example, a connection mechanism such as threading 922a. An end 924a of male fitting 920a is angled or tapered. A second tubing section 930a (for example, a small diameter tubing section) is connected to or terminated by a female fitting 940a. Female fitting 940a includes, for example, a cooperating connection mechanism such as cooperating threading 942a. Female fitting 940a further includes a seating 944a adapted to seat tapered end 924a of male fitting 920a. Seating 944a can, for example, have a taper angle generally the same as or slightly greater than the taper angle of tapered end 924a of male fitting 920a. As illustrated in the left side of FIG. 5G, preferably there is no significant area change or change in inner diameter upon connection of male fitting 920a and female fitting 940a. Male connector 920a and female connector 940a (or portions thereof) can be formed of a resilient or somewhat compliant material to assist in forming a sealed connection.

Figure 1A:
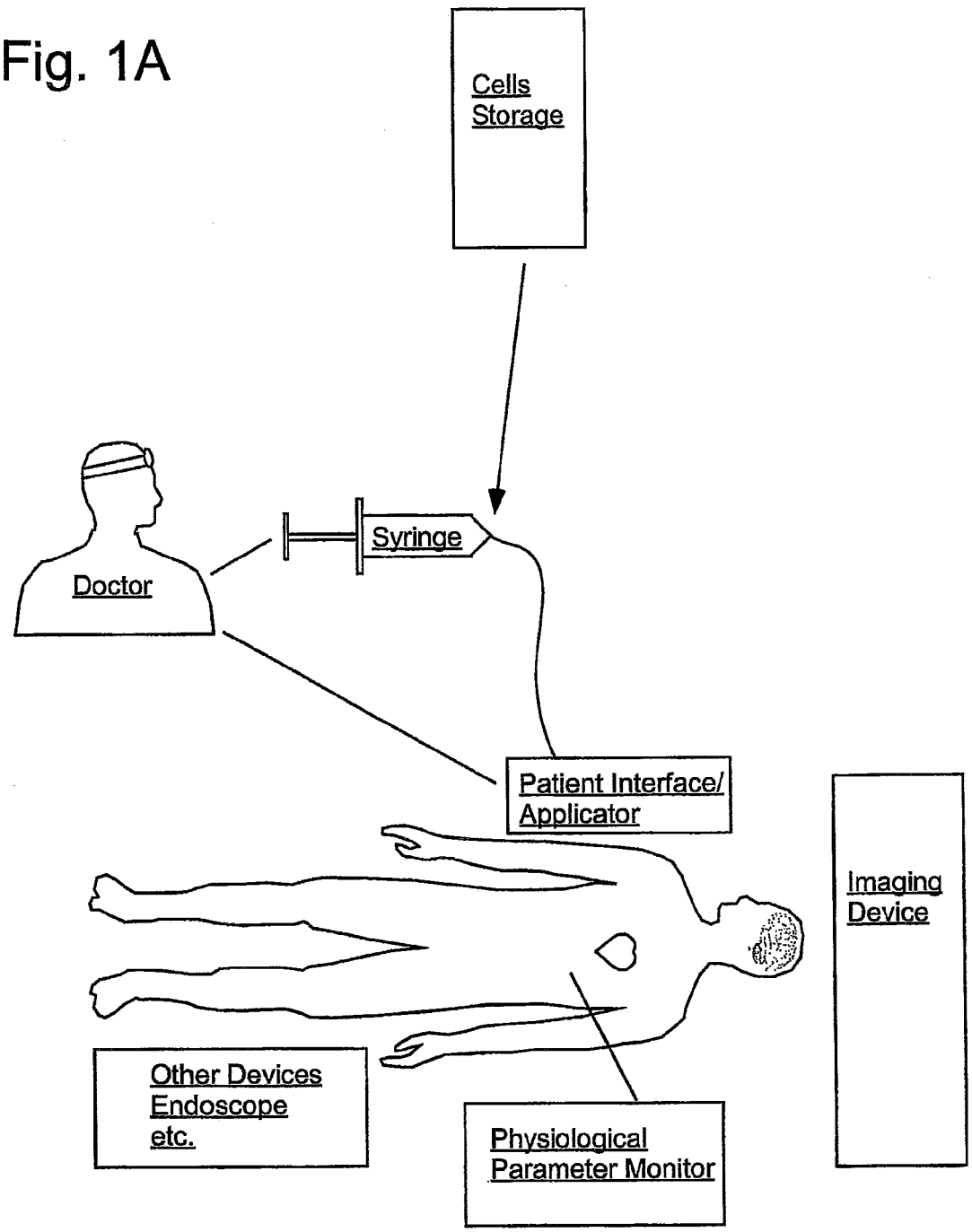
FIG. 1A illustrates a block diagram of an embodiment of a currently available system and method for injection of cells.
Figure 5G:
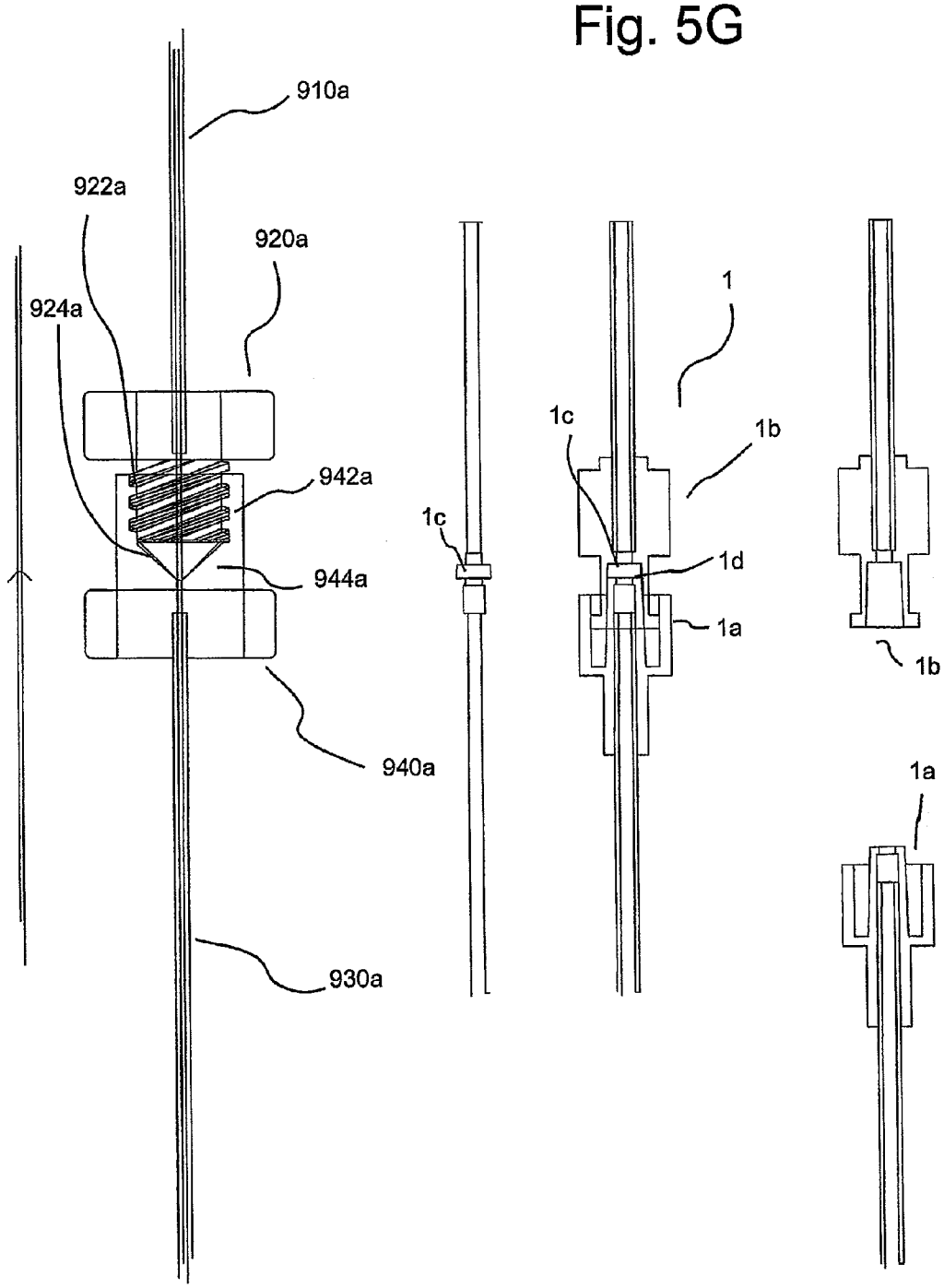
FIG. 5G illustrates a comparison of the fitting or connector of FIG. 5F with a standard luer connector.

FIG. 5G, on the right side thereof, illustrates standard luer connector 1 (as illustrated in FIG. 1B) in a disconnected state and in a connected state. A cross-section of the fluid path created upon connection of male luer connector 1a and female luer connector 1b, clearly showing the resultant lost volume region 1c and resultant sharp transitions, is also illustrated. For comparison, the left side of FIG. 5G illustrates the male connector 920a and female connector 940a of FIG. 5F in a connected state as well as a cross-section of the resultant fluid path, illustrating that there is no lost volume region or sharp transitions in inner diameter.

Figure 5H:
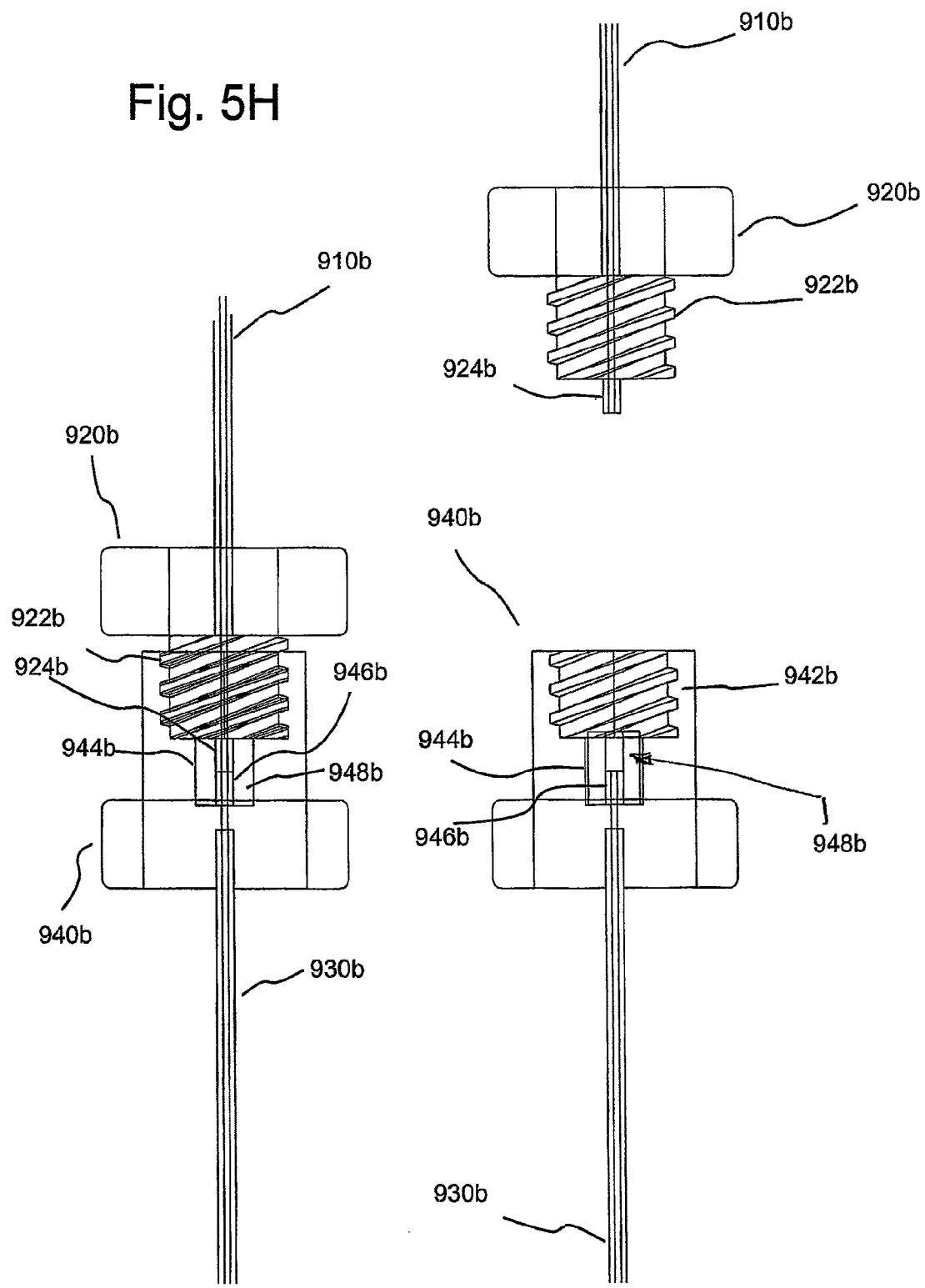
FIG. 5H illustrates another fitting or connector of the present invention that provides for relatively smooth transitions and low fluid loss.

In the embodiment of FIG. 5H, a first tubing section 910b (for example, a small diameter tubing section) is connected to or terminated by a male fitting 920b. Male fitting 920b includes, for example, a connection mechanism such as threading 922a. Male fitting 920b further includes and extending end member 924b. A second tubing section 930b (for example, a small diameter tubing section) is connected to or terminated by a female fitting 940b. Female fitting 940b includes, for example, a cooperating connection mechanism such as cooperating threading 942b. Female fitting 940a further includes a seating 944b adapted to seat extending end member 924b of male fitting 920b. Seating 944b can, for example, including an extending member 946b adapted to mate with extending member 924b of male fitting 920b. Seating 944b further includes a flexible sealing member 948b (for example, an elastomeric sleeve member) to encompass and assist in forming a sealing connection of extending members 924b and 946b. As illustrated in the left side of FIG. 5H, preferably there is no significant area change or change in inner diameter upon connection of male fitting 920b and female fitting 940b.

FIG. 5I illustrates an embodiment of a luer-type fitting or connector 950 having a through bore 952 sized to match the outside diameter of tubing 960 connected to fitting 950. Tubing 960 can, for example, be glued into luer-type fitting 950 in a position that allows a front face 962 of tubing 960 to compress and seal against a front face 972 of a syringe 970 (or other flow path element). This compressing abutment prevents fluid from entering a dead space area 954 of fitting 950. Fitting 950 further includes a tapered female portion 956 that mates with a tapered male portion 974 of syringe 970.

FIG. 5J illustrates an embodiment of a luer-type fitting or connector 950a having a sliding component 952a. A seal is made at a face 954a of sliding component 952a and tip or front face 972 of syringe 970 (or other flow path element). No seal is made at the luer tapers in this embodiment. A smooth transition is provided for the fluid path from syringe 970 to sliding component 952a. A smooth transition is also provided for the fluid path from sliding component 952a to tube 960a connected to fitting 950a. In the illustrated embodiment, an O-ring or other biasing member 956a at the rear of sliding component 952a provides spring compression or biasing force to hold face 954a of sliding component 952a against syringe face 972.

FIG. 5K illustrates another embodiment of a luer-type fitting or connector 950b which provides functionality similar to that provided by fitting 950a of FIG. 5J, but with no moving parts. A seal is made at a face 954b on the interior of luer-type fitting 950b and tip face 972 of syringe 970 (or other fluid path element). No seal is made at the luer tapers. A smooth transition is provided for the fluid path from syringe 970 to luer fitting interior face 954b. A smooth or gradual transition is also provided for the fluid path from luer-type fitting 950b to tube 960b. In that regard, the flow path within fitting 950b includes a tapered or angled region 956b having a first diameter approximately equal to the inner diameter of tube 960b and a second inner diameter approximately equal to the inner diameter of the syringe tip opening. A swivel nut (not shown in FIG. 5K, but see FIG. 5J) on the syringe tightens onto luer threads pulling face 954b of luer-type fitting 950b and syringe face 972 together and creating a seal.

FIG. 5L illustrates another embodiment of luer-type fitting or connector 950c having an internal protrusion or extending member 952c that fits within the inner diameter of the syringe tip fluid path (or other fluid path element). A smooth or gradual transition is provided by tapered or angled region or section 956c within protrusion 952c for the fluid path from syringe 970 to luer-type fitting interior face 954b. A smooth transition is also provided for the fluid path from luer-type fitting 950c to tube 960c via tapered region 956c. In that regard, tapered or angled region 956c has a first diameter approximately equal to the inner diameter of tube 960b and a second inner diameter approximately equal (or slightly smaller than) to the inner diameter of the inner diameter of the syringe tip opening. A seal is created via standard luer taper.

In another embodiment, two mating tapered elements are used. The tapered elements preferably have a greater angle of taper than a Luer connection (that is, greater than approximately 6 degrees). In several embodiments, the taper is in excess of 25 degrees. For example, in one embodiment a taper on the order of 45 degrees can be used. The male part of the taper can include a smaller angle of taper than the female taper (for example, about 5 degrees). The difference in taper allows contact in the center over a small area to provide a reliable seal with relatively little tightening torque.

B. Fluid Path and System Capacitance/Delivery Efficiency.

In the delivery of, for example, stem cells into tissue such as the heart muscle or the brain, it can be desirable to deliver a sharp bolus of cells in, for example, ten or more locations. Efficient transfer of cells to the muscle or the brain is important because of the limited quantity of cells available. The pressure required to deliver a bolus might not be available if there is too much capacitance in the system. Capacitance can defined as the ability of the system or an element of the system to increase in volume during pressurization, and then to relax to normal after pressurization. System capacitance can work like a spring absorbing pressure and releasing it when the pressure or restriction on the other side (increase load from heart muscle) of the needle is removed. The absorbing of pressure and subsequent release is why a system with a lot of capacitance will continue to deliver fluid or drip when a needle is withdrawn from the injection site. This dripping decreases the efficiency of the cells delivered, for example, to the heart and cells can be leaked into undesirable locations.

A certain level of capacitance in a fluid delivery system may be desirable, however, in certain circumstances. For example, if cells are damaged at a known shear force, the system can be designed to have enough capacitance to prevent the pressure from rising to the level that would cause shear to occur in the cells.

Figure 6A:
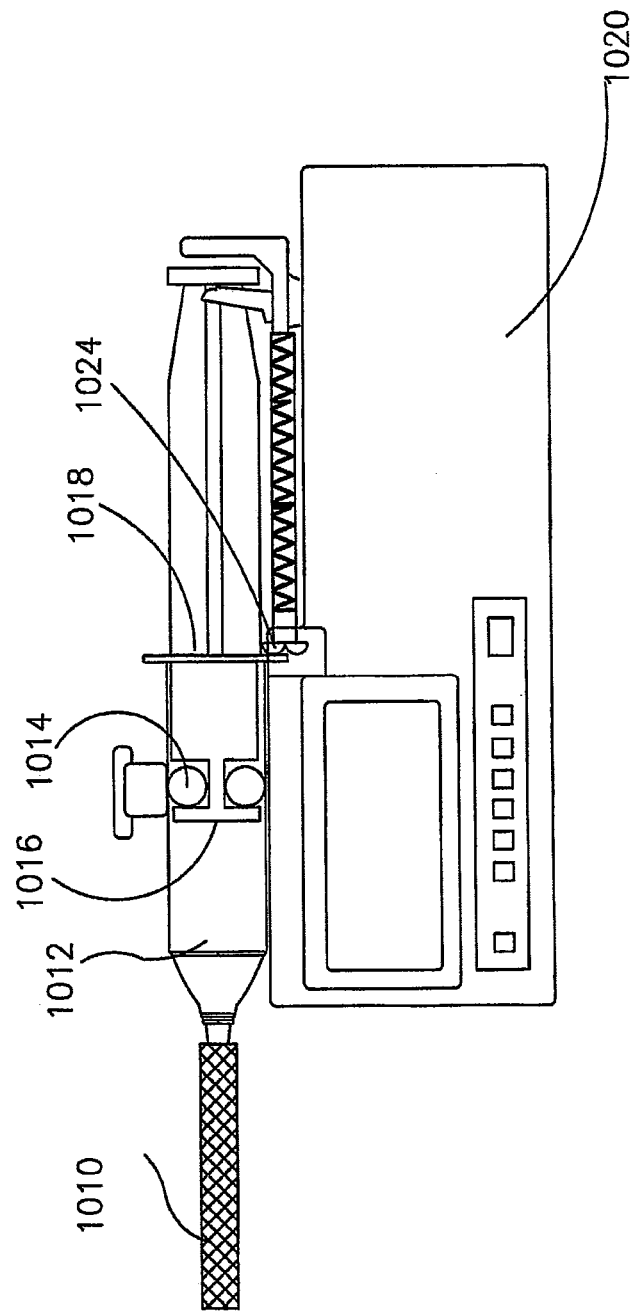
FIG. 6A illustrates a relatively low capacitance delivery system of the present invention including a braided or otherwise stiffened connector tubing.

However, excessive capacitance is undesirable. Capacitance reduction can, for example, be accomplished in several ways: As set forth in FIG. 6A, a braided or otherwise "stiffened" (for example, having thickened wall) connector tubing 1010 can be used. The fabrication material for container or syringe 1012 of FIG. 6A and other fluid path elements can be chosen to be stiff (for example, polycarbonate can be chosen rather than, for example, polypropylene—as polypropylene expands more under pressure). Alternatively or additionally, the wall thickness of syringe 1012 can be increased. O-rings 1014 or other sealing rings can be used around the perimeter of syringe plunger 1016 rather than elastomeric plunger covers. In that regard, elastomeric (for example, rubber) plunger covers can flex resulting in increased capacitance. Teflon seals can also be used in the syringe plunger. A tight fit of syringe flange 1018 in injector system 1020 can be provided, or a syringe sensor can spring load the flange forward (instead of rearward) as represented by element 1024 in FIG. 6A. Air causes capacitance because of its compressibility, therefore the efficiency of air removal from the system can also be improved. For example, a membrane that allows air to pass but prevents fluid from passing can be provided. Such a membrane can, for example, work at low pressure provided that the pressure is less than the membrane breakdown pressure of the filter. Backlash can be removed from system wherever possible. For example, the plunger can be spring loaded to reduce or eliminate backlash.

Figure 6B:
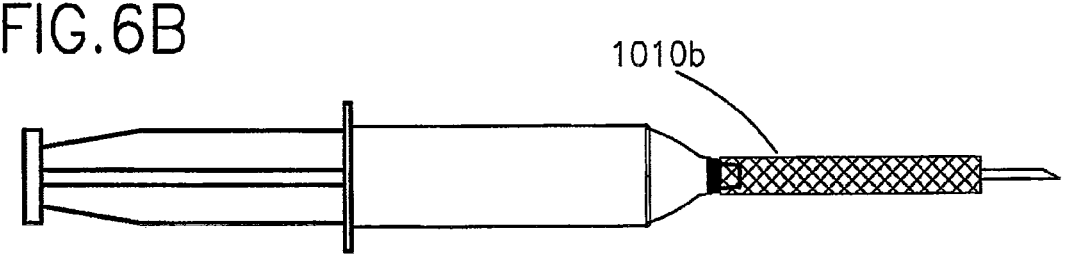
FIG. 6B illustrates an embodiment of a delivery system of the present invention including silicone tubing or other compliant tubing that allows only a defined amount of pressure to be delivered before it yields, thereby limiting the system pressure.
Figure 6C:
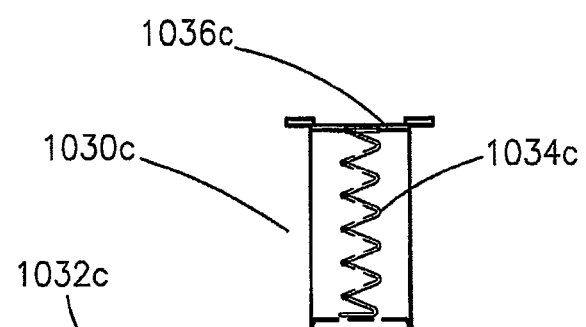
FIG. 6C illustrates a delivery system of the present invention including a separate spring loaded vessel to absorb pressure and to provide an indication to the operator that the desired pressure has been exceeded.
Figure 6C:
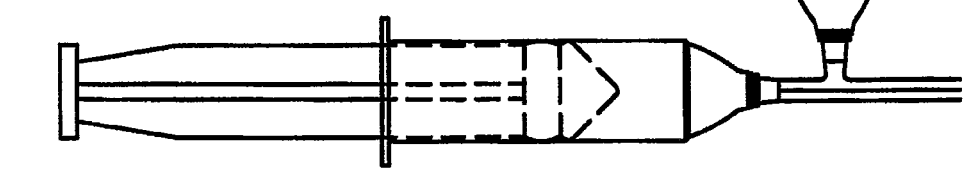

It may be also desirable to control the amount of capacitance of a system to protect the cells from exposure to damaging shear forces. If stem cells are destroyed at a known shear force, one can determine what pressure will develop that shear force for a known system configuration, i.e. if the disposable set is defined and a maximum shear force is established, then a maximum system pressure can be determined to reduce or eliminate the chance of exceeding the maximum shear force. As set forth in FIG. 6B, the system can include silicone tubing or other compliant tubing 1010b that allows only a defined amount of pressure to be delivered before it yields (for example, causing it to bulge) and limits the pressure. A maximum pressure setting can be set on an injector or pump system such as system 100 which can, for example, deliver to the maximum pressure and hold that pressure. As illustrated in FIG. 6C, a separate spring loaded vessel (for example, a syringe 1030c including a plunger 1032c loaded by a spring 1034c retained within syringe 1030c with, for example, a mechanical abutment or stop 1036c on the rearward end of syringe 1030c) can be provided to absorb pressure and to provide an indication to the operator that the desired pressure has been exceeded. This can, for example, be useful for the operator to determine when it is safe to remove the needle from the heart, brain or other tissue. If the pressure spikes and spring loaded plunger/indicator 1034c moves, then the operator can hold the device in the tissue until the pressure drops and spring loaded plunger 1034c returns to its original state (indicating that all the cells have been delivered to the tissue).

Figure 6D:
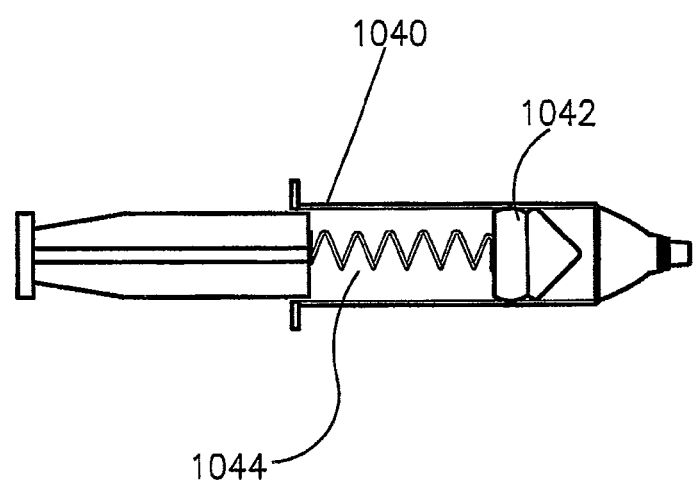
FIG. 6D illustrates a syringe including a spring isolated plunger designed such that an operatively connected spring or other biasing member will not compress under a predefined threshold load.

FIG. 6D illustrates a syringe 1040 including spring isolated plunger 1042 designed such that an operatively connected spring or other biasing member 1044 will not compress under a predefined threshold load. However, if pressure in syringe 1040 exceeds a threshold, spring 1044 will compress, limiting the pressure that can be developed in syringe 1040.

As illustrated in FIG. 6E, a normally closed, a push-button valve can be provided to activate pump system such as pump or injector system 100 and open fluid passage to needle 400: A normally closed push-button valve between the container/syringe 50 and the patient interface/needle 400 can, for example, have an electrical switch to initiate the pump system 100. By pressing or otherwise activating this valve, the fluid passage to the needle is opened and an electrical switch triggers injector/pump system 100. When the button is released, injector 100 can, for example, stop and the valve close. If the button is held down, injector 100 stops at a predetermined volume. Any dripping from the tip of needle 400 as a result of system capacitance is eliminated because the valve is closed and will not allow fluid to pass to needle 400. This embodiment can reduce the amount of wasted cells.

FIGS. 6F and 6G illustrate the use of a one-way check valve 1052, respectively, in a needle 1050, respectively. When the needle is placed in tissue (see FIG. 6F) such as in the heart, an activation rod 1054, respectively, is pushed rearward and check valve 1052, respectively, is opened. When needle 1050 is withdrawn from the tissue (see FIG. 6G), activation rod 1054 returns to a relaxed or unstressed state and check valve 1052 is closed, thereby preventing fluid leakage.

Figure 6H:
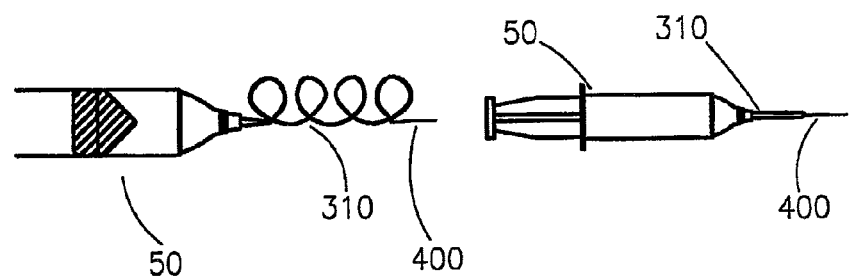
FIG. 6H illustrates a delivery system of the present invention in which capacitance is reduced by reducing the total volume of the system.
Figure 6I:
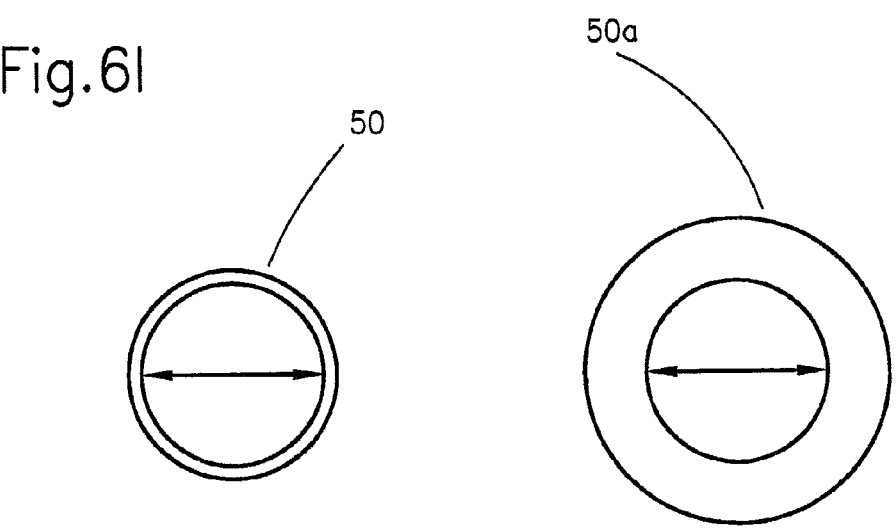
FIG. 6I illustrates decreasing of capacitance of a fluid path element by increasing wall thickness.

FIG. 6H illustrates reduction in capacitance by reducing the total volume of the system (as in comparing the injection system of the right side of FIG. 6H with that of the left side thereof). For example, the size of container/syringe 50 can be reduced and the length of fluid path 310 can be shortened. FIG. 6I illustrates the use of increase wall thickness (in for example, two syringe 50 and 50a) to reduce fluid path element capacitance.

FIGS. 6J through 6N illustrate an embodiment of a syringe 1060 in which capacitance is substantially reduced or eliminated. As described above, capacitance can negatively impact fluid delivery precision. Excessive capacitance delays fluid movement while the system expands as a result of hydraulic pressure. Subsequently, at the end of the injection, fluid will slowly exit or dribble while the system deflates as a result of pressure loss. This expansion and deflation prevents precise and controlled delivery. Specifically, with cell delivery, uncontrolled capacitance causes a slow continuation of exudates to exit the device without the proper force to deliver the cells to the target tissue. In the extreme case the exudates may even continue after the device is removed from the tissue, potentially exposing other, non-target tissue or clinicians to an unsafe condition.

In the embodiment of FIGS. 6J through 6N, the syringe barrel is designed for minimum strain or radial defection during the maximum pressurization. This can, for example, be accomplished by appropriate material selection and dimensioning as discussed above. Tensile strength, modulus of elasticity, and environmental conditions are important characteristics. As an example, in one embodiment using polycarbonate and given a radial stress of 115 psi, the maximum radial deflection is 0.001 inches, corresponding to a total volume increase of 0.10 mL within a 17 mL total volume syringe. Use of a solid, non-elasotmeric plunger 1062 with, for example, an O-ring side sealing member 1064 also helps minimize capacitance. Such a plunger minimizes fluid contact with an elastic surface (as, for example, compared to a plunger with an elastomeric cover of the forward and side surfaces thereof), while providing a seal against leakage. As described above, delivery tube can also designed and constructed to minimize capacitance. Syringe 1060 of FIGS. 6J through 6N, is preferably fabricated from an optically clear polymer such as polycarbonate to ensure visibility of the fluid contents. The material of syringe 1060 is also preferably blood- and cell-contact compatible. Optionally, the internal aspects of the fluid path and fluid path elements (including syringe 1060 and other fluid path elements) may have a lubricious coating, such as HYDROMER® (a hydrogel material made by the interaction of poly-vinylpyrrolidone with one of several, isocyanate prepolymers) available from Hydromer, Inc. of Branchburg, N.J. to, for example, reduce friction and/or maintain cell viability. Coatings can also be used to reduce plating or wall adherence. The internal aspects of the barrel are preferably adapted to minimize fluid turbulence and cell viability by, for example, providing radii at diameter transitions, as well as non-acute angles. A connector such as a male luer connector or fitting or a fitting of the present invention as described herein can be provided incorporating a rotating nut to aid in attaching the disposable tubing.

Figure 6J:
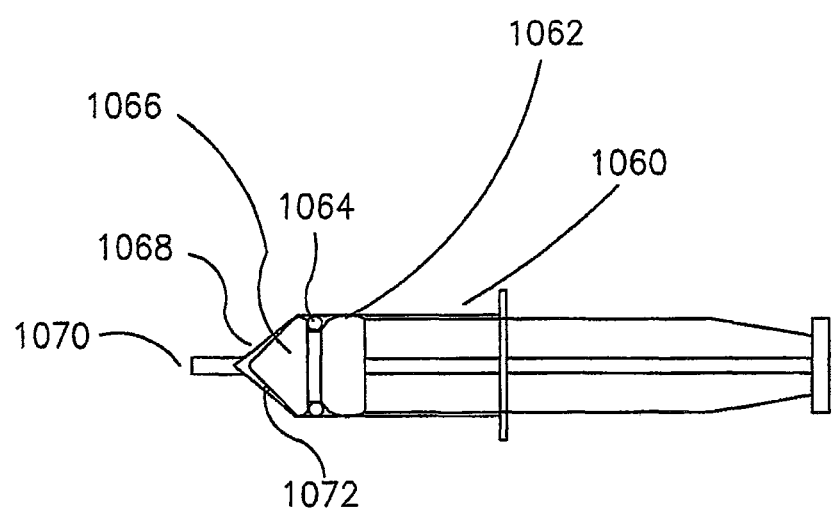
FIG. 6J illustrates a transparent or hidden line view an embodiment of a syringe of the present invention in which capacitance is substantially reduced or eliminated and wherein the syringe plunger is in a forward position.
Figure 6K:
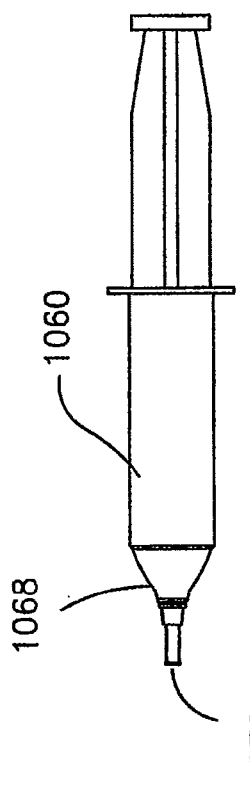
FIG. 6K illustrates a side view of the syringe of FIG. 6J.
Figure 6L:
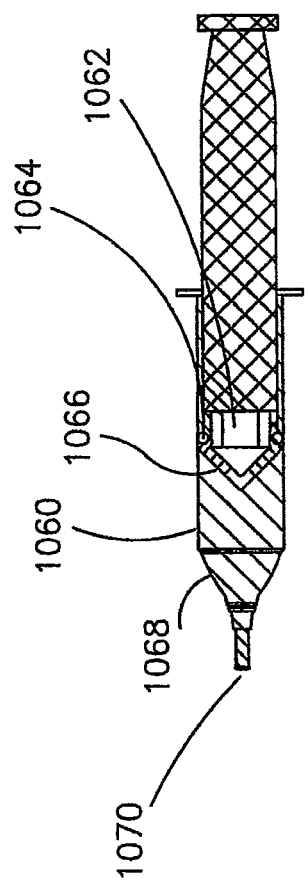
FIG. 6L illustrates a cross-sectional view of the syringe of FIG. 6J.
Figure 6M:
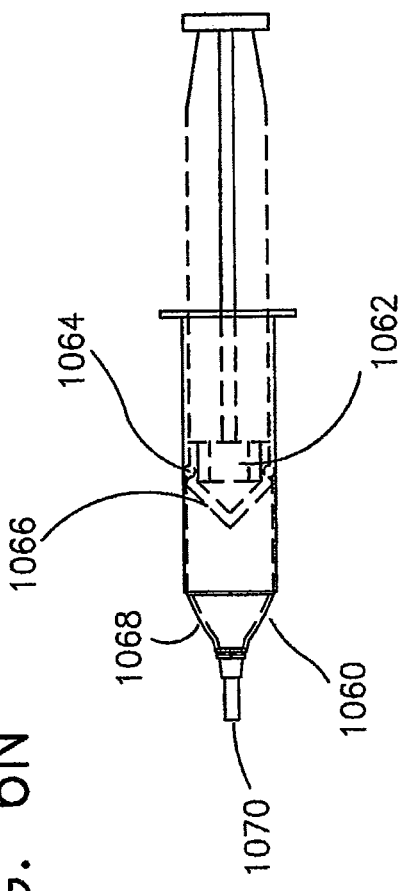
FIG. 6M illustrates another transparent or hidden line view of the syringe of FIG. 6J wherein the syringe plunger is in a rearward position.
Figure 6N:
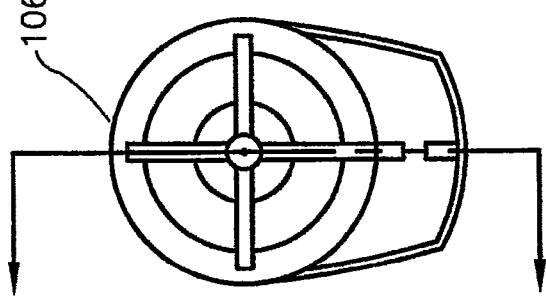
FIG. 6N illustrates a rear view of the syringe of FIG. 6J.

A distal angle of a forward section 1066 of plunger 1062 can be slightly smaller than the distal angle of a transition region 1068 of the syringe barrel (see FIG. 6J). This angle mismatch provides a channel for cells to exude through distal opening or syringe tip 1070 without getting trapped against the interior barrel angle. Typically, conventional syringe designs incorporate matching angles between the plunger and barrel. However, this arrangement causes both surfaces to touch simultaneously over a substantial portion thereof. While, such angle matching is a good design for most non-viable fluids, angle matching could damage cells caught between the two surfaces and lower the overall effectiveness of cell therapy. The described mismatch preferably minimizes the amount of residual fluid, while maintaining cell viability. One or more other abutment elements 1072 (see FIG. 6J) can additionally or alternatively be used to prevent mating of a forward surface of the plunger over a substantial area thereof with a surface of the transition region of the syringe.

When injecting into tissue with a system having capacitance, the pressure can ramp up quickly and gradually drop as the capacitance is taken up and fluid is injected into tissue (for example, the heart or the brain—see FIG. 6O). Once needle 400 is removed from the tissue, the pressure will drop suddenly as the tissue restriction to flow has been removed. When the pressure drops (as, for example, sensed by a pressure sensor 51'), the drive of pump system 100 can be reversed (for example, by moving a drive member in operative connection with a plunger in container/syringe 50 in a rearward direction), thereby stopping fluid from leaking out of patient interface/needle 400. Pressure sensing in injector systems is, for example, discussed in U.S. Pat. Nos. 6,673,033, 6,520,930 6,488,661, 5,808,203 and PCT International Patent Application Publication No. WO 00/06233, the disclosures of which are incorporated herein by reference. Pump system or injector 100 can be programmed to reverse or retract a certain amount at the end of an injection to relieve residual pressure from the system capacitance. FIG. 6P illustrates a graphical representation of a pressure profile with needle 400 within the tissue. FIG. 6Q illustrates a pressure profile with system capacitance and needle 400 removed from the tissue at time t.

C. Fluid Viscosity

In the case of cell therapy, the injectate or injection fluid typically includes at least one cellular component and a liquid or carrier component. Preferably the cellular component includes live, and undamaged cells, but damaged cells as well as dead cells can have therapeutic value also. The viscosity of the injectate can vary significantly. As discussed briefly above, cells (and cells supported, for example, on microspheres) do not behave like uniformly dispersed particles in a fluid. Among the problems arising in the fluid transport of cells are tendencies to clump together, to settle, to plate or adhere to walls of the fluid path and/or to stay in place while liquid flows through the "packed" cells (if flow velocities are sufficiently low). A number of approaches to address these problems are discussed above.

As also briefly discussed above, in several embodiments of the present invention viscosity can be used to reduce the significance of or overcome one or more of the problems listed above as well as other problems. Blood is a non Newtonian fluid, meaning that the viscosity is a function of flow velocity and thus the conditions of measurement. Blood at a normal hematocrit has a viscosity of about 4 centipoise at 37° C. under common ex-vivo test conditions. The viscosity of water is approximately 1 centipoise at 20° C. The viscosity of plasma is in between the viscosity of blood and the viscosity of water. A significant component of plasma is albumin, a large protein, which partly explains why plasma's viscosity is greater than that of water. As the concentration of albumin is increased, the plasma becomes more viscous.

If the fluid in the injectate is increased in viscosity, several benefits are realized. For example, the cells will tend to settle more slowly. If the density is increased at the same time, the tendency to settle will be decreased as well. As a result, for example, little or no agitation may be required to maintain the injectate in a homogeneous state. With regard to flow characteristics, a greater force is generally required to pull the cells off the walls and to break up the clumps or packing of the cells. With a more viscous fluid, the pressure at the injection site (commonly the tip of patient interface/needle 400) will be much greater before it starts leaking back the needle track, causing more of a cavity to be created in the tissue for deposition of injectate. Further, the more viscous injectate cannot as easily backflow or retrograde back up needle track or through fine structures/cavities in the tissue. In several embodiments of the present invention, it is preferred that the injectate viscosity be greater than 4 centipoise and, more preferably, greater than 6 centipoise. However, the optimal viscosity will typically depend upon patient interface 400 (typically a needle or a catheter system). In that regard, patient interface 400 is most likely to be the fluid path component with the minimum inner diameter. Given the flow characteristics of patient interface 400 and other system consideration, on skilled in the art can readily determine an optimal viscosity for a given application.

The viscosity of the injectate can be increased in several ways. One way of increasing viscosity is to increase the fraction of cells in the mixture. Increasing cell concentration has the additional benefit of require a smaller injection volume to deliver a desired number of cells. Thus, less pressure is built up in the tissue, and there will be less of a chance of fluid backflow or retrograde flow. Because of the increased number of cells per volume, the flow rate can also be reduced, thereby helping to maintain the same shear strain in the fluid. The cells can be concentrated by settling or centrifuging to create a concentrated fraction. Alternatively, the cells can be collected on a filter and back washed or suctioned into the delivery system.

Alternatively, the viscosity of the carrier liquid can be increased with the addition of, for example, non-essential or "excipient" cells (for example red blood cells) or other particles, such as collagen particles, for example spheres, in the range of tens of nanometers to tens of microns in diameter.

In the strategies discussed herein, it is desirable to maintain the proper osmotic pressure so that the cells are not adversely affected by swelling or shriveling. This can be measured and corrected by adding water or a salt solution as appropriate. It is also necessary to maintain the proper pH which can be done through various organic or inorganic buffers.

The viscosity of the injectate can also be increased by increasing the viscosity of the molecular part of the fluid, for example, by increasing the fraction of albumin in the liquid. This result can be accomplished by simply adding albumin to the fluid. Alternatively, the cells can be concentrated and separated from much of the liquid as discussed above, and a new liquid having a sufficiently increased viscosity added. The addition of dilute collagen molecules is another alternative. Both collagen and albumin have the advantage of occurring naturally in the body, and both are readily removed or decomposed. Other naturally occurring large molecules can be used as clear to those skilled in the art. Synthetic molecules can also be used. For example X-ray contrast is a large molecule, is water soluble, and has a high viscosity at physiological osmolality. Among X-ray contrasts, the greatest viscosity comes from those with dimmeric molecules, for example Visipaque (iodixanol) manufactured by Amersham Health, a division of General Electric Medical Systems. The 270 mgI/ml concentration has a viscosity of 6.3 centipoise at 37 centigrade, 12.7 centipoise at 20 centigrade and a physiological osmolality. The 320 mgI/ml concentration has a viscosity of 26.6 centipoise at 20 centigrade, also at a physiological osmolality. Thus, a reasonable amount of Visipaque will sufficiently increase the injectate viscosity. Addition of an imaging contract can also assist in a marking, tracking or mapping function in conjunction with imaging device or system 500. Other suitable synthetic materials include synthetic peptide hydrogels use to form the Puramatrix tissue scaffolding, made by 3DM Inc. of Cambridge, Mass. In sufficiently low concentrations, the long chain molecules increase viscosity of the injectate, but do not form a solid gel. Synthetic infusion products such as Hemohes, Gelofusine, and Venofundin manufactured by B Braun could be used. A particularly useful material is carboxymethylcellulose (CMC), an example of which is Aqualon manufactured by Hercules, Inc. of Wilmington Del. A 2% solution has a viscosity of 60-80 centipoise. CMC is used as a viscous carrier or excipient in Sculpta, an injectable treatment for lipoatrophy, available from Aventis Pharmaceuticals, Bridgewater, N.J. Additionally, molecules or droplets of inert synthetic large molecules such as perfluorocarbons or perfluoropolyethers (see, for example, Published PCT International Application No. WO002005072780A2, the disclosure of which is incorporate herein by reference) can be used. It is preferable to use molecules that are sufficiently large that viscosity is increased quickly.

The viscosity of the injectate can optionally be increased to the point that it can be described as a gel or a paste. In the case of a gel or paste, the cells move very little with respect to each other. The cells can be considered to be trapped in the gel. When the gel is injected, there is very little backflow or retrograde of injectate back through the needle track or through the tissue. The cells would initially stay where they were deposited. If the gel is made primarily of collagen, synthetic peptide hydrogels, or alginate, and the volume deposited is small enough that oxygen and nutrients can diffuse to the cells (which depends upon the density and type of cells), the cells will eventually be freed by the body's decomposition or degradation of the gel. The cells are then able to migrate, divide and/or perform the function(s) needed to achieve the treatment.

Because of the high viscosity of a gel or paste, the injections are either relatively slow, or a lubricating fluid, for example water, can be used between the gel and the walls of the fluid path to reduce the pressure and shear stress on the cells. Gels containing water tend naturally to form a water layer near the fluid path wall. Alternately, water can be injected from one of multiple containers or syringes 52 and 54 etc. concentrically around the gel as a lubricant. In the case of a gel, it is important that, as discussed above, transitions in inner diameter of fluid path elements be as gradual as possible.

The cells can, for example, be mixed with a precursor or pregel material before gelling occurs. Alternatively, an open gel can be created and then used as a filter to collect the cells. The cells would be embedded into the gel. Previous work on tissue scaffolds can be applied in this way to cell injections. An example of such a matrix is the Puramatrix scaffold made by 3DM Inc. of Cambridge, Mass.

As the viscosity is increased still further, a rod or other element of "solid" cell-containing material is "injected" or deposited. The solid injectate can be created or formed as a rod outside of the injection device, and then loaded into the injection device as, for example, lead is loaded into a mechanical pencil. Alternatively, the injection device can be loaded with fluid/liquid injectate that solidifies in the injection device. Components that form a gel can also be separately introduced into the injection device, where they are mixed, and the gel forms. An example of such a material is alginate, which forms a gel in the presence of calcium ions. A material of this type is made by Neural Intervention Technologies, Inc of Ann Arbor, Mich. The alginate and the cells can, for example, be mixed. When calcium chloride is added, the cells are trapped in the alginate matrix as it forms. This solid can then be injected and the cells and will not leak back the needle track or elsewhere.

Alternately, a solid, cell-filled matrix can be created by growing cells into and through the matrix. Patient interface 400 in the form of a needle can be filled with the matrix by simply inserting the needle into the matrix and cutting a core. This coring/loading can be done by hand but is more repeatable if done using a mechanized fixture suitable to ensure that the needle cuts different sections each time. When the needle is placed into the proper position in the patient's tissue, the solid core is displaced from the needle by, for example, pushing from behind with liquid or with a solid stylet.

As mentioned above, one of the benefits of injecting a high-viscosity material or a solid is that it does not leak back the needle track, leak out of the tissue and into surrounding tissue/organs or spread throughout the tissue. However, those attributes limit the cell location to a small area within the tissue. In some uses, such as cell implantation in the scalp or into the brain for Parkinson's disease, this limitation is not a problem. In some other applications, such as cell therapy for the heart, current theory of operation dictates that the cells be applied over a range of tissue area. Thus, to spread the cells over a range of tissue, it is desirable that the viscous fluid or solid be injected as the needle is being pulled back as described above. The cavity created by the needle is filled, or optionally overfilled with injectate, rather than the return of the displaced tissue. If the needle is inserted at a shallow angle with respect to the tissue surface, this approach allows a large area to be treated even with a very viscous material. This concept can be used with multiple needle embodiments as described above. The coordination of the injection and needle withdraw is preferably accomplished, at least in part, using control system 200.

Alternatively, solid injectates can be premanufactured into cylinders that are inserted into multiple implantation needles as lead is placed into mechanical pencils.

Figure 6R:
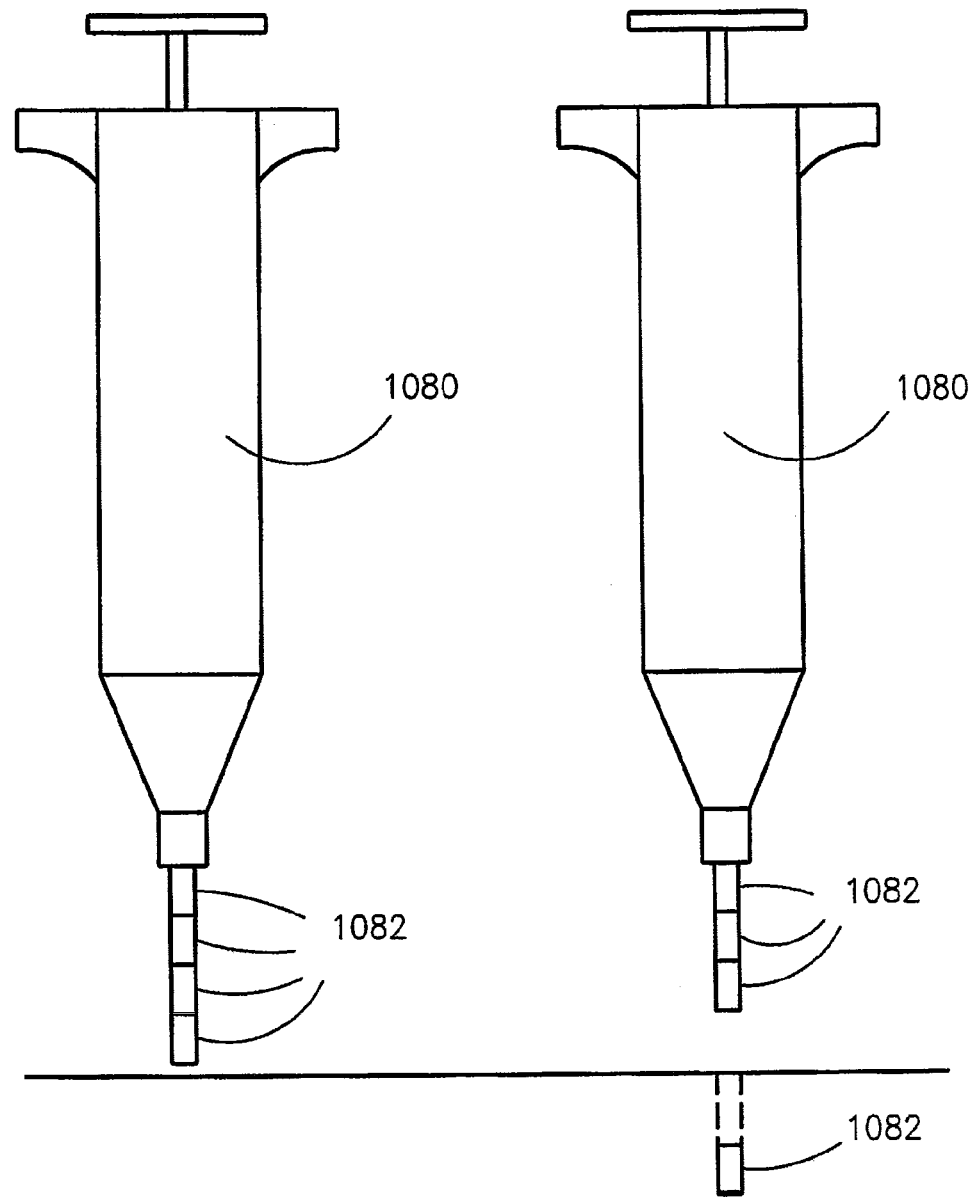
FIG. 6R illustrates an embodiment of a delivery system or applicator of the present invention in which a generally solid component, element or plug is placed within tissue.

In still a further embodiment, solid rods containing cells can be formed to themselves pierce and embed within tissue such as heart or brain tissue without the assistance of a needle or catheter. Multiple piercing or penetrating rods or other solid injection elements can, for example, be applied generally simultaneously or in a single application as an array with an applicator. FIG. 6R illustrates an example of an applicator 1080 including breakaway sections 1082 of solid injectate that are sequentially embedded, fully or partially, in the tissue (see the right side of FIG. 6R). The breakaway material can serve any number of additional functions, including, but not limited to, acting as a buffer that protects the primary therapeutic material from damage, a mechanism to push the primary therapeutic to further depth in the tissue, a cap for the therapy site, or as a color, radiological or other marker to allow the user to keep track of the injection visually or with a secondary sensing or imaging device.

If the needle holds more solid injectate than is delivered in a single injection, it is desirable to stop the delivery before or as the needle leaves the tissue. This is best done if control system 200 operates the injectate delivery and a depth stop. In this case the depth stop can be settable by control system 200. The user can, for example, set the initial depth and the volume to be delivered. The needle is then inserted until the depth stop contacts the tissue. The injector is then activated. As the injection occurs, the depth stop is moved so that the needle is controllably extracted as the injectate is delivered, while the user simply maintains contact between the depth stop and the tissue. User interface 700 can indicate when the injection is complete and the user can move to the next site. The depth stop can be used to ensure proper depth of penetration. Such drive mechanism can readily be controlled by control system 200 using control algorithm procedures as known in the art.

D. Generalized Cell Delivery Flow Modes

The discussion of the multiple and various flow modes and embodiments of this invention can, for example, be described generally with reference to FIGS. 7A through 7F. In FIG. 7A, three fluid path elements are shown diagrammatically as concentric cylinders A, B, and C, in this figure. The distal ends marked respectively with Ad, Bd, and Cd are the ends closest to the patient. The effectors are the distal ends of the fluid path elements that interact with the patient and the means for holding or position the effector. A fluid path is determined by one or more of the fluid path elements. In FIG. 7A, fluid path 1 is inside fluid path element A. Fluid path 2 is inside fluid path element B and outside of fluid path element A. Fluid path 3 is inside fluid path element C and outside of fluid path element B. Fluid paths 1 and 2 communicate where fluid path element A ends, and fluid paths 2 and 3 communicate where element B ends. This communication may be at or in the patient, or at some point before reaching the patient.

A fluid path can be made up of one or more physical fluid path elements, which may be made of any of the many materials known to those skilled in the medical device arts that can contain the fluid within them, either flowing or static, without contaminating the fluid. For example, they can be a single rigid fluid path element, such as a metal needle. They can be flexible, such as plastic tubing or catheters. Some elements can be rigid and others can be flexible. Or, a single fluid path can be made up of multiple fluid path elements, such as a flexible fluid path element, piece of tubing, connected to a rigid fluid path element, such as a needle.

The fluid path elements illustrated in FIGS. 7A to 7F are downstream of the powered pump and the manifold or their equivalents, if they are used in the system. By fluid path element is meant any element that touches the fluid, including the pumps and manifolds not shown in FIGS. 7A to 7F. The effectors of FIG. 4 that contact the fluid are included as fluid path elements.

The simplest fluid path is shown in FIG. 7B. It has one fluid path element A and one fluid path 1. In this invention, there are a number of fluids that can and will be transmitted via this fluid path. In the manual practice discussed in the background, the fluid path element A is a needle that is connected to a syringe for injection of a fluid with cells or drugs. In the prior art manual methodologies, the pump is the syringe and the operator's hand, the control system is his or her brain, the fluid being injected is the therapeutic fluid containing cells, and there is no manifold. The pump directly injects in to the fluid path 1.

In several embodiments, the present invention replaces the hand with one or more mechanically or electrically powered pumps or controlled injectors. If multiple injectors and/or a multi-container injector are used with a manifold or valve arrangement (see, for example, FIG. 3), then several fluids can be injected either sequentially or serially. As an example, fluids used include the therapeutic injectate, and could for example include one or more of saline or a similar physiological fluid for priming the fluid path elements or flushing the therapeutic injectate, a viscosity modifying agent, a lubrication agent, a tissue cracking or opening agent, a site marking agent, and a sealing or gluing agent to seal the site or fill the needle or catheter track. The detailed uses of such fluids are discussed in various parts of this description.

One embodiment with two fluids includes the therapeutic fluid and saline. The fluid path 1 is first filled with saline to remove all air from the path. Then, depending upon the volume contained in the fluid path as compared to the volume of the therapeutic fluid to be injected, the purging fluid can be left in the fluid path while the effector, needle in this case, is placed in the target tissue. The purge fluid in the fluid path is simply injected into the tissue before the injection of the therapeutic fluid. And, optionally, the injection of the therapeutic fluid can be followed by an injection of a flush fluid, for example saline, to drive more of the therapeutic fluid out of the fluid path elements and into the tissue.

In FIG. 7C, there are two fluid path elements, A & B. Similarly, there are two fluid path elements shown in FIG. 7D. An arrangement similar to this was disclosed in Published U.S. Patent Application No. 2004/0254525 A1, the disclosure of which is incorporated herein by reference. In that application, it was used to surround the injection of a drug that harmed vessel walls with a second fluid that did not harm the walls. In the current invention, injecting the therapeutic injectate through fluid path 1 and a fluid such as saline with a relatively lower viscosity through fluid path 2 will help protect the cells in the therapeutic injectate from the high shear stress as they travel through fluid path 2 to the patient. Using readily available computational fluid dynamic (CFD) modeling, for example Fluent and other software packages available from Fluent, Inc. of Lebanon, N.H., it will be possible to select the appropriate flow rates and velocities to maintain the desired flow and safe shear stress levels. In this case, it is likely that the distance of travel outside of fluid element A, the physical distance from Ad to Bd, will be relatively long.

A second application of the fluid paths of FIGS. 7C and 7D involves non-simultaneous delivery of fluids. The initial fluid through fluid path 2 could be relatively high pressure and velocity to "crack" or open a space in the tissue. After that fluid dissipates into the tissue, or after it is sucked back out through fluid path 2, then the therapeutic injectate can be delivered through fluid path 1. Alternatively, the second fluid is delivered through fluid path 2 after the therapeutic to flush or drive the therapeutic fluid into the tissue. A third application, show in FIG. 7D, has the vector distance Ad to Bd be very short or in fact negative. (A negative Ad to BD vector distance means that the fluid path element A actually sticks out past fluid path element B.) In this application of the embodiment, the injectate flows toward the patient in fluid path 1, and some of the injectate is drawn back in away from the patient through fluid path 2. The laws of fluid mechanics cause particles or objects in a developed fluid flow of sufficient velocity to concentrate in the center of the flow away from the walls. This happens in normal blood flow in the arteries. In physiological systems, some blood vessel branches use a "cushion" of tissue to take blood from the cell rich center flow. (*Physiology and Biophysics of the Circulation*, 2$^{nd}$ Edition 1972, Alan C Burton, LC#70-182003, chapter 5) In the opposite way, fluid path 2 is removing some of the fluid with less or no cells, so that the total fluid volume injected into the tissue is reduced for a given number of cells being delivered to the tissue. This reduces or eliminates the tissue swelling needlessly increased by fluid that is of no therapeutic value. Alternatively, fluid path 2 could withdraw fluid just long enough to remove the purging fluid from the system, but not withdraw fluid when the therapeutic fluid arrives. Fluid path 2 could incorporate a filter to ensure that cells are not needlessly removed and wasted.

Alternatively, fluid path 1 could be used for delivery of the therapeutic fluid and fluid path 2 is used to deliver a site marking fluid or a needle or catheter track filling. This is most likely done with an embodiment where fluid path element A extends past the end of fluid path element B so that fluid path 1 is not occluded by the track filling fluid. In addition, fluid path 2 could transport a fluid that reacts with the fluid in fluid path 1, for example, calcium ions that will cause the alginate in fluid path 1 to gel.

One of the challenges with cell delivery is that the cells tend to settle, stick, or clump to themselves or on the insides of the fluid path elements. One approach to over come this is to start the flow with a higher or more rapid velocity than is used for the majority of the injection. A second approach is that of FIG. 7E. The injectate is pulled back fluid path 1 while a purging or physiological solution is injected at the same flow rate down fluid path 2. This reverse flow in fluid path 1 will help loosen any clumping or adhesions, without pulling any fluid out of the patient. Then, when the injection starts to flow in the forward direction in fluid path 1, there is suction out fluid path 2 until it removes a volume approximately equals the volume that had been previously injected down fluid path 2. Similarly, this helps ensure that little or none of the purge fluid is delivered to the tissue. Then the injection can proceed according to the preferred delivery scheme.

FIG. 7F shows the fluid path elements of FIG. 7A, with an exemplary fluid flow indicated. Fluid path 1 carries the therapeutic injectate, fluid path 2 is delivered simultaneously with a lower viscosity "lubricating" fluid. The two fluids flow together to the end Bd of fluid path element B. At end Bd, the lubricating fluid is removed by suction on fluid path 3 so that a more concentrated cell carrying fluid is delivered to the tissue. From this example, it is apparent that all of the functions described above with respect to two fluid paths can be realized with the 3 fluid paths of FIGS. 7A and 7F.

In some embodiments, a solid needle, commonly called a stylet is inside the hollow fluid path element when it is inserted into the tissue. This is often done so that a core of tissue does not fill the hollow fluid path and to minimize the damage to the tissue. However, when the solid stylet is withdrawn, it created a suction on the tissue at the tip, and/or the hollow fluid path is filled with air. It is generally desirable that this air not be injected into the patient, especially when the delivery is through catheters in the blood vessels. A multiple fluid path embodiment similar to that of FIG. 7F can be used eliminate this problem. When fluid path element A is originally a solid stylet, fluid path 2 can be used to slightly pressurize the space around element A, so that as it is moved, fluid flows to fill the space. This requires a seal at the proximal end of fluid path element B. Such seals, often made of an elastomeric material, are well known in the medical arts, especially in regards to catheters in interventional and special procedures labs. Hemostasis valves and needleless ports are examples of similar devices.

It is preferred that the injection of marking or track filling fluid is automatically coordinated with the withdrawal of the effector. The position of the effector can be tracked with various methods known in the art. Similarly, the injection of the therapeutic fluid can be synchronized with the motion of the effector, so that the track left by the effector is filled with therapeutic fluid. The marking could occur simultaneously with the indication to the user that the injection is over and that the needle can be removed, as was discussed above.

While stylized fluid path elements have generally been discussed and can, for example, be concentric cylinders. In many cases this optimizes the uniformity of flow and helps preserve laminar flow. Eccentric cylinders can generally be easier to manufacture, especially if they touch and have a wall in common, and they may have some benefits in use. In addition to not demanding concentricity, most of the concepts of this invention can also be accomplished with parallel or adjacent fluid path elements, or in fact totally separate fluid path elements that only meet or connect at the patient. In the connection, they may then have or not have concentricity, dependent upon the need to be separate or mixed and upon the details of the fluids. The assembly of structures in such embodiments use techniques well known in the medical device and disposables art. Gluing can be used to assemble separate molded and/or machined parts. Insert molding can be used advantageously in some instances to capture metal or plastic elements in other plastic elements. Co-extrusion can create fluid path elements of significant length. Assembly with elastomeric seals is applicable to some embodiments such as those of FIGS. 5C and 5D.

In addition, the drawings of FIGS. 7A to 7F are for clarity of understanding and are not to scale in length, width or proportions. The fluid path elements may change diameter, cross section, shape, or size or taper over their length. Example geometries are discussed in relation to the examples applications. Generally for clarity and consistency, the therapeutic fluid is discussed as being delivered through fluid path 1, however, generally the fluids can be transmitted through any of the fluid paths provided that the fluid path elements are compatible with the fluids and the shear stresses are sufficiently low. The walls of fluid path elements are shown as lines. As discussed elsewhere, turbulence is generally damaging to cells.

The necessary rounding or tapering of any edges depends upon the thickness, roughness, and fluid flow parameters to be used in a particular case. The generation of turbulence can be modeled and avoided using computational fluid dynamics packages as described elsewhere. In some embodiments and applications the effector itself does not need to penetrate the tissue but is inserted through a needle, through a previously made track, or over a guidewire. In others, where it needs to be strong and sharp enough to penetrate the tissue, there will be competing design needs on fluid path element wall thickness and edge geometry. It is anticipated that because the therapeutic fluid is flowing into the tissue at that point and entering an uncontrolled geometry, the desire for laminar flow can be relaxed and that the sharp edges will most likely be beveled in any event, which will minimize any step transitions and their subsequent generation of eddies.

Pump/Injector System and Container

In several embodiments of the present invention, pump/injector system 100 is designed to mechanically deliver fluid to tissue and, particularly, the myocardium. As discussed above, among the potentially beneficial fluids that can be delivered, autologous bone marrow-derived progenitor cells offer promise in the treatment of diseases of the heart tissue such as occurs in congestive heart failure and dopamine producing cells offer promise in treating, for example, Parkinson's disease. In light of these and other applications, in several embodiments of the present invention, pump/injector system 100 was designed with special attention to, for example, the handing and delivery of such cells. Features preferably present in several embodiments of a pump or injector for delivery of such cells include: 1) consistent, repeatable dosage size, 2) a 15-30 ml total volume, packaged in a disposable container, and/or 3) a specified volume to be mechanically injected on demand in a defined period of time, for example, one second or less. Thus, in several embodiments of the present invention, pump/injector system 100 provides consistent and accurate delivery of a specified volume of fluid into, for example, the myocardium of the heart or the brain, ensuring that the total volume is accurately distributed across the total number of injections and delivered at an appropriate rate.

In an embodiment illustrated in FIG. 8A, a disposable container or syringe 50" can be snapped securely and reliably into place with pump/injector system 100" in a simple, two-step operation. The easy and secure mounting of disposable container or syringe 50" reduces operator effort and time while also reducing the risk of error. The simple operative attachment enables syringe plunger 56" to be pushed forward for injections and withdrawn for removal and disposal (if necessary) with little user effort. As illustrated in FIG. 8A, injector 100" includes a seating or cradle section 105" for receiving syringe 100". A rearward section of syringe plunger 56" includes an attachment flange 58", which cooperates with a retaining seating 112" on a forward end of injector drive member 110". Flange 58" and/or seating 112" can, for example, be formed from one or more resilient materials (for example, polymeric materials as known in the polymer arts) so that a snap fit is formed to securely retain syringe 50" within seating 105" and within operative connection with injector 100". To attach syringe 50" to injector 100", syringe 50" is angled with respect to injector 100" as illustrated in the upper left portion of FIG. 8A. In this angled orientation, flange 58" is first placed in connection with seating 112" and then syringe is moved into alignment with seating 105" as illustrated in the upper right portion of FIG. 8A.

As illustrated, for example, in FIG. 8B, mechanical drive, drive member or piston 110" pushes the disposable syringe's plunger 56" forward with, for example, a screw drive. Injector drive mechanisms are, for example, described in U.S. Pat. Nos. 4,677,980, 5,383,858, 6,585,700, Published PCT International Patent Application No. WO 02/04049 and U.S. patent application Ser. No. 10/921,083, filed Aug. 18, 2004, the disclosures of which are incorporate herein by reference. The screw drive can, for example, be powered by a highly accurate stepper motor 120" and a small, powerful battery 122". This reliable method of driving a small pump maintains accuracy and power in a suitably small package.

Figure 8C:
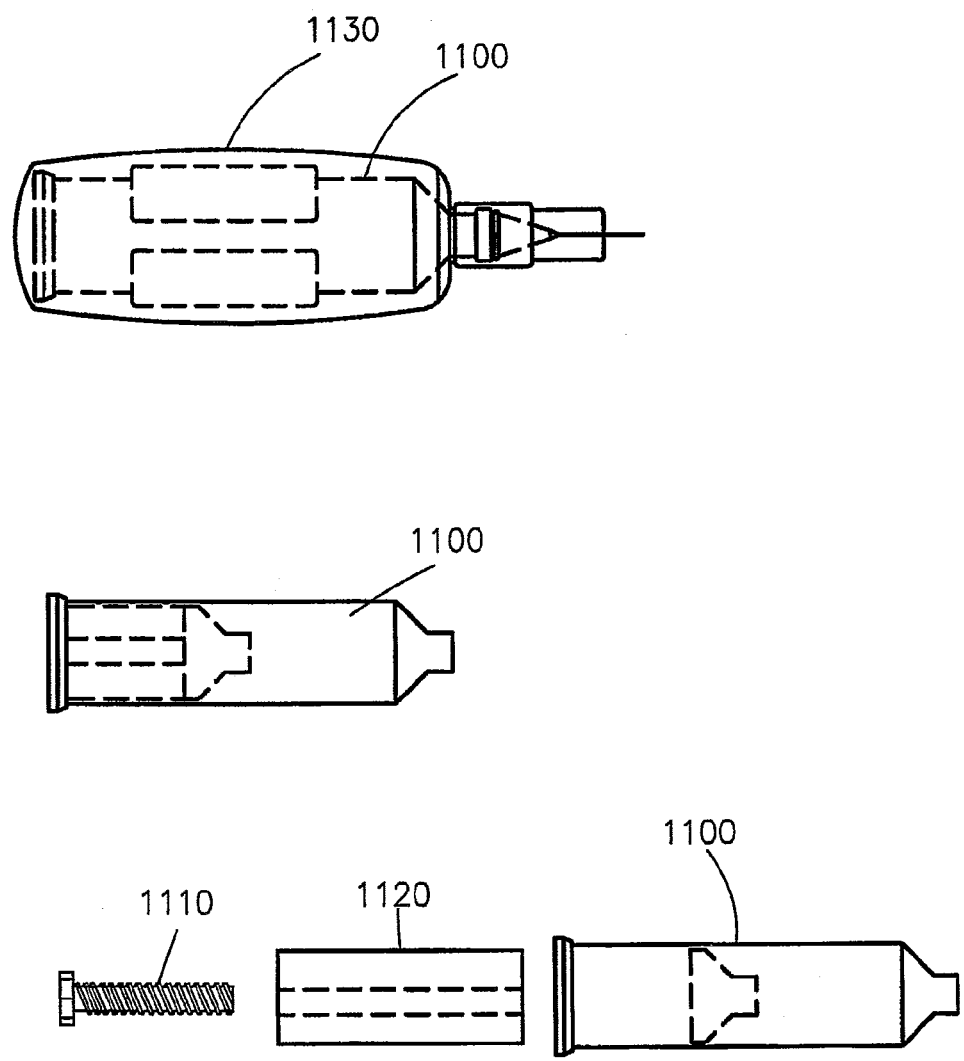
FIG. 8C illustrates another embodiment of an injector system of the present invention.

As illustrated, for example, in FIG. 8C, a custom assembly 1100 including screw-drive components 1110 and portions of an electromagnetic motor 1120 can be inserted into a handle/housing 1130 containing additional circuits and motor components as known in the art, thus completing the motor assembly necessary for driving an injection. This significantly smaller approach to a mechanical drive assembly provides an injector suitable for even the smallest fluid injection volumes.

Figure 8D:
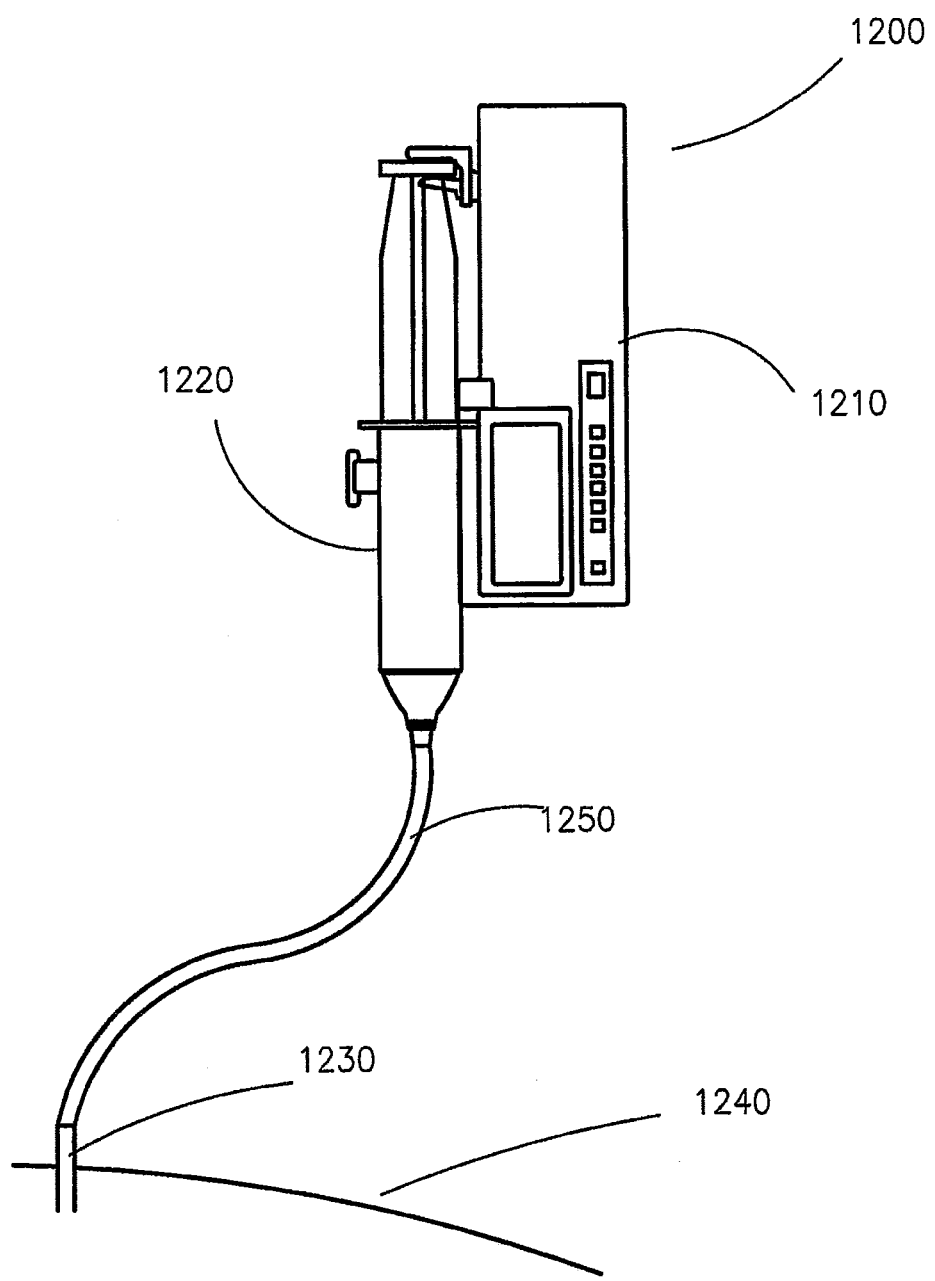
FIG. 8D illustrates an embodiment of an injection or fluid delivery system of the present invention for use, for example, in connection with a stereotactic localization frame.

FIG. 8D illustrates use of an embodiment of a pump/injector system 1200 of the present invention for the use of injection of, for example, SPHERAMINE into the brain of a patient. In this embodiment, the injector system includes a syringe pump 1210 to deliver the SPHERAMINE from a syringe 1220 to the patient. As further described in connection with FIG. 9C below, syringe pump 1210 can be enclosed in a sterile bag or other containment system or barrier. In the illustrated embodiment, syringe 1220 is placed in fluid connection with a needle 1230 localized by a stereotactic frame or similar localization device 1240 via a length of flexible tubing 1250. As known in the art, needle 1230 can be provided with a removable stylet to prevent coring upon advancement within tissue. Further, needle 1230 can pass through a cannula in operative connection with stereotactic frame 1240. As compared to current manual techniques, connection of syringe pump system 1210 to needle 1230 via flexible tubing 1250 isolates needle 1230 and stereotactic frame 1240 from force, torque, or vibration.

As compared to current manual injection of SPHERAMINE, pump driven system 1200 of the present invention can also provide the benefits of flow, volume and pressure control and auto loading. Pump system 1210 is also capable of reversing before injecting, delivering the dose in pulses or conducting a two-phase or multi-phase injection.

In several embodiments, the injectate of interest (for example, SPHERAMINE) can be present only within needle 1230 and a flushing fluid is used to inject the SPHERAMINE into the brain of the patient. Such embodiment can, for example, limit shear experienced by the injectate.

Figure 8E:
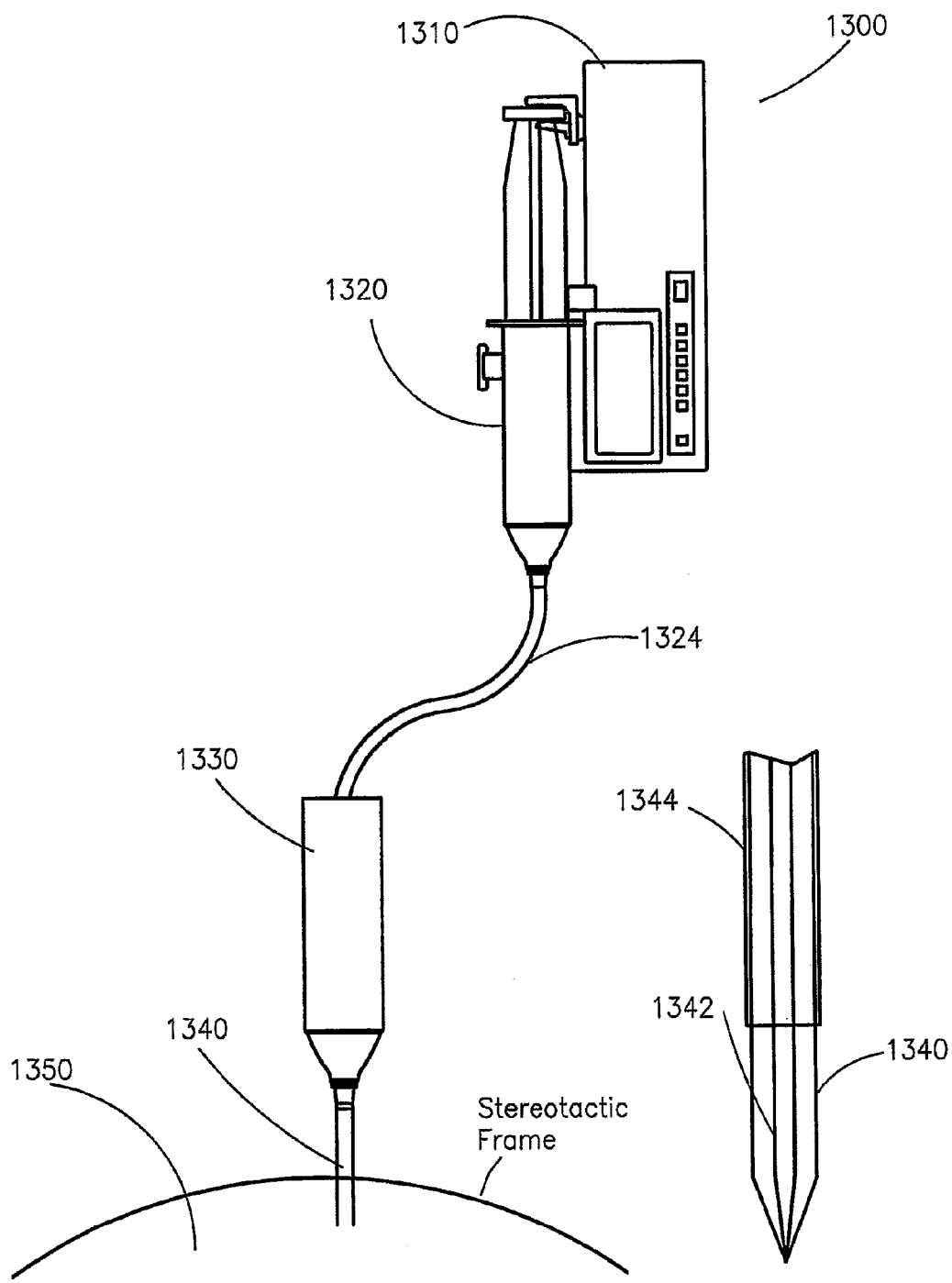
FIG. 8E illustrates another embodiment of an injection or fluid delivery system of the present invention for use, for example, in connection with a stereotactic localization frame.

FIG. 8E illustrates another embodiment of an injection system 1300 of the present invention suitable, for example, to inject cells (for example, SPHERAMINE). In this embodiment, a syringe pump or other injector 1310 in operative connection with a syringe 1320 including a fluid therein is used to mechanically or hydraulically drive a syringe 1330 (via tubing or conduit 1324) that delivers SPHERAMINE to the patient via a needle 1340 in operative connection with a stereotactic frame 1350. Once again, syringe pump 1310 and/or other components of system 1300 can be enclosed in a sterile barrier. By using syringe pump 1310 or other drive mechanism to drive syringe 1330 containing, for example, SPHERAMINE, as opposed to delivering the SPHERAMINE directly as illustrated in FIG. 8D, the fluid path length for the SPHERAMINE is reduced.

In several embodiments, the pump/injector systems of the present invention can be programmed to deliver a calculated volume, which equates to a predetermined amount of viable cells based on an algorithm such as a statistical algorithm. For a desired amount of stem cells the algorithm determines the required volume for a given time in the life cycle and processing time of the drug.

For example, it is known that FDG decays with a half-life of 110 minutes from the time it is fabricated. It is also known that living stem cells have a nominal life under the conditions they are subjected to during delivery, and experience a settling or packing as a result of time and syringe/vial orientation.

Given this information, the injector calculates from the time the cells were cultured to the present time to determine the percentage of live (viable) cells remaining in the syringe/container. If there is any significant settling that occurs over time, the injector can calculate the amount of settling and deliver a flow profile that, for example, includes less volume in early injections and more volume in later injections, or vice versa to provide a consistent amount of viable cells from the first to the last injection for a given container. The algorithm can calculate the volume required for each injection to deliver the predetermined amount of viable (viable cell count) cells for each injection. Other factors such as a slide cell count or temperature of the culture can also be considered in the algorithm. If cell measurements are taken periodically during a delivery session, this can be used to update the algorithm.

Further, if stem cells are known to require a high flow rate to break them loose from, for example, the needle, tubing, or syringe, the flow can be tailored to deliver a high flow at the beginning of the injection to break the cells free and taper off to give a steady delivery of cells over time.

User Interface System

The surgical field is often a crowded, stimulus-filled environment. The user of the devices and systems of the present invention is often wearing layers of surgical gloves, a gown, mask and face shield. User interface system 700 (see FIG. 4) of fluid delivery system 5 preferably provides easy, adequate and appropriate feedback and input control to the user during operation.

The feedback or information provided to the user can include, but is not limited to: total volume injected; volume remaining to be delivered; injection dosage volume; status of an injection in progress; map of injection area (for example, a 3-D computer generated map), position of injections made, position of injections to be made, cell viability, number of cells injected, number of cells reaming, and flow rate. The controls provided to the user can include, but are not limited to: dosage volume; injection start/stop; injection position, and flow rate. The controls afforded the user further preferably provide the user ready access to, and accurate control of, a repeatable, accurate and consistent dose size, without the inherent inaccuracies of a manually controlled injection.

Figure 9A:
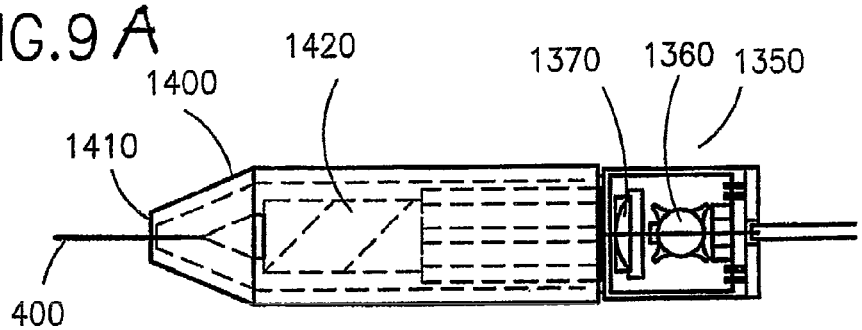
FIG. 9A illustrates an embodiment of a handheld switch or control assembly for use with an injector system.
Figure 9A:
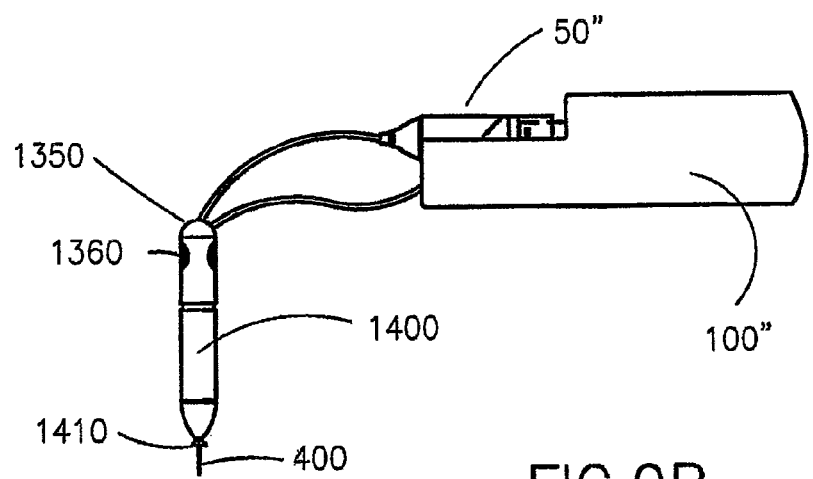

In one embodiment as illustrated in FIG. 9A, a switch assembly 1350 is operatively connected in the vicinity of patient interface 400 (for example, to a depth stop mechanism 1400—either permanently or temporarily). Depth stop 1400 can, for example, include an abutment surface 1410 that abuts tissue and thereby limits the depth to which needle 400 penetrates tissue. The position of abutment face 1410 relative to the distal end of needle 400, and thus the penetration depth, can, for example, be adjusted via threading 1420 or other adjusting mechanism. Switch assembly 1350 can be used to trigger discrete injections. A button mechanism 1360 or other interface can, for example, provide tactile feedback to the user. Also, a small LED 1370 connected to the switch circuitry can be used to visually signal the start and stop of each injection.

Figure 9B:
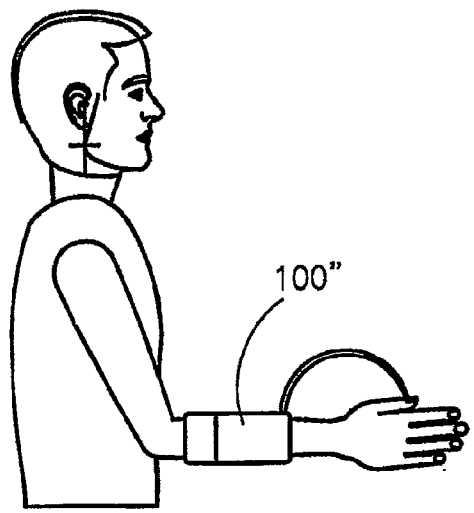
FIG. 9B illustrates the switch or control assembly of FIG. 9A in operative connection with the injector system of FIG. 8A.
Figure 9C:
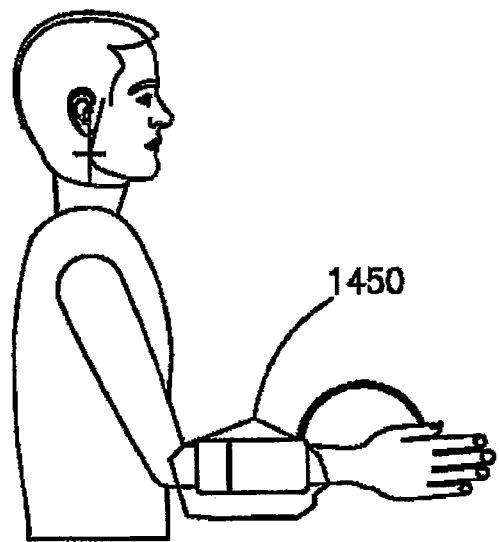
FIG. 9C illustrates the injector system of FIG. 8A as worn on the arm of an operator, wherein a sterile barrier surrounds the injector system.

In the embodiment of FIG. 9B, the system subassembly of pump/injector 100" and syringe 50", which is shown in operative connection with switch assembly 1350 and depth stop mechanism 1400, is attachable to and worn by the user. Part or all of control system 200 can also be contained within the injector housing. The user can, for example, operate the system by attaching the system subassembly to the forearm of the user, thereby freeing up both hands to manipulate the fingertip unit/switch assembly 1350 (see FIG. 9B through 9D) in the surgical field. With both hands free, the user has a greater degree of physical dexterity and an increased control of accuracy and precision during the procedure. Moreover, a user wearable injector system can free valuable space in the surgical field. FIG. 9C illustrates the use of a sterile barrier 1450 to enclose at least a portion of the fluid delivery system of the present invention. In the embodiment of FIG. 9D, barrier 1450 is, for example, a flexible barrier (for example, a flexible polymeric material) that is wearable by the user of the system subassembly of pump/injector 100" and syringe 50". The user can, for example, don the wearable system subassembly of pump/injector 100" and syringe 50" outside of the sterile field and then don sterile barrier 1450, covering the subassembly, to maintain sterility in the sterile field. Alternatively, the subassembly can be provided in sterile condition (for example, in sterile packaging). The pump/injector 100" and container 50" can be disposable after a single use. Pump/injector 100" can also be sterilizable to provide for multiple uses. Sterile barriers can also be used in connection with nonwearable embodiments of pump/injector 100" and other injectors of the present invention.

The system subassembly of pump/injector 100 and syringe 50 and other system components can, for example, be made to be MR compatible for use in an MR environment as described, example, in U.S. Pat. No. 5,494,035, Published PCT International Patent Application Nos. WO 02/082113 and WO 03/006101, and U.S. patent application Ser. No. 10/916,946, filed Aug. 12, 2004, now U.S. Pat. No. 7,315,109 the disclosures of which are incorporated herein by reference, as well as in other imaging system environments.

As illustrated in FIG. 9D, the system subassembly of pump/injector 100 and syringe 50 can be attached to the user with an attachment mechanism such as a simple adjustable armband or other strapping 1460. Strapping 1460 can, for example, include a hook-and-loop type fastener such as VELCRO® or other fastening mechanism as known in the fastening arts. Upon attachment of the subassembly to the forearm of the user, a set of controls located on device 100" preferably faces "upward" toward the user's eyes while in use. The proper orientation of displays and nomenclature facilitates use by both right- and left-handed users. With a clear view of the display on the forearm unit, the user has ready access to and knowledge of the variety of functional parameters of the device, reducing the possibility of error or miscalculation.

As illustrated in FIG. 9E, information displayed on one or more displays of the forearm unit can, for example, be clearly readable from up to 30" and provides continuous indication/feedback to the user of, for example: injections remaining; injections made; dose volume; volume remaining; volume injected; injection in progress; injection complete; device status, battery power injection etc.

Figure 9F:
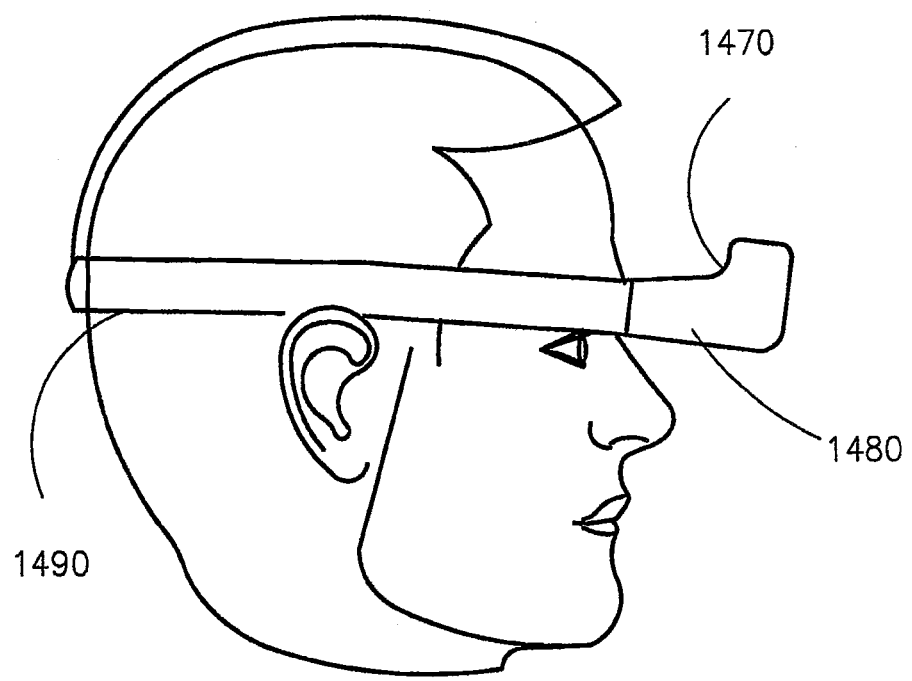
FIG. 9F illustrates an embodiment of a head mounted display for use in connection with the injection systems of the present invention.

Information/feedback to the user can alternatively or additionally be provided using a display mounted to remain in the user's field of vision. By placing pertinent information in the user's view at all times, the user may consult the information without taking the user's eyes off of the procedure at hand. In the embodiment of FIG. 9F, for example, a display 1470 in communicative connection with injector system 100" is mounted on a frame or support 1480 attached to a headband 1490 worn by the user.

In-line Measurements/Sensor Feedback/System Control Architecture

A. Patient Physiological Parameters

In one embodiment of the present invention, patient interface 400 includes or has in operational connection therewith one or more physiological measurement devices, systems or function. For example, such devices can determine the location of damaged tissue, such as ischemic and infarcted areas of heart tissue.

Biosense-Webster, a J&J/Cordis subsidiary, has, for example, developed a system to create functional maps of cardiac electrical and mechanical activity using catheter-mounted electrodes. That NOGA catheter is used in the cath lab to determine the location of ischemic and infracted areas of the endocardial wall. It is useful in assessment of treatment, since ischemia is caused by reduced oxygen delivery to cardiac muscle, and can be corrected by procedures that restore blood flow, while infarction is associated with unrecoverable dead tissue. Implantation of cells would follow different strategies based on the diagnosis of ischemia versus infarct.

In the NOGA system, the location of the contacting electrodes is tracked in real-time by a standard electromagnetic tracking system. Data is used by a computer to create maps of the cardiac activity. Data can be sampled from inside the heart (see following) or from the outside using catheters or sensing needles.

U.S. Pat. No. 6,892,091, the disclosure of which is incorporated herein by reference, discloses a catheter capable of mapping the electrical and mechanical activity of the heart by sampling the voltage and mechanical strain at unique points on the endocardium. A three-dimensional color-map of the activity is created by associating data with a location of the sampled tissue determined by electromagnetic tracking of the catheter tip.

Another way of monitoring ischemia or hypoxia in cardiac tissue is through the use of catheter-mounted or needle-mounted oxygen probes. These devices are electrochemical devices mounted in or upon invasive devices that make contact with tissue. These devices are capable of responding to the partial pressure of oxygen present in and around perfused tissues. Several commercial devices are available from Oxford-Optronix of the Oxford, United Kingdom.

In several embodiments of the present invention a therapeutic device is coupled with a diagnostic device to inject therapeutic fluids, cells, cell carriers (including, for example, beads), for example into sites of damaged heart tissue. As illustrated, for example, in FIG. 3, system 5 can, for example, include: (1) patient interface 400 (e.g. catheter or needle) to inject therapeutic fluids, emulsions, suspensions, gels, solids etc. into tissue as described above; (2) one or more sensors, measurement devices or monitors 600 (for example, mounted in or upon the patient interface 400 or otherwise placed in operative connection with the patient) to measure one or more biophysical properties of the patient and/or the patient tissue; (3) one or more imaging systems 500 to display regions of the patient (for example, ischemia or infarction distinguishable from healthy tissue); and (4) a feedback system by which an operator can use imaging system 500 to guide patient interface 400 (for example, with sensor(s) as described above) to a region of damaged tissue (for example, ischemic tissue) to inject therapeutic fluids, cells, or cell carriers The sensing device(s) can, for example, make direct contact with the tissue to distinguish among well-perfused, or infarcted (dead) or ischemic (stunned) tissue, presuming that injection into ischemic tissue is more likely to restore function to the affected area. Based on the measurement, system 5, through control system 200, can allow or disallow the injection. Preferably, system 5 at least alerts or informs the operator of the tissue condition prior to delivery of a therapeutic fluid.

System 5 can also include a measuring or sensing device to detect the amount of blood flow or capillary perfusion in tissue. In one embodiment, the sensor makes direct contact with the tissue and responds rapidly to change in blood volume in a perfused tissue. One example of such a device is a thermistor, which is sensitive to rapid changes in blood volume as indicated by temperature change at the contact point. The thermistor changes its electrical conductivity in response to small temperature differences. Sensitivity of the measurement can be increased by using a pair of thermistors with one serving as a reference.

In another embodiment, the measuring or sensing device is a contacting or a non-contacting infrared light source and an infrared sensor arranged as a pair. This sensor pair responds to small changes in blood perfusion by sensing reflected and scattered light in tissue. Highly perfused tissues are easily distinguished from ischemic or infarcted tissues because of the optical properties of blood with respect to the scattering and absorption of infrared light. This principle is known in the art (see, for example, U.S. Pat. No. 6,122,536, the disclosure of which is incorporate herein by reference), but sensing systems that probe perfusion of tissue on percutaneous medical devices are unique.

To position the sensor residing near the distal tip of patient interface 400 (for example, a catheter, needle, or endoscope), an additional miniaturized device can be provided to determine the sensor location with respect to the tissue under treatment. The location of the sensor can then be superimposed upon the image of the tissue displayed for the operator by imaging system 500. A medical positioning system of this type is described, for example, in U.S. Pat. No. 5,526,812, the disclosure of which is incorporated herein by reference. That system uses an electromagnetic field and multiple antenna loops to sense the field and to triangulate sensor position for processing by a computer graphics system. As described above, the present invention can provide a map of, for example, blood perfusion in tissue in near real-time prior to the administration of therapy.

Physiological parameters such as respiration and/or heart function can also be measure to, for example, provide a positioning function, a gating function or an injection timing function. For example, FIG. 3 illustrates the use of an electrocardiogram (EKG) which can be used to measures heart movement and synchronize injection. In this system, control system 200 is in operative connection with the EKG monitor (for example, part of monitor system 600), which measures the heart's activity. Control system 200 uses that information to control pump system 100 and/or patient interface 400 to, for example, deliver fluid when the heart muscle is relaxed (during diastole), enabling greater fluid delivery and distribution.

Marking and Mapping During Delivery

In several embodiments of system 5 marking of delivered injectate and mapping of tissue regions is provided. During the injection procedure, one goal of marking is to enable the doctor or operator to determine what tissue has been treated, both to avoid double treatment and to ensure sufficient coverage of the area to be treated. Marking also helps provide uniformity of treatment over the tissue surface, with the option of quantifying the treatment in two or three dimensions. These results are especially useful in external heart treatments and dermatological treatments. The marking can be such that it is used long term to monitor tissue response or cell migration. An ancillary benefit is that some of the marking mechanism can optionally help keep the injectate in the tissue.

One set of marking embodiments marks the surface of the tissue being treated, to indicate the location of the needle puncture or an approximation to the spread of the injectate within the tissue as or after the injection occurs. These markings may be visible to the eye, (either unaided or aided) such as dyes applied by a "rubber stamp" type applicator of U.S. Pat. No. 5,997,509, the disclosure of which is incorporate herein by reference. U.S. Pat. No. 6,322,536, the disclosure of which is incorporate herein by reference, discloses sutures or other surface mechanical devices. Embodiments also include the deposition of powders or foams through, for example, a second delivery channel as described above. Biodegradable solid segments can also be beneficially used as markers, with the added benefit of sealing the wound. Adhesive dots of tissue scaffolding material are one option. Gels or solid barbed pins, optionally filling the needle tract to reduce back flow, are another option. The applicator or patient interface itself can create a mechanical mark. It can, for example, use vacuum to hold the tissue being injected, thereby raising a small bleb. The hole made during the injection can bleed, and the bleeding or clotting can act as a mark. Alternatively or additionally, the process of touching the tissue surface can roughen the surface, providing visual indication. Further, a small region of tissue can be cauterized, possibly cauterizing the injection site itself, providing both marking and sealing the tissue to reduce injectate leakage. Devices for augmenting the operator's vision include endoscopes or thoracoscopes, microscopes, and cameras which can be sensitive to visible or non-visible electromagnetic radiation. Fluorescence can also be used beneficially, where the output of the marker is in the visible range as it is excited by a possibly more intense light at a higher invisible wavelength.

Another marking approach is to mark the injectate itself. This has the benefit of allowing 3D visualization of the injection if an imaging system of some type is used. An injectate rich in water can, for example, be differentiated from many tissues using MR imaging. Addition of imaging contrasts—for example, ultrasound, X-ray/CT, or MR contrast to the injectate—can improve visualization by the respective imaging modalities. A radioactive component or PET tracer could be added to the injectate or to cell surface for imaging via nuclear medicine. Published U.S. Patent Application No. 2003/219385A1 and Published PCT International Patent Application No. WO 2005/072780A2, the disclosures of which are incorporated herein by reference, disclose two methods for marking cells so that it is possible to monitor cell proliferation and/or migration after the delivery as well as the delivery process itself. Alternatively, the cells being marked can be non-active cells so that their only use is to transport the marker. The marker could be in separate particles that could be solid, liquid, for example in liposomes or solid shells, or gaseous particles such that they are visible under one or more medical imaging modalities.

The marking process can involve a reaction during the injection. For example, injecting an alginate and the calcium salt solution required for polymerize enables a liquid to be delivered and a solid to be formed in the tissue. An alternative is to have the reaction be between the marking device and the tissue. An example is a marker that changes color or imager contrast properties upon exposure to air, water, or a specific pH, such as present in commonly available pH indicators. Alternatively, the injectate can cause a quick physiological response, similar to a mosquito bite, with the resulting bump indicating the injection site.

If a computer based system is used to visualize or augment the visualization, then one of several virtual marking systems can be used. One embodiment of such a device or system incorporates an electromagnetic field position measuring system. Commercial or research systems are available from a number of manufacturers (Endocardial Solutions (EnSite 3000), Biosense Webster/J&J (CARTO XP, NAVI-STAR catheter), Medtronic (LocaLisa), Boston Scientific (RPM Realtime Position Management System)). By measuring the 3D position of the injection effector when an injection is given, a 3D model can be built and displayed to the operator.

In another embodiment, a virtual marking system can be used if, for example, an endoscope or thoracoscope with a camera is used. Using scene recognition algorithms similar to those used to place the virtual first down lines on the football field, every time an injection occurs, the imaging system can mark or color that segment of tissue, providing a virtual ink mark on the surface.

As an alternative to tracking the actual injection sites, the marking system can lay down a grid or pattern that the user is to follow. In one embodiment this is a physical grid, such as might be applied with ink or a label. Alternatively, the markings can be "painted" or drawn in real time onto the tissue, for example with light or laser. The markings can be static, or dynamic, for example moving or changing as the user performs an injection to indicate where the next injection should take place. A similar guidance capability can be achieved virtually using a computer and an image display mentioned above.

The computer guidance systems described above can be connected to a robotic system (for example, including patient interface positioning system 460) to automate the delivery. Such automation may be of particular value when a very large number of injections are required (as in certain dermal implanting procedure as discussed above).

For many advantages, the marking is considered only during the delivery process. However, there can be a benefit to verifying injectate delivery in the time frame of hours, days, weeks or months. The more permanent marking schemes described, such as solid particles or solid surfaces, can provide verification of delivery at any time. Biodegradable markers can be used to provide marking for a desired time, and then degrade to reduce or eliminate any deleterious biological effects.

For those markers that are not part of the injectate, there can be a second pump and fluid path to deliver the marker to the tissue surface or the tissue depth. The marker and therapeutic injectate can be delivered through the same needle, with the marker going before, simultaneously, or after the therapeutic injectate. An example of the later is a polymerizing marker that also acts as a plug to reduce leakage through the injection site. A fluid marker can be delivered through a second independent fluid path, either to the surface or into the tissue. For delivery into the tissue, delivery can, for example, be through a needle, a high pressure jet, a cutting edge, or a roughing surface.

A mechanical marker can, for example, be mounted on a depth stop as described above or mechanically associated with an injectate effector as described above.

Information Encoding

Maintaining traceability of cells and ensuring that they are delivered for their intended purpose is one of the challenges facing cell therapy providers. In several embodiment of the present invention, cell container 50, the injection fluid and/or the cells are encoded with information such as batch, date of manufacture, processing and/or harvest, and target patient. System 5 preferably includes a sensor or reader that is capable of reading the encoded information. Encoding of syringes/container and sensors used to read such information are, for example, discussed in U.S. Pat. Nos. 5,383,858, 6,652,489 and 6,958,053 and PCT Published International Patent Application Nos. WO 99/65548, WO 02/056934, and WO 02/081011, the disclosures of which are incorporate herein by reference. The injection fluid can, for example, be encoded by providing a detectable and distinguishable characteristic (for example, color). One or more physical and/or chemical identifying markers or tags can also be added physically or chemically attached to the injection fluid molecules or to the cells themselves.

In one embodiment, patient information can be entered into control system 200 before cell-containing container or cartridge 50 is inserted. Upon insertion of container 50, the control system 200 (including, for example, a sensor or reader on pump/injector system 100) "reads" the encoded label and verifies that the patient information on container 50 matches the input information.

The above methodology can, for example, be particularly helpful in procedures involving autologous stem cells or cells that have been removed from a patient, processed, and then implanted as an assurance that the patient's own cells, and not another patient's calls, are being injected.

Encoding of cell container 50 can also include information about how the cells should be handled and maintained by system 5 such as mixing speed, temperature, and or maximum injection speed. Cell therapies requiring buffers and other solutions to be mixed with them can provide this information to the fluid handling system through encoding.

Another area in which encoding is useful is ensuring traceability of the therapy itself. Pharmaceutical companies preferably take steps to ensure that the therapy is used in the intended way and not misapplied. Verification of this use can be important. Encoded information can, for example, be returned to the manufacturer as verification of proper use.

Processing of Cells Prior to Delivery

Cells can, for example, be stored and/or delivered in a transport or hibernation buffer solution as known in the art. An example of cells delivered in a hibernation fluid is SPHERAMINE. As described above, SPHERAMINE is formed of dopamine-producing human retinal pigment epithelial (RPE) cells adhered to spherical microscopic carriers. SPHERAMINE can, for example, be implanted into the regions of the brain that lack dopamine, where it produces dopamine in place of the patient's own neurons which can no longer perform this function.

In current procedures for the injection of SPHERAMINE, approximately 1 ml of RPE cells on the spherical microcarrier is, for example, transported and delivered with 3 ml of a hibernation or transport buffer solution in a 5 ml CYROVIAL®. In general, Cryovials are tubular containers or vials designed for storing and/or preservation biological materials (for example, at low temperatures) and are available from many suppliers including Simport Plasiques LTEE Corporation of Quebec, Canada. Before injection of SPHERAMINE, the hibernation solution is removed and the cells are washed to remove remaining hibernation solution. In a typical procedure, the SPHERAMINE is allowed to settle to the bottom of the cryovial. Using, for example, a syringe, the transport solution is withdrawn by drawing down the fluid level to approximately the level of the SPHERAMINE (that is, to the 1 ml level).

A buffer solution such as Hank's Balanced Saline Solution (HBSS) is then mixed with the SPHERAMINE to dilute the remaining hibernation solution. In that regard, after the SPHERAMINE is allowed to settle to the bottom of the vial, the HBSS is drawn down to the level of the SPHERAMINE.

Figure 10A:
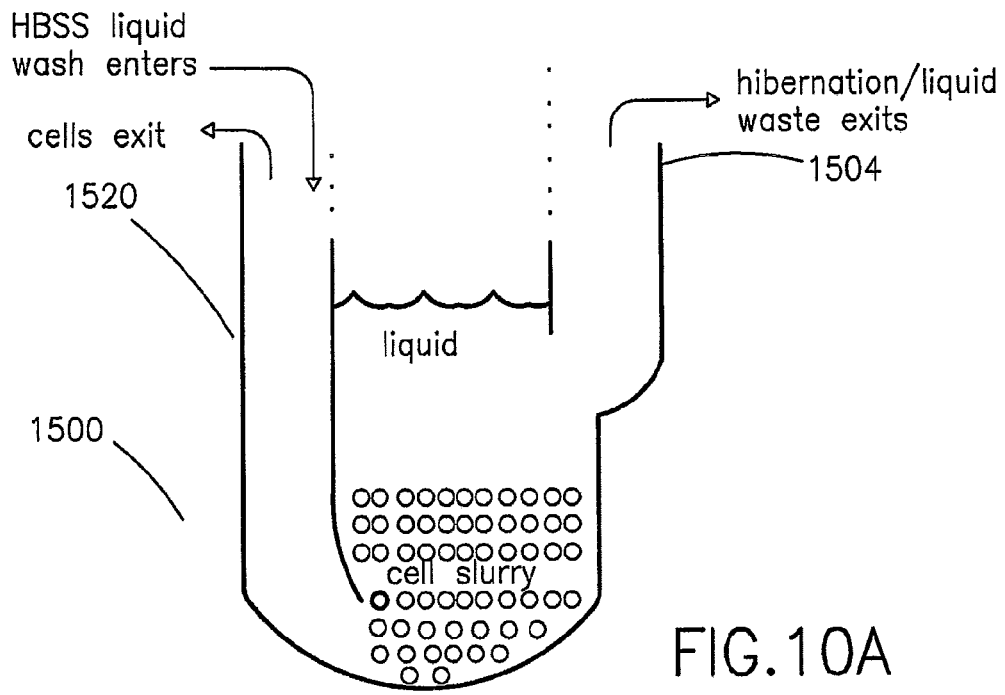
FIG. 10A illustrates an embodiment of a transport and/or storage container of vial of the present invention adapted to effect cell washing and/or buffer replacement.
Figure 10B:
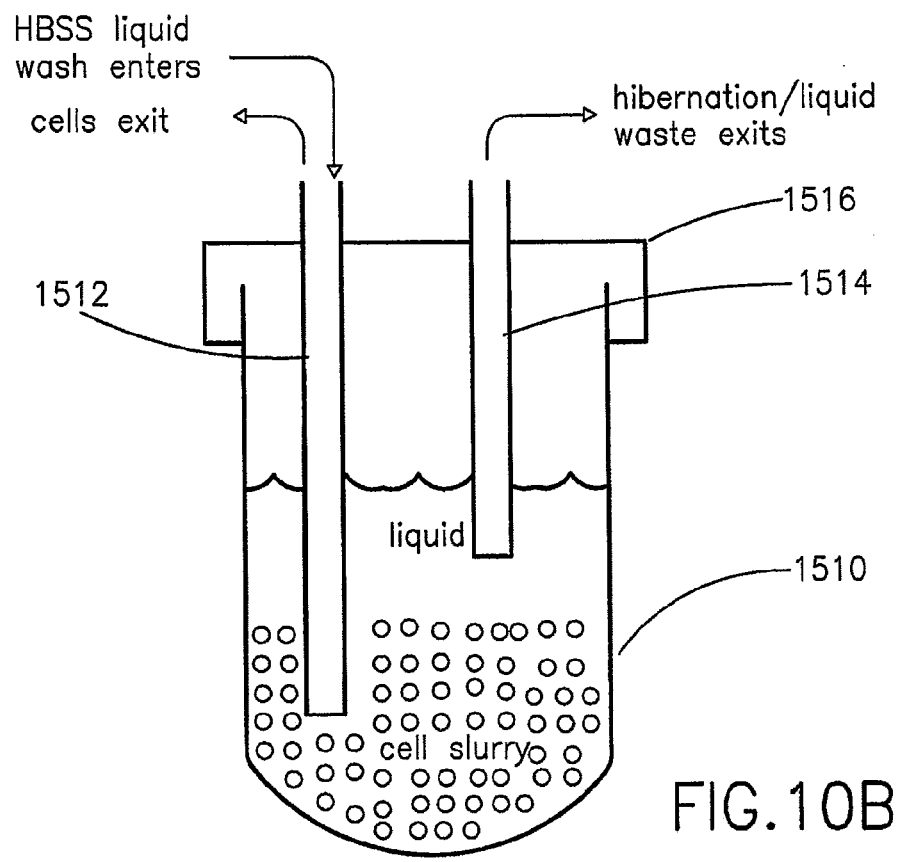
FIG. 10B illustrates another embodiment of a transport and/or storage container of vial of the present invention adapted to effect cell washing and/or buffer replacement.

Current equipment and manual techniques used in cell preparation (for example, washing, buffer replacement and/ or other fluid treatments) can, for example, lead to cell wastage and/or contamination. FIGS. 10A and 10B, for example, illustrate two embodiments of containers or vials that can facilitate the preparation of cells for delivery. In each of these embodiments, two tubes extend to different depths into the vial containing the cell slurry. In the embodiment of FIG. 10A, tubes 1502 and 1504 are formed as part of the vial 1500. In the embodiment of FIG. 10B, tubes 1512 and 1514 are built into or placed in operative connection with a cap 1516 that covers vial 1510. The tube (or other port) that extends or is positioned to a higher level within the vial (tubes 1504 and 1514 on the right side of each of vials 1500 and 1510, respectively in FIGS. 10A and 10B) is operable to remove the liquid without disturbing the cell slurry that has been allowed to settle to the bottom of the vials. The tube (or other port) that extends or is positioned to a lower level (tubes 1502 and 1512 on the left side of each of vials 1500 and 1510, respectively in FIGS. 10A and 10B) is operable to introduce a buffer or washing solution such as HBSS and to remove cells for injection into a patient.

During use, transport or hibernation fluid can first be withdrawn from the higher level tube without disturbing the settled cells. HBSS is then introduced through the lower level tube to wash through the cells. After settling, waste fluid is then withdrawn through the higher level tube. Then, cells are withdrawn via the lower level tube for injection into the patient. Among other benefits, the devices of FIGS. 10A and 10B eliminate the need to position a syringe just above the cell slurry during the washing step, reducing the amount of operator skill and time it takes to perform the washing step. This technique is also more adaptable to closed operation than is manual pipetting, as is discussed elsewhere herein.

Figure 10C:
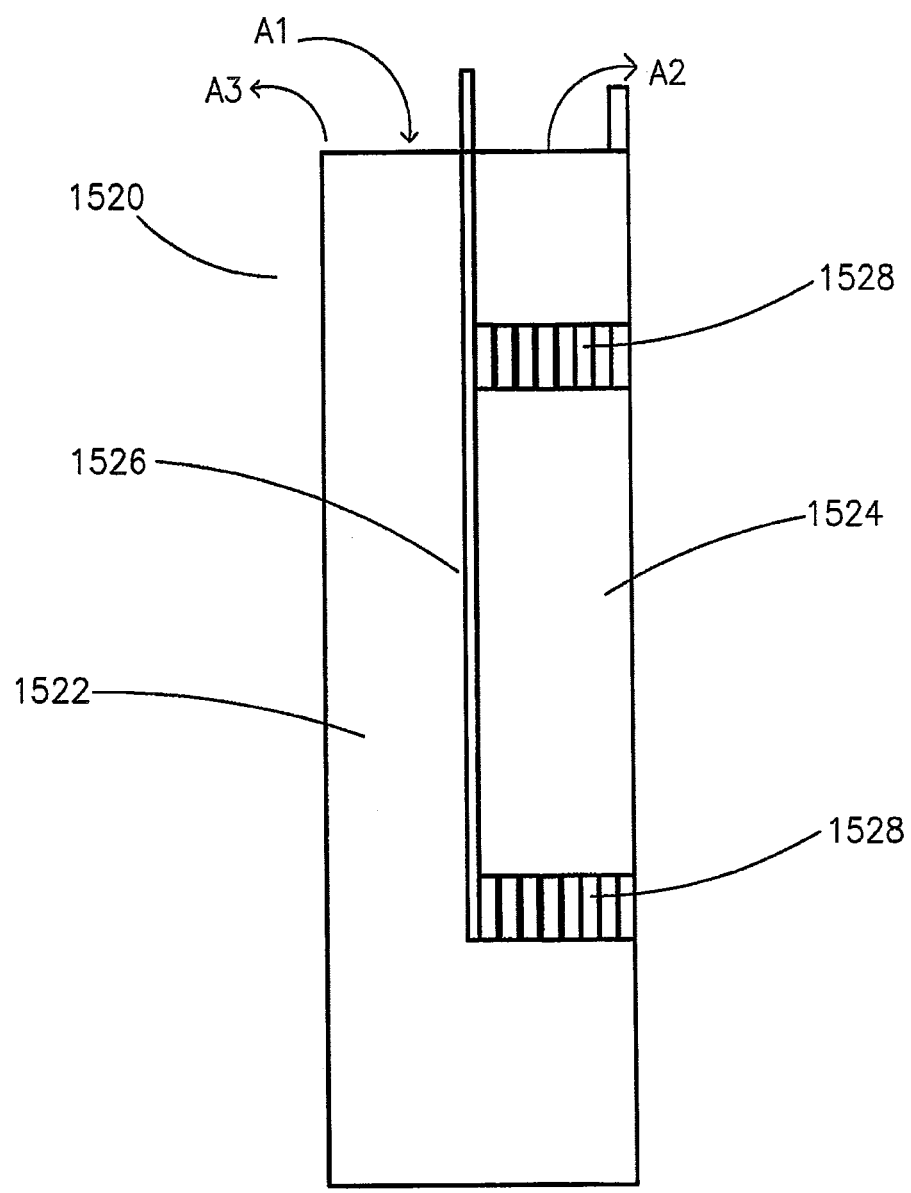
FIG. 10C illustrates another embodiment of a transport and/or storage container of vial of the present invention adapted to effect cell washing and/or buffer replacement.
Figure 10D:
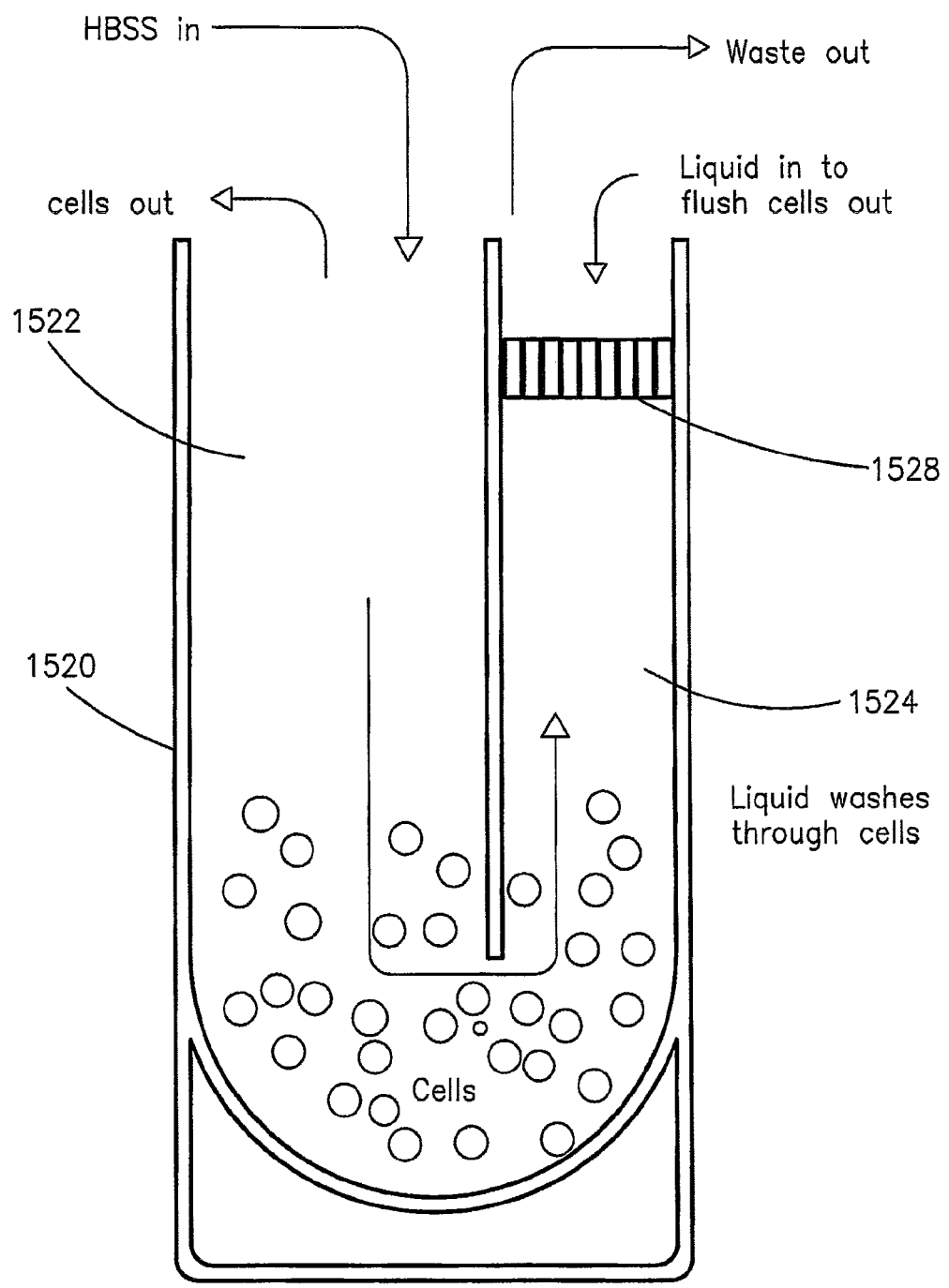
FIG. 10D illustrates the vial of FIG. 10C with a rounded bottom portion.

FIGS. 10C and 10D illustrate other embodiments of containers or vials that can facilitate washing of cells. FIG. 10C illustrates a cryovial 1520 that is divided at generally the center thereof into a left side or region 1522 and right side or region 1524 over a portion of the length of cryovial 1520 by a divider 1526 extending downward (in the orientation of FIG. 10C) from the top of vial 1520. A filter or filters 1528 can be placed either at position A or position B (see FIG. 10C) on right side 1524 of the cryovial. Filter(s) 1528 is/are adapted to allow liquid to pass therethrough but to prevent passage of, for example, SPHERAMINE therethrough. Such a device can, for example, be used with any cells or other structures having a minimum size large enough to be excluded from passage through filter(s) 1528. Flow of HBSS into cryovial 1520 is represented by arrow A1, whereas flow of waste liquid out of cryovial 1520 is represented by arrow A2. As represented by arrow A3, cells (for example, SPHERAMINE) can be extracted from unfiltered left side 1522 of cryovial 1520 or flushed out of cryovial 1520 by introducing HBSS (or other fluid) into right side 1524 of the cryovial 1520. As illustrated in FIG. 10D, the bottom of cryovial 1520 can be rounded to facilitate flow through cryovial 1520. The embodiments of FIGS. 10C and 10D, consolidate tubing by using cryovial 1520 as the wash container.

Figure 10E:
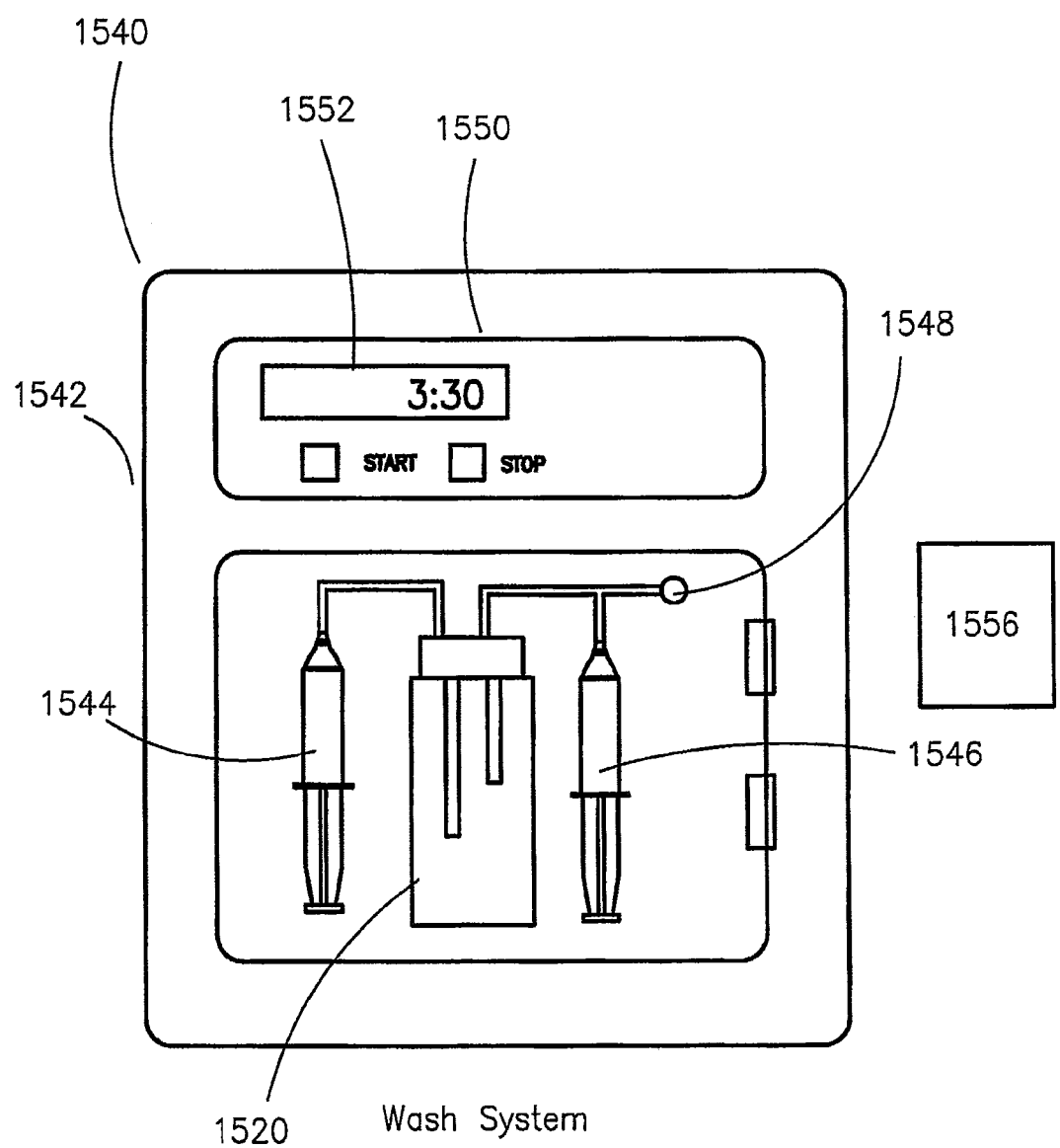
FIG. 10E illustrates an embodiment of a closed system of the present invention suitable to effect cell washing and/or buffer replacement.

The embodiments described above and other embodiments of storage, transport and/or washing devices of the present invention can be used with systems that include a syringe and/or other pumps to, for example, add HBSS, withdraw waste materials, withdraw cell etc. One embodiment of such a system is illustrated in FIG. 10E. System 1540 of FIG. 10E includes a closable cabinet 1542 or other enclosure that accepts, for example, a modified cryovial 1520 as described above, as described in connection with FIG. 10F below, or another container. In the illustrated embodiment, syringes 1544 and 1546 are used to effect flow within and out of system 1540. A sample port 1548 is provided for a fluid sample to exit the system. System 1540 can further include fluid path connectors to connect to ports/tubes on the top of cryovial 1520 or needles to pierce a septum on the top of, for example, vial 1560 of FIG. 10F. A control system 1550 can be provided that can display information related to the status of the system via, for example, display 1552. In that regard, FIG. 10F illustrates an embodiment of cryovial 1560 having a pierceable septum 1562 suitable for use with an embodiment of a system of FIG. 10E including one or more piercing needles 1554 and 1556 (in the illustrated embodiment).

In general, the vial remains in cabinet 1542 of system 1540 while fluids are circulated and withdrawn from the vial for wash cycles, dilution, or sampling for an assay test. In that regard, one or more assay testing devices 1556 (see FIG. 10E) can also be contained in the cabinet or otherwise be placed in operative connection with system 1540 (for example, using cell or particle counting technologies, such as a coulter counter or an optical counter). In this embodiment, syringes 1544 and 1546 can be large enough to contain all the initial wash solution and all the withdrawn waste solution. One or more valves can also be provided to assist in controlling flow as known in the art.

System 1540 can be programmable, and can also include timers for indicating the status of various processes such as a wash/dilution cycle and/or to indicate when the vial is ready for removal. Moreover, system 1540 can also be used as an "auto-loading" device to, for example, automatically fill a cartridge or syringe. The cartridge or syringe can then be placed into operative connection with an injector or other fluid delivery system for administration of the cell therapy to the patient. In one embodiment, system 1540 keeps track of vial contents, processing, etc. System 1540 can also create encoding devices including, but not limited to, labels, barcodes, or RFID tags, for the vial to assist with tracking or indication of viability, concentration, time of preparation, and/or other information related to the status or condition of the contents of the vial or prepared dose.

Figure 10F:
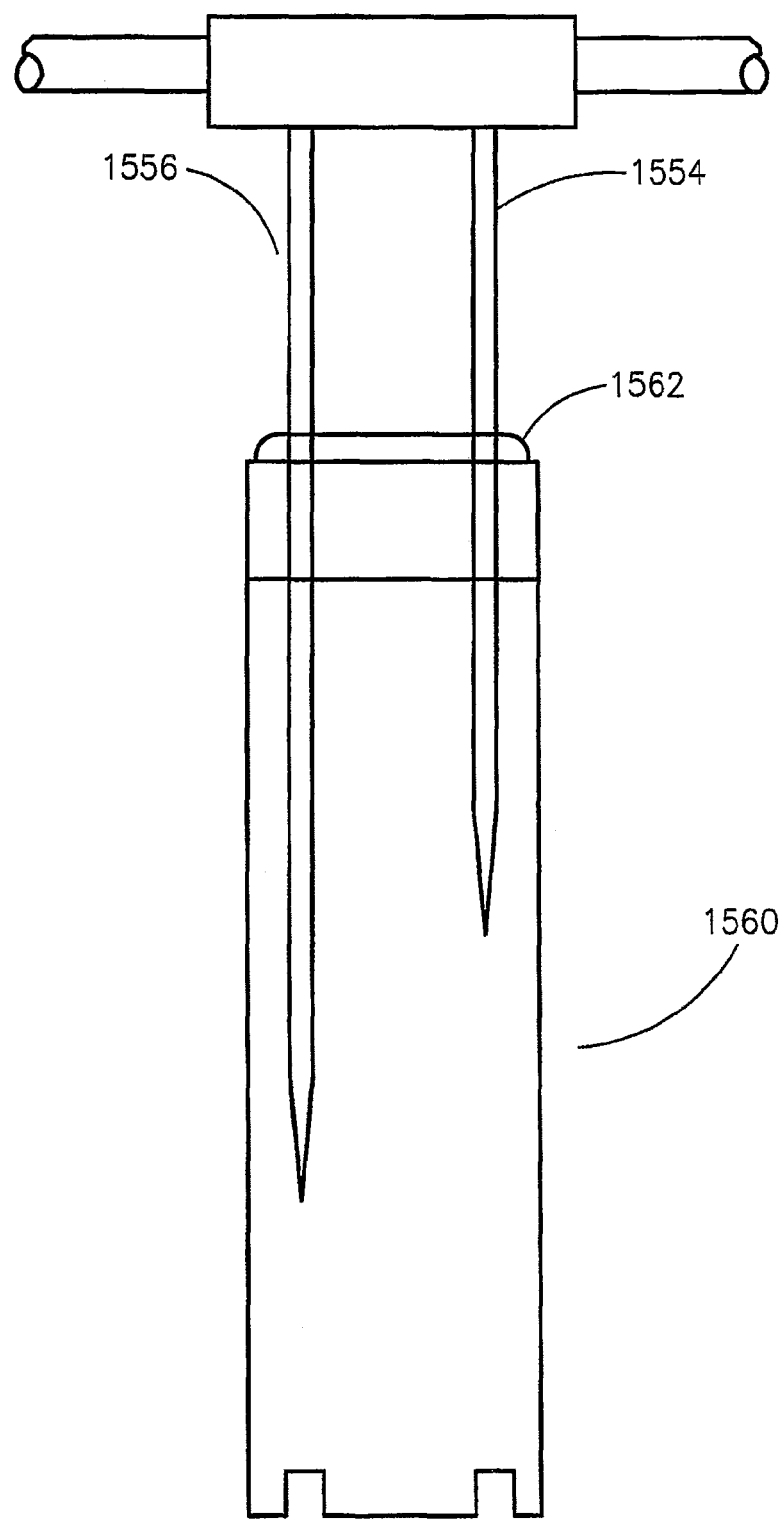
FIG. 10F illustrates another embodiment of a transport and/or storage container of vial of the present invention adapted to effect cell washing and/or buffer replacement and including a pierceable septum.

FIG. 10F illustrates two needles of different length piercing pierceable septum 1562 of vial 1560. As described above, for example, in connection with FIG. 10A and 10B needles 1554 and 1556 can be of different lengths so that the shorter needle 1554 can, for example, be used to remove hibernation solution or media and/or waste, while longer needle 1556 can, for example, be used to introduce HBSS or other fluid to effect washing or dilution and/or to remove cells.

Figure 11A:
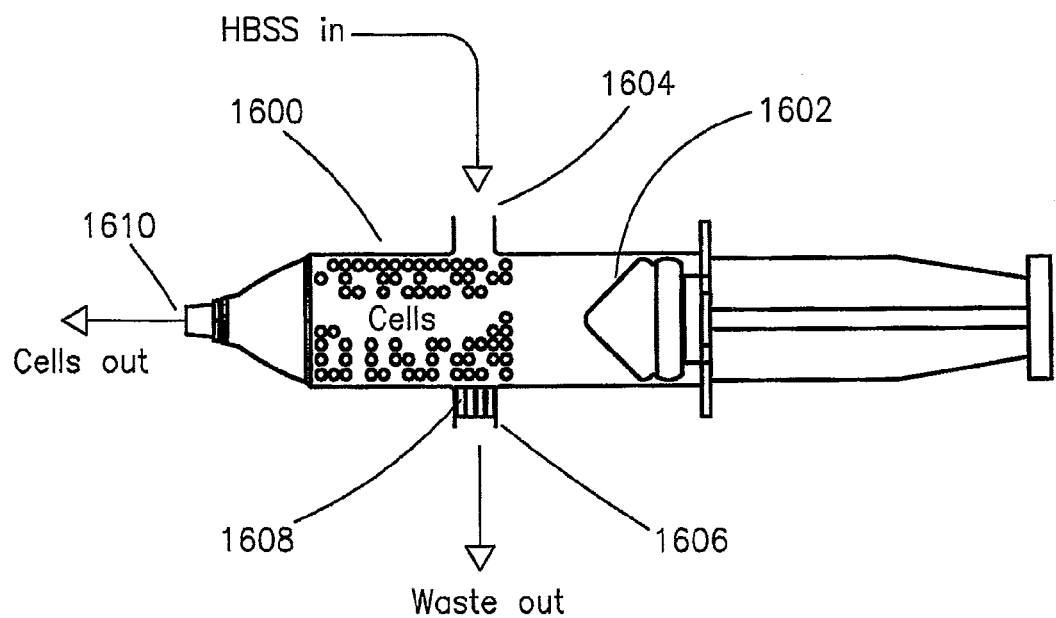
FIG. 11A illustrates an embodiment of a devices of the present invention adapted to effect cell washing and/or buffer replacement and cell injection.

In several other embodiments of the present invention, systems are provided in which, for example, washing and dilution can be effected using a single device. Such devices can also form a part of the cell therapy delivery device or the entirety thereof. For example, FIG. 11A illustrates a syringe 1600 including a syringe barrel having a plunger 1602 slidably movable therein to draw fluid into the syringe barrel. In this embodiment, a first port 1604 is provided (for example, on the side of the syringe barrel) through which a fluid such as HBSS can flow into syringe 1600. A second port 1606 is provided (for example, on the side of the barrel) through which waste can be removed from syringe 1600. A filter 1608 is placed in operative connection with second port 1606 so that cells and/or other materials to be injected are prevented from exiting syringe 1600 through second port 1606. Cells can be injected via an outlet port 1610 or syringe tip on the forward end of syringe 1600. Valves (not shown) as known in the art can be provided in connection with one or more of the ports of syringe 1600 to control flow.

Figure 11B:
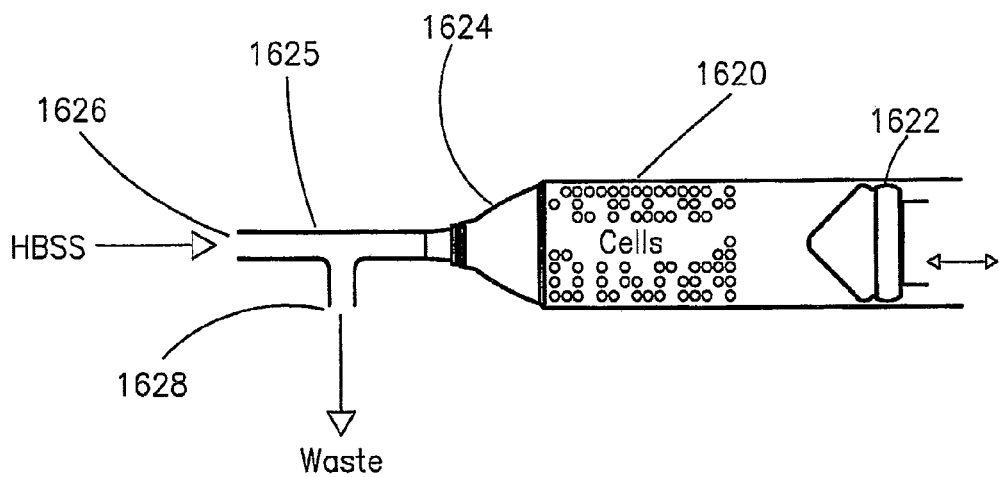
FIG. 11B illustrates another embodiment of a devices of the present invention adapted to effect cell washing and/or buffer replacement and cell injection.
Figure 11B:
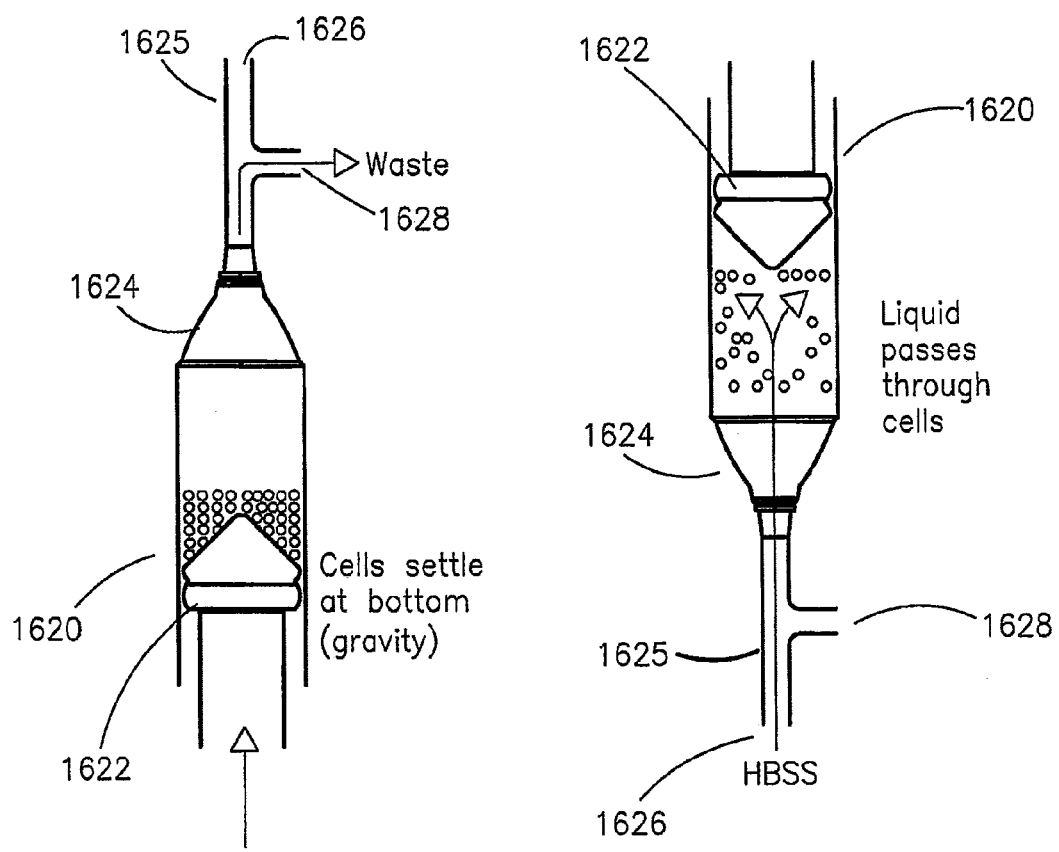

FIG. 11B illustrates another embodiment of a syringe system of the present invention. In this embodiment, syringe 1620 includes a syringe barrel having a plunger 1622 slidably disposed therein. A generally conical shaped transition region 1624 on a forward end of the syringe barrel connects to a neck 1625 which includes an outlet port 1626 at the forward end thereof. A second port 1628 is provided (for example, on the side of the neck). Second port 1628 or side port can be formed integrally or monolithically with syringe 1620. Alternatively, a fluid path section including an injection outlet port and a second port or can be added via an attachment to a standard syringe in forming the system of FIG. 10B.

The syringe of FIG. 11B can, for example, make use of gravity to separate cells from liquid. When expelling waste via side port 1628 in syringe neck 1625, syringe 1620 can be oriented upward as shown in the bottom left of FIG. 11B. In this orientation, the cells settle to the rearward portion of the syringe barrel. The liquid is ejected from the top as plunger 1622 is slowly advance forward (toward syringe outlet port 1626). When washing cells with, for example, HBSS syringe 1629 is oriented as shown on the bottom right of FIG. 11B. In this orientation, the cells settle to the forward portion of syringe 1620. HBSS or other fluid can then be drawn into syringe 1620 by drawing plunger 1622 rearward (away from syringe outlet 1626). Drawing the liquid into syringe 1620 in this manner causes the liquid to flow through the cells (for example, SPHERAMINE). Appropriate valves as known in the art can be placed in fluid connection with syringe outlet port 1626 and second or side port 1628 to control flow therethrough. The syringe system of FIG. 11B isolates the cells within syringe 1620, reducing the possibility of contamination. Additionally, syringe 1620 can be a part of or can form the entirety of a delivery device as, for example, described above.

Figure 11C:
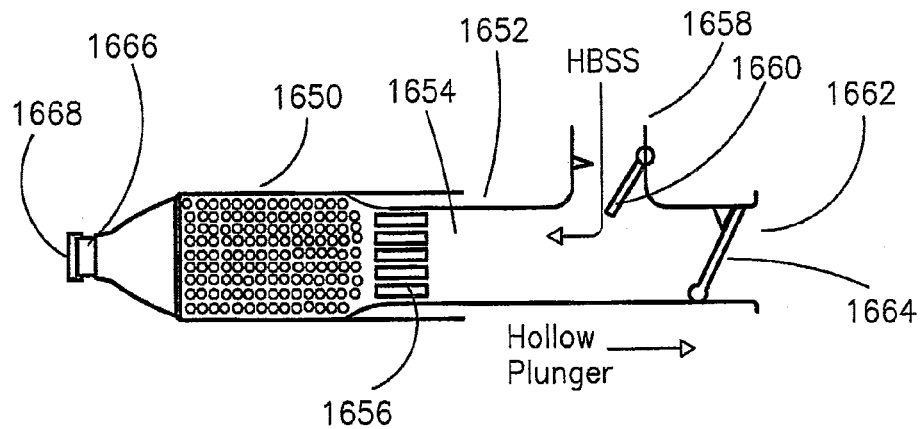
FIG. 11C illustrates another embodiment of a device of the present invention adapted to effect cell washing and/or buffer replacement and cell injection wherein buffer is being drawn into the device.
Figure 11D:
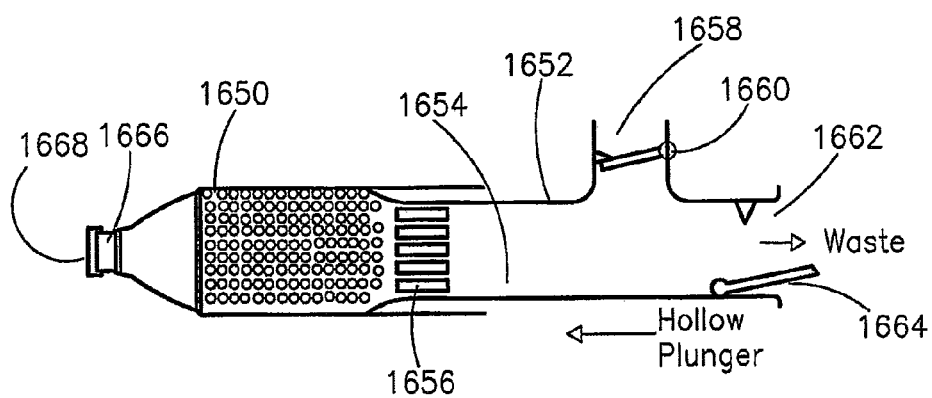
FIG. 11D illustrates the device of FIG. 11C wherein waste is being expelled from the device.
Figure 11E:
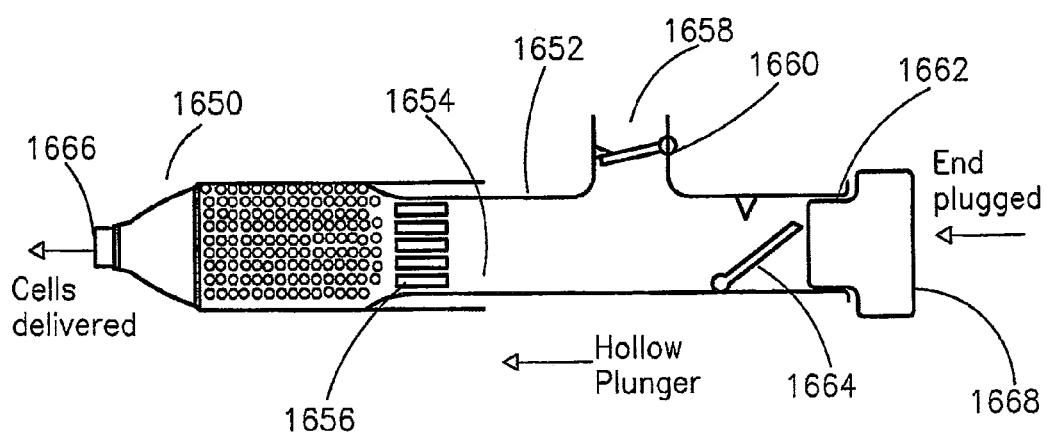
FIG. 11E illustrates the device of FIG. 11C wherein cells are being delivered from the device.

FIG. 11C through 11E illustrate an embodiment of a syringe 1650 of the present invention including a plunger 1652 having a volume or chamber 1654 formed therein or in fluid connection therewith. Plunger 1652 interfaces with the fluid within syringe barrel via a filter 1656, which can be considered as partially replacing the rubber cover commonly used on the forward end of conventional plungers. Holes, pores or other transport paths of filter 1656 are sized such that liquid may pass though, yet cells (for example, SPHERAMINE) cannot. Plunger chamber 1656 has in fluid connection therewith an inlet 1658, including an inlet valve 1660, and an outlet 1662, including an outlet valve 1664 as illustrated in FIGS. 11C through 11E. Valves 1660 and 1664 can, for example, include one-way check valves.

In a representative example of use of syringe 1650 of FIGS. 11C through 11E, syringe outlet 1666 on the forward end thereof is first capped with a cap 1668 and plunger 1652 is drawn back, introducing HBSS into the plunger chamber 1654 (via inlet 1658) and through filter 1656 to contact cells held within the syringe barrel forward of filter 1656 (see, FIG. 11C). In a second step illustrated in FIG. 11D, plunger 1652 is pushed forward, forcing waste to exit outlet valve 1664 in fluid connection with plunger chamber 1654. The above steps can be repeated to thoroughly wash the cells. In a subsequent step illustrated in FIG. 11E, cap 1668 is removed from syringe outlet 1666 and outlet 1662 in fluid connection with plunger chamber 1654 is plugged or capped with a plug 1668. Upon forward advancement of plunger 1652, the cells are expelled from syringe outlet 1666.

The syringe of FIGS. 11C) through 11E (as well as those of FIGS. 11A and 11B) can include a sterile bag to contain the syringe. As with the syringes of FIGS. 11A and 11B, syringe 1650 of FIGS. 11C through 11E isolates the cells in the syringe, reducing the possibility of contamination. Also, syringe 1650 can form part of or the entirety of a cell delivery system.

Figure 11F:
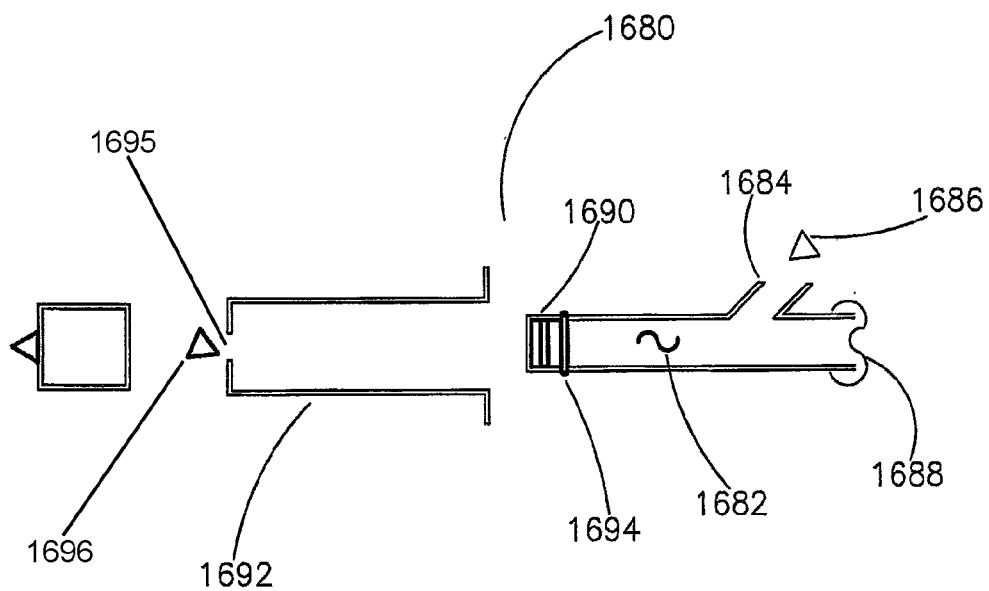
FIG. 11F illustrates another embodiment of a device of the present invention adapted to effect cell washing and/or buffer replacement and cell injection wherein buffer is being drawn into the device.

FIG. 11F illustrates another embodiment of a device or system 1680 for use in connection with a cell therapy such a SPHERAMINE to provide a closed system to wash and to deliver cells. Device 1680 can be used with any structure to be injected, including cell structures, that can be size excluded via, for example, a micropore filter.

Device 1680 includes a cell chamber or transport vial 1682 that includes a mechanism or fluid path to flush buffer solution (for example, HBSS) through chamber 1682 while retaining the cells in chamber 1682. In the embodiment illustrated in FIG. 11F, cell chamber 1682 includes an inlet port 1684 through which a flushing buffer can be introduced into cell chamber 1682. A one-way check valve 1686 can be placed in fluid connection with inlet port 1684. A septum 1688 can cover a first end of cell chamber 1682. A filter 1690 covers the second end of the cell chamber 1682. Cell chamber 1682 is insertable within a housing section 1692. An annular sealing member 1694 on an outer wall of cell chamber 1682 forms a seal with an inner wall of housing section 1692. A buffer flush solution such as HBSS can be introduced through inlet port 1684 of cell chamber 1682 to remove the hibernation or transport buffer solution by moving. Waste flows out of device 1680 via an effluent port 1695 of housing 1692. A one-way check valve 1696 can be placed in fluid connection with effluent port 1695. Device 1680 can also be used as the administration syringe for delivery of cells by, for example, inserting a needle (not shown in FIG. 11F) into fluid connection with cell chamber 1682 (for example, through septum 1688, through filter 1690 or through another port). A needle can also be placed in fluid connection with effluent port 1695 of housing 1692. Filter 1690 can be moved to the back of chamber 1682 to facilitate use of device 1680 as a hand syringe by attaching a needle to the front of device 1680. Device 1680 is relatively simple to use regardless of the skill set of the operator.

Figure 11G:
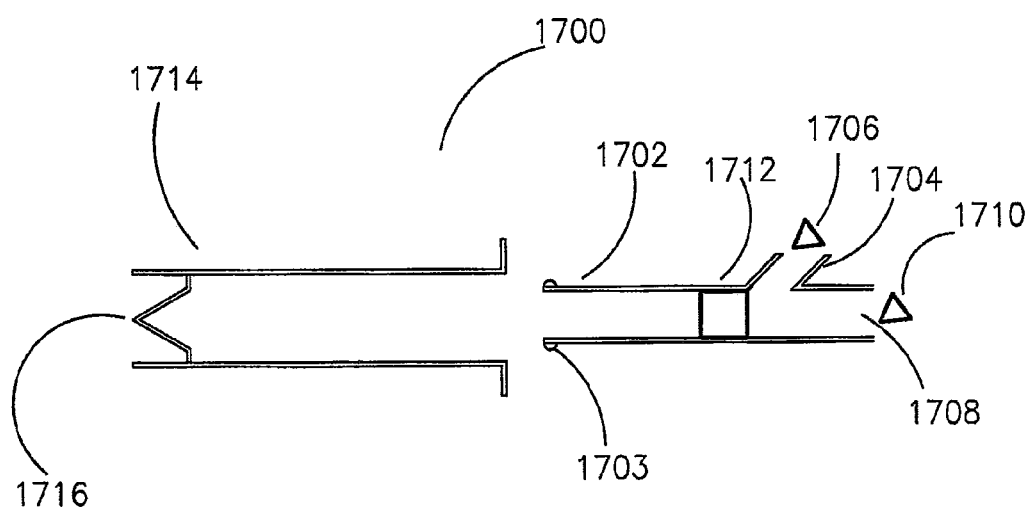
FIG. 11G illustrates another embodiment of a device of the present invention adapted to effect cell washing and/or buffer replacement and cell injection wherein buffer is being drawn into the device.
Figure 11H:
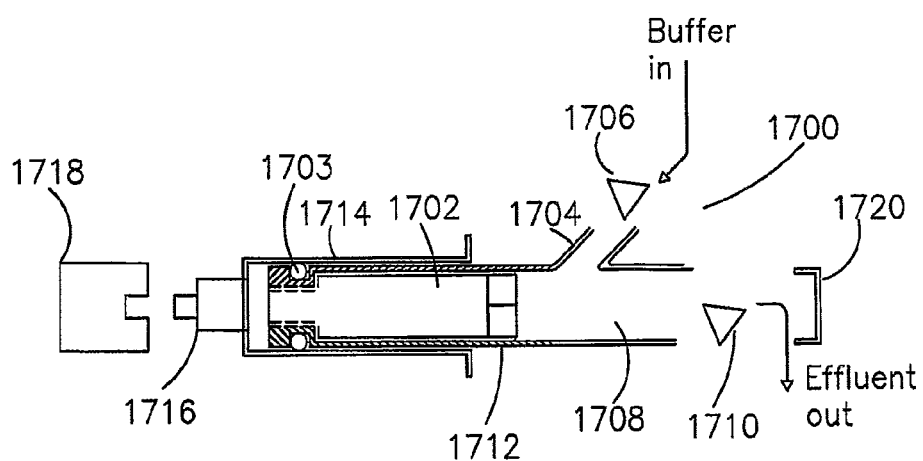
FIG. 11H illustrates the device of FIG. 11G in which the cell chamber is in operative connection with the housing or cylinder.

FIGS. 11G and 11H illustrate other embodiments of devices including a cell chamber or transport vial that includes a mechanism or fluid path to flush buffer solution (for example, HBSS) through the chamber while retaining the cells in the chamber. These embodiments are somewhat similar in operation to those of FIGS. 11C through 11F. In the system 1700 illustrated in FIGS. 11G and 11H, a cell chamber 1702 includes an inlet port 1704 through which a flushing buffer can be introduced into cell chamber 1702. A one-way check valve 1706 can be placed in fluid connection with inlet port 1704. Cell chamber 1702 also includes an effluent port 1708. A one way check valve 1710 can be placed in fluid connection with effluent port 1708. As compared to the embodiment of FIG. 11F, by moving the flow into and out of cell chamber 1702 (via inlet port 1704 and effluent port 1710 during, for example, repeated reciprocation of plunger cell chamber 1702 relative to housing 1714) to the same side of a filter 1712 (with the cells isolated on the other side of filter 1712) packing of cells on filter 1712 is prevented. In that regard, filter 1712 is washed of cells each time buffer solution is introduced. A sealing member 1703 can be placed in connection with an outer wall of cell chamber 1702 to form a seal with an inner wall of housing 1714.

In the embodiments of FIGS. 11G and 11H, a needle or other delivery device is attachable to, for example, a connector 1716 (for example, a luer type connector or other connector as described herein) on the end of housing 1714 (for example, a graduated cylindrical housing) without the requirement of puncturing a septum.

In FIG. 11H, plunger/cell chamber 1702 is positioned within housing 1714. A cap 1718 is provided for use in connection with connector 1716. Further, cap 1720 is provided for use in connection with effluent port 1708 during an injection using device 1700.

With cap 1718 in closing connection with connector 1716 and cap 1720 not in connection with effluent port 1710, rearward movement of plunger/cell chamber 1702 relative to housing 1714 (that is, movement of plunger to the right in the orientation of FIG. 11H), results in drawing fluid through inlet port into device 1700. Forward movement of plunger/cell chamber 1702 relative to housing 1714 results in effluent exiting effluent port 1710. Repeated reciprocation of plunger/cell chamber 1702 results is fluid treatment (for example, washing and/or buffer replacement) of the material (for example, cells) within device 1700. To inject using device 1700, cap 1720 is place in closing connection with effluent port 1710 and cap 1718 is removed from connection with connector 1716. A needle can, for example, be placed in fluid connection with connector 1716.

Device 1700 can be used to process any type of solution have solids suspended therein. Filter 1712 is used to separate such solids via size exclusion.

Figure 11I:
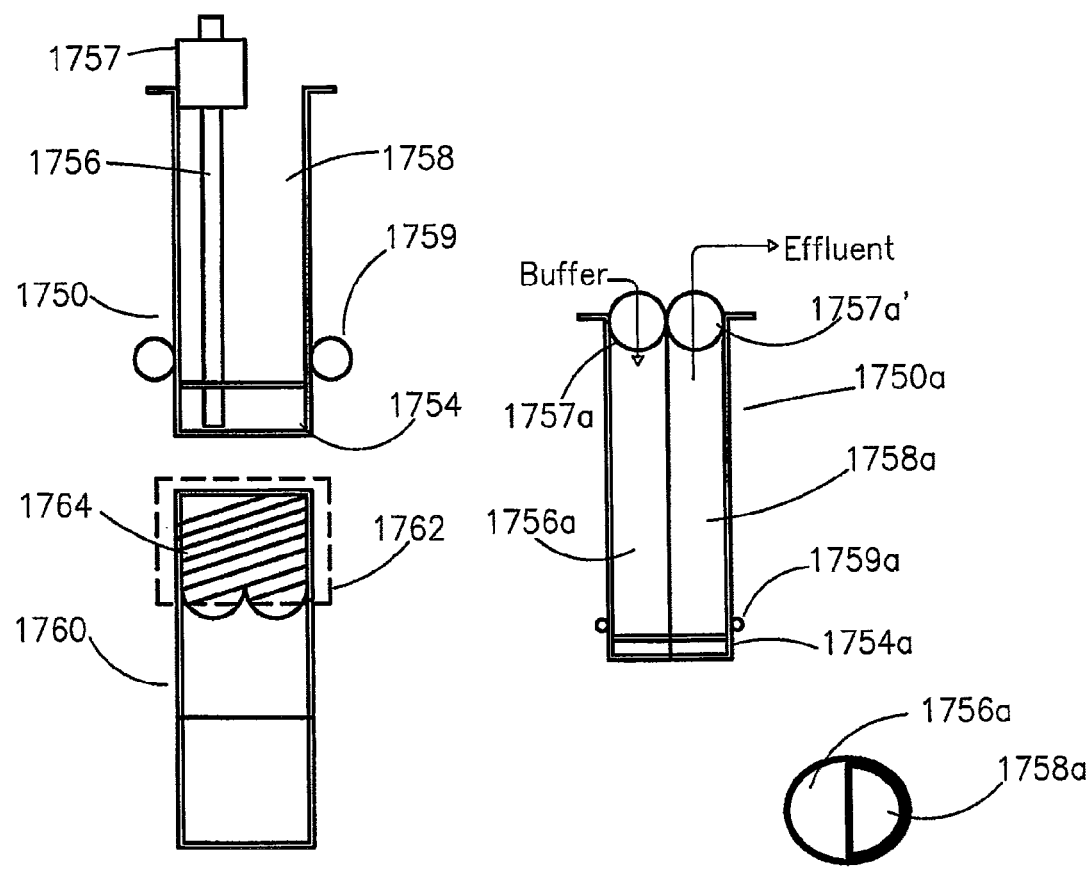
FIG. 11I illustrates embodiment of a plunger system operable to effect washing or buffer replacement in a standard vial such as a cryovial.

Moreover, as illustrated in the embodiment of FIG. 11I, a plunger 1750 can be used in connection with a conventional cryovial or other container 1760 to effect fluid treatment (for example, washing and/or buffer replacement) within a standard or convention cryovial or other container 1760. In general, plunger 1750 includes a filter 1754 on the distal end thereof to prevent cells (and/or other material in vial 1760) from entering either of two fluid pathways within plunger 1750. Fluid, which can pass through filter 1754, can enter vial 1760 through the first pathway and can exit vial 1760 through the second pathway formed through plunger 1750. One way check valves as described above can be used in connection with the first and second fluid pathways. A vial cap 1762 is first removed from vial 1760 (via, for example, threading 1764) as known in the art. Plunger 1750 is then placed within vial 1760.

In the embodiment illustrated on the left side of FIG. 11I, the first fluid pathway (which can, for example, be in fluid connection with a buffer solution) is a conduit 1756. A first check valve 1757 can be placed in fluid connection with conduit 1756 so that fluid can flow into vial 1760 through conduit 1756 but cannot exit via conduit 1756. The volume around conduit 1756 within plunger 1750 provides a second fluid flow pathway 1758 for effluent fluid to exit through plunger 1750 to waste. A second check valve (not shown) can be placed in fluid connection with second fluid flow pathway 1758. A sealing member 1759 (for example, an elastomeric, O-ring) is provided on plunger 1750 to form a seal with an inner wall of vial 1760. Upward (in the orientation of FIG. 11I) motion of plunger 1750 relative to vial 1760 results in drawing of fluid into the system. Downward motion of plunger 1750 results in forcing effluent out of the system.

In the embodiment of plunger 1750a on the right side of FIG. 11I, first fluid pathway 1756a and second fluid flow pathway 1758a are created by a divider 1753a in plunger 1750a. A first check valve 1757a is placed in fluid connection with first pathway 1756a and a second check valve 1757a' is placed in fluid connection with second pathway 1756a. Other like elements are numbered similarly to the numbering of corresponding elements of plunger 1750.

Figure 12:
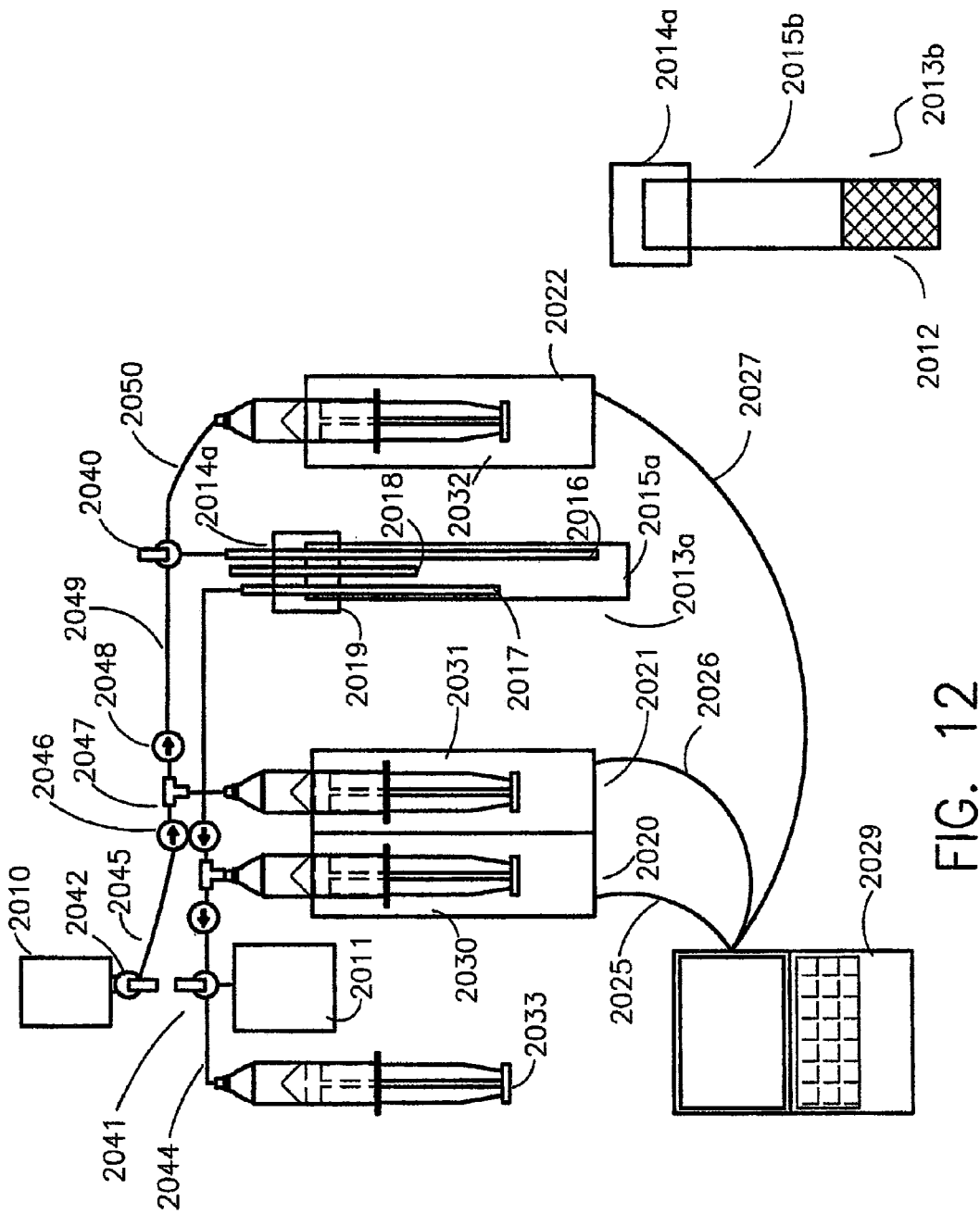
FIG. 12 illustrates a cell washing and/or buffer replacement system of the present invention that can effect multiple dilutions and gravity sedimentation to, for example, remove transport or hibernation solution/medium from the cells prior to injection.
Figure 13A:
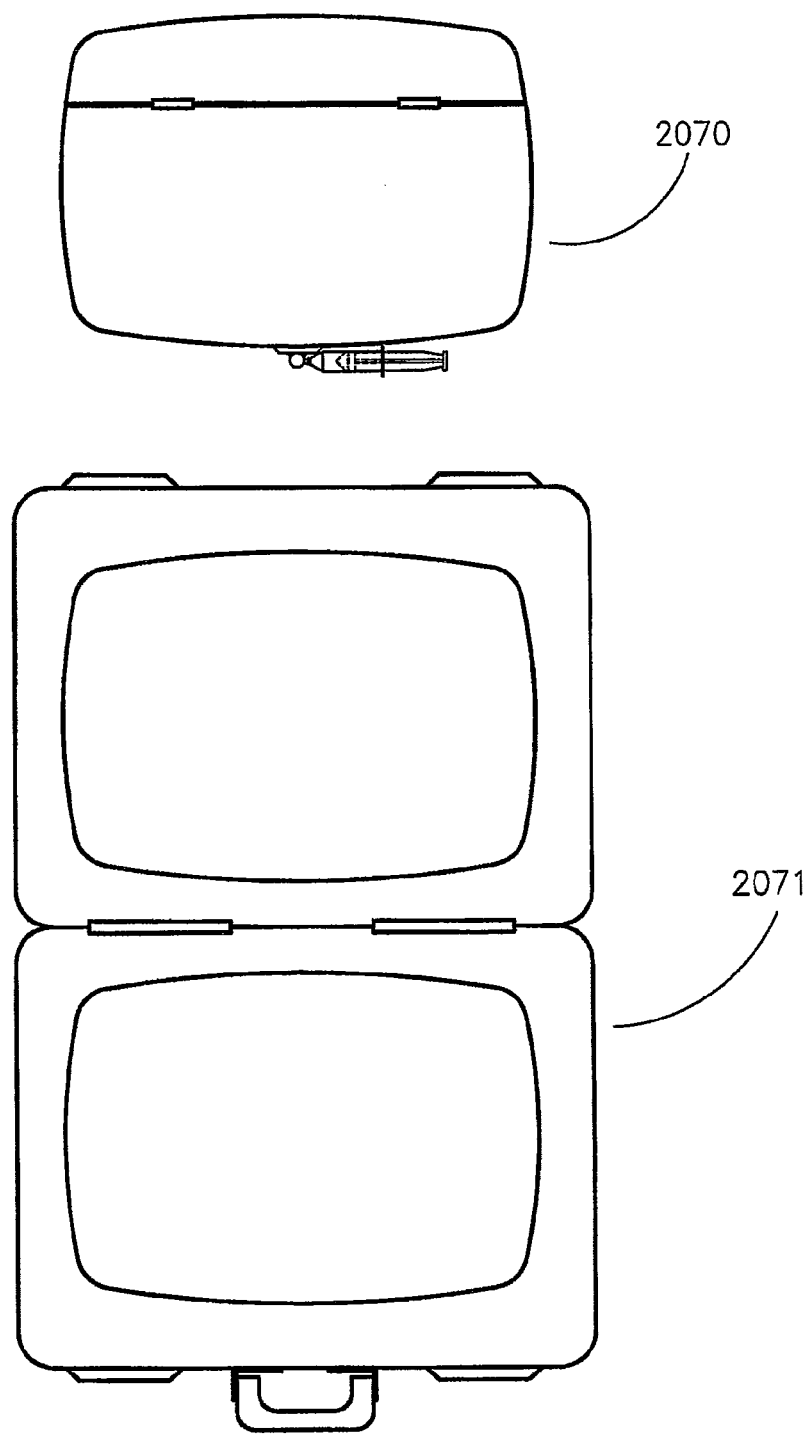
FIG. 13A illustrates an embodiment of an integrated transport, wash, buffer replacement and delivery system of the present invention.
Figure 13B:
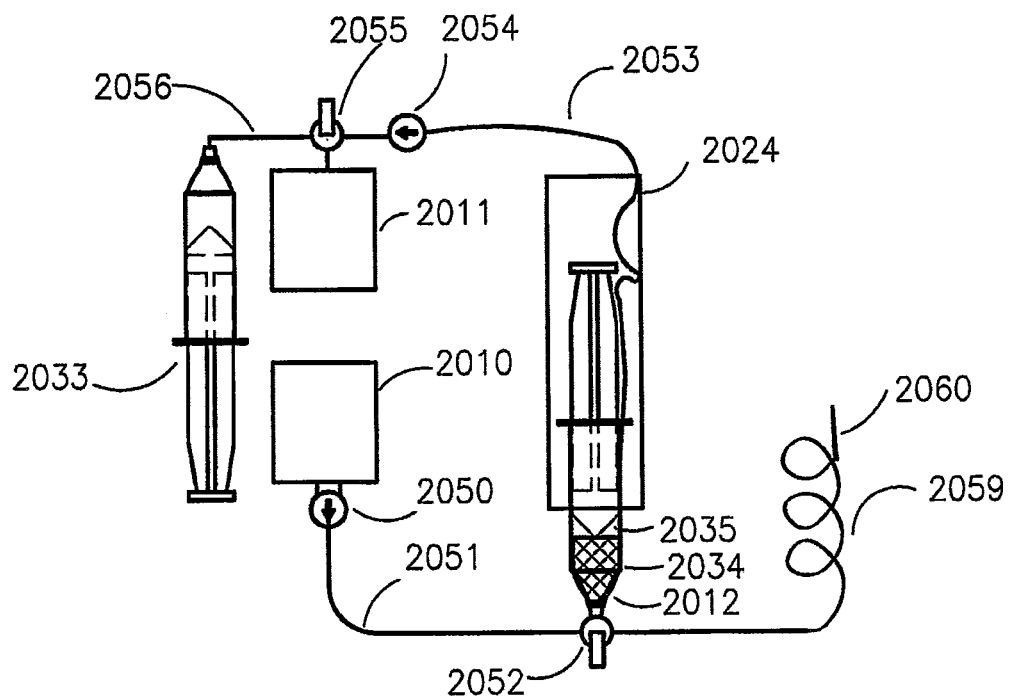
FIG. 13B illustrates several details of the flow path of the system of the FIG. 13B.
Figure 13C:
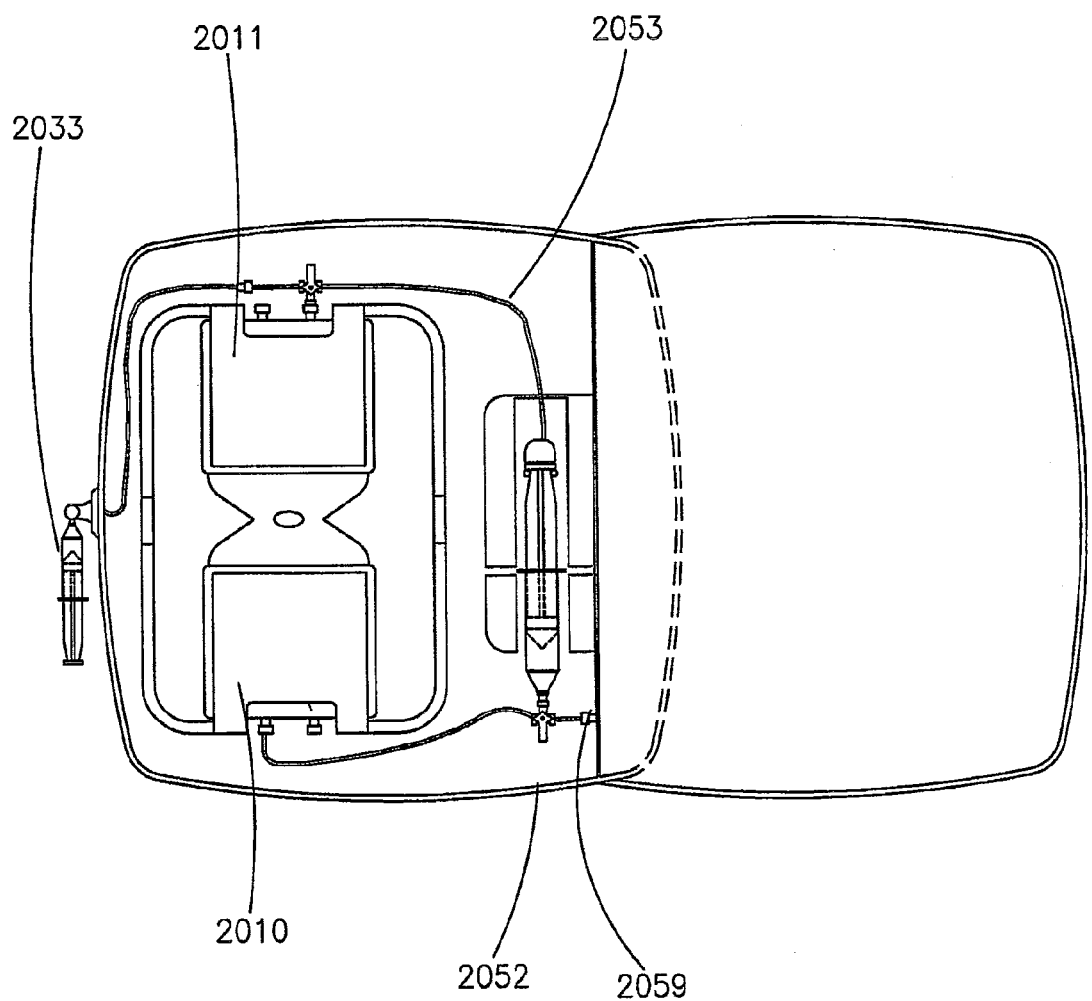
FIG. 13C illustrates position of the system of FIG. 13A so that a syringe thereof is vertical to allow settling.
Figure 13D:
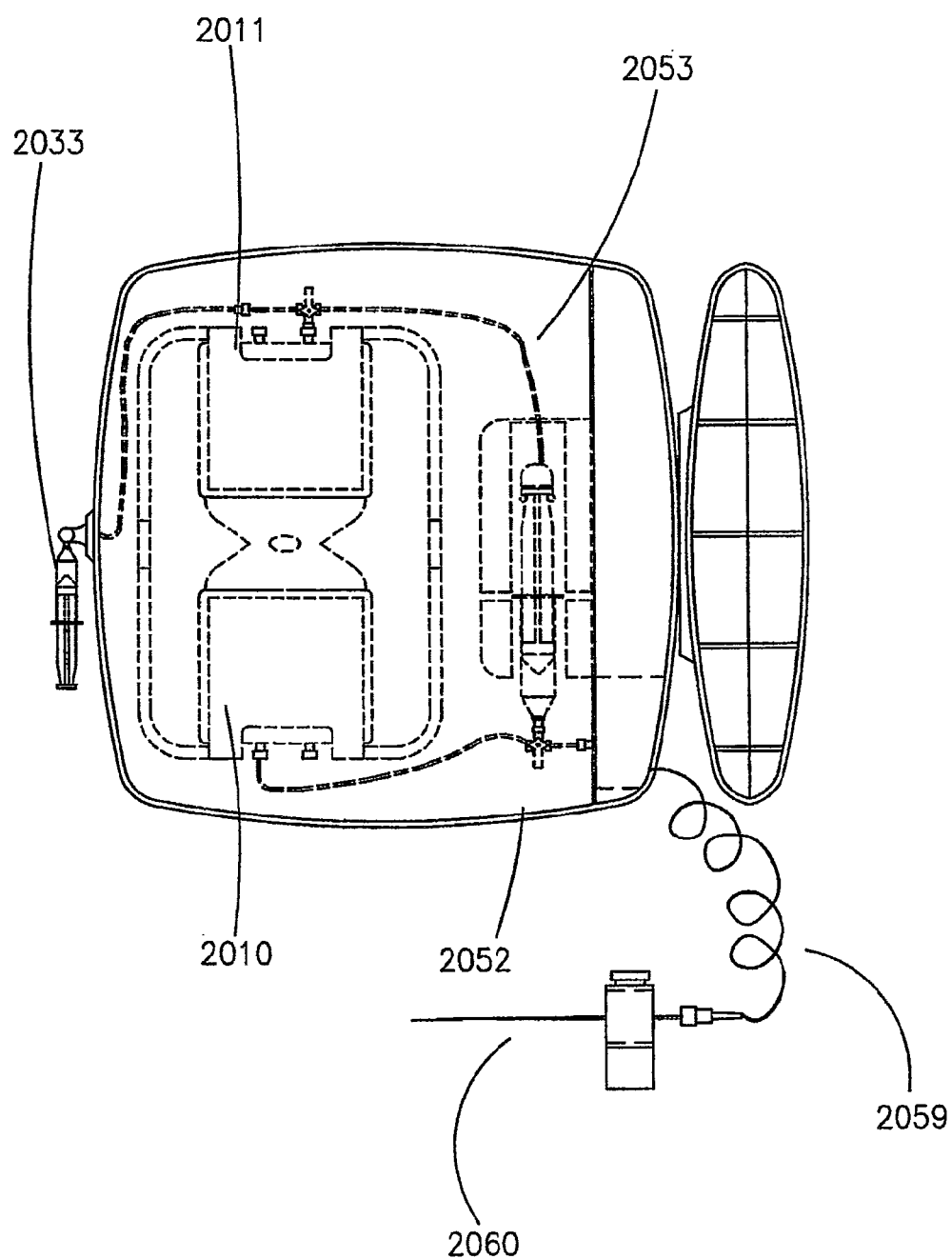
FIG. 13D illustrates the system of FIG. 13A positioned so that cells remain at a neck or outflow of the syringe for delivery.

Further embodiments of cell processing and/or delivery systems of the present invention are illustrated in FIGS. 12 through 13D. The cell wash system of FIG. 12 washes the cells using multiple dilutions and gravity sedimentation to remove transport or hibernation solution/medium from the cells so that they can be injected. The separation time can be reduced by employing centrifuging, as is known to those skilled in the art, at the expense of greater forces on the cells. The illustrated embodiment uses gravity.

The fluid path is closed and presterilized so that there is minimal chance of contamination of the cells. In addition, the closed system allows the preparation of the cells to take place in, for example, a cath lab, a neurosurgery suite, or any other place, preferably near the delivery procedure, without the need for a sterile hood.

With reference to the fluid path schematic illustrated in FIG. 12, there are three main fluid containers: a wash solution container 2010, here shown for example as an unvented collapsible bag, a cell container 2013, here shown as for example a 5 ml cryovial, and a waste container 2011, also shown for example as a collapsible bag, either unvented or vented. There are various fluid path elements connecting these containers. There are three pumps, shown here for example as syringe pumps, 2020, 2021, and 2022. The syringes and fluid path should be formed of materials that are compatible with the cells, for example polypropylene, polyethylene, and Teflon are suitable. In some situation it is desirable to have no silicon lubricant. Suitable syringes are manufactured for example by Henke Sass Wolf GMBH (HSW) of Tuttlingen, Germany. The wash solution container comes prefilled with the preferred wash solution for the specific cells, for example normal saline, Hanks Balanced Salt Solution (HBSS), or any other suitable liquid. The remainder of the fluid path can also be filled with wash solution, or it may be filled with air. If any of the fluid path elements contain air, then it will be necessary to fill them with liquid before starting the wash operation. (Note that it is normal and even desirable for some air to remain in the cell storage vial assembly 2013a). Connectors as described herein can be used to connect various fluid path elements.

The system of FIG. 12 includes a cap 2014a that is constructed to cooperate with the cell storage vial 2015a. The cap 2014a has three penetrations or passages passing therethrough. The first penetration has a tube 2016 that goes down to close proximity or touching the bottom of the vial 2015a. This is the inlet for the wash solution and it will be used at the end of the process to remove the washed cells as described above. The second penetration has a tube 2017 does not go as far down as the first tube 2016. Tube 2017 is used to remove the mixture of the wash solution and the contents of the vial. As described above, it does not go as deep as tube 2016 so that it does not draw cells therein when removing the mixed fluid. The position determines the amount of fluid containing cells that remains after the fluid has been removed. In this embodiment, it is approximately 1 ml. The third penetration is an air path 2018 with a sterile filter so that air can move in and out as the fluid level changes in vial assembly 2013a, without compromising sterility.

To wash cells, vial 2015a is removed from the system. The lid 2014b is removed from the vial assembly 2013b containing the cells, and vial 2015b is screwed onto lid 2014a. The system is only open to possible airborne contamination for the few seconds it takes the operator to make this switch. If need be, this could be done in a sterile hood, glove box, or bag. Moreover, the transport cryovial can include ports that cooperate with a cap of the present system to eliminate the need to open the vial. However, it is anticipated that the atmosphere of the surgical or special procedures suite will be sufficiently clean that this brief exposure entails an insignificant risk of contamination.

Once the cells are in place in the wash system, after sufficient time to allow for settling of the cells, for example 3-7 minutes, syringe pump 2020 is activated and the excess hibernation or transport solution is drawn from vial 2015b into syringe 2030 through a one way valve. When syringe 2030 is moved forward or upward, fluid is driven out the one way valve into waste bag 2011 or sampling syringe 2033, depending upon position of stopcock 2041. The sampling syringe can be used to sample the fluid that was just withdrawn to check for bacterial contamination of the cells, to verify that the wash is proceeding satisfactorily, or that it has been sufficient.

To avoid bubbles in the fluid path, it is preferable that the fluid level in vial 2015b never get so low that tube 2017 draws in air. A sensor, not shown, could be incorporated to measure fluid level in vial 2015b. However, if air is drawn through tube 2017, is not a significant problem because the bubbles will simply move into the waste container 2011 or sampling syringe 2033. In an alternative embodiment, one simply does this every time, pull out excess fluid so that air is pulled into tube 2017, to ensure that the fluid level returns to a known position without any need for sensors.

To deliver wash solution from container 2010 to vial 2015b, an optional stopcock 2042 (or other valve) is rotated so that fluid can be pulled from the wash solution container 2010. Stopcock 2040 is rotated into position so that fluid path 2050 is disconnected and fluid can flow from 2049 to 2016. Wash solution is pulled from the wash solution container 2010 through one way valve 2046 by pump 2021 pulling down on the syringe 2031 plunger. After pulling in sufficient fluid for the wash, syringe pump 2021 pushes the plunger upward and fluid flows out one way valve 2048, through fluid path 2049 and down tube 2016. As the fluid exits the tube 2016, it creates a gentle stirring of the cells 2012 such that the fluid around them is mixed with the wash solution, but not so turbulent a motion that a significant number of cells are damaged. The outlet of tube 2016 can, for example, be cut at an angle so that a swirling action is achieved. The flow rates will depend upon the toughness or fragility of the cells and the geometry of the vial 2015b and tubes, and can be adjusted by those skilled in the art, based upon cell viability tests to minimize cell damage and analysis of extracted wastes to ensure that there is sufficient agitation and mixing.

Once sufficient wash fluid has been mixed into vial 2015b, the cells are allowed to settle. Times on the order of minutes are commonly necessary, although if the cells are attached to relatively heavy substrates or magnetic substrates, this time can be significantly reduced. As mentioned above, centrifuging can increase the separation speed. It is also possible to employ a filter (not shown) at the tip of tube 2017 or all the way across the area of the vial 2015b at or below the level of the lower end of 2017 so that the cells are constrained to stay in the bottom of the vial 2015b. (In this case, there would have to be a penetration, not shown, to allow tube 2106 to reach the bottom of vial 2015b through the filter.).

As discussed above, after sufficient time, syringe pump 2020 is activated and the mixed solution, now termed waste is drawn from vial 2015b into syringe 2030 through the one way valve. When syringe 2030 is moved forward or upward, fluid is driven out the one way valve into waste bag 2011 or sampling syringe 2033, depending upon position of stopcock 2041 as discussed above.

A second wash cycle can be performed by repeating the steps of injection of wash fluid and withdrawal of mixed fluid as discussed above. Each time the wash cycle is completed, assuming complete mixing of the contents of the vial with the wash solution, the transport buffer is diluted by a specific fraction. If the volume remaining after waste withdrawal is 1 ml and the volume of wash solution injected is 2 ml, then each wash cycle leaves only 0.33 of the initial transport buffer in the vial. After 3 cycles, the was buffer has been reduced to 4%, after 6 cycles to 0.13%, and after 10 cycles it is down to 15 parts per million.

When the predetermined sequence of washes is completed, for example after a fixed number of washes or when the contents of the sampling syringe 2033 show that the wash has been sufficient, then the cells are ready to be transferred to the delivery syringe 2032. To do this, stopcock 2040 is rotated so that fluid path 2050 is connected to tube 2016. As mentioned above, there is no air in the fluid paths, and preferable syringe 2030 is as empty as possible, meaning that the plunger is all the way up in this diagram or forward in the syringe. To fill delivery syringe 2032, the plunger is quickly pulled down by pump 2022. This sucks cells and fluid out of the bottom of vial 2015b where the cells had settled through tube 2016. To maximize the transfer of cells, it is best to have the volume fluid of tube 2016, stopcock 2040, and tube 2050 be as low or small as possible in comparison to the volume of the delivery syringe 2032.

The sequence of wash steps can be controlled by some type of central computer 2029 or sequencer, for instance a laptop computer operating under Lab View by National Instruments. The pumps can be independent pumps which are controlled by the central computer is some sort of distributed system. Or, the pumps can be part of a single, fully integrated system, or the system can have some integration and some distributed network properties. The stopcocks could be automated and controlled by the system. Similarly, the stopcocks and one way valves could be replaced by pinch valves that are controlled by the system. This could reduce disposable parts costs. It is also possible to replace the syringe pumps 2021 and 2022 with other pumps, for example peristaltic pumps. Peristaltic pumps have the advantage that the one way valves can be eliminated. If a dual head, bi-direction peristaltic pump with slip clutches in the opposite directions were employed, rotating the pump one direction, for example clockwise, would engage the wash fluid pump to push fluid into the vial while not moving the waste fluid pump. Then rotating the pump in the counter clockwise direction would engage the waste fluid pump to pump out the waste fluid but not engage or rotate the wash fluid pump. Another alternative is to have a single pump in place of 2020 and 2021 and use an additional stopcock (not shown) or pinch valves to alternatively move wash fluid and waste fluid. This simplification is possible because there is no need to move both wash and waste fluids at the same time. If a filter is used as mentioned above, then it can be advantageous to push in wash solution such that it overlaps with withdrawal of some waste solution.

A further advantage of the system of FIG. 12 is that it can be operated fully manually. This is useful in case there is a failure of the pumping system, to save the cost of the pumping system, or for simple procedures where the cell washing does not require an automated system. It provides the benefits of reduced contamination to a manual process that would have otherwise required the use of a sterile hood or glove box.

FIG. 13A illustrates an embodiment of an integrated transport, wash, and delivery system of the present invention. The outer case 2071 contains thermal management systems such as insulation and ice or active cooling such as a Peltier cooling system and a power source (for example, one or more batteries). The benefit of active cooling is better control of temperature. The transport case 2071 optionally contains one or more sensors for shock, vibration, temperature, gas or other phenomena that could adversely affect the cells, so that if any adverse event occurs, these occurrence(s) are known before the cells are processed or given to a patient.

The wash and delivery subsystem 2070 is sterile on the inside and the outside, and is contained in a bag (not shown for clarity) to preserve the sterility. In the delivery room, operating room, special procedures laboratory or wherever the cell delivery is to take place, the wash and delivery subsystem is removed from the sterile bag and placed in the sterile field.

The wash and delivery subsystem 2070 is positioned so that the syringe is vertical and sufficient time is allowed to for the cells to settle as shown in FIG. 13C. The details of the fluid path are, for example, illustrated in FIG. 13B. The cells are contained in syringe 2034, sealed in by stopcocks 2052 and 2055. There is an optional filter at plunger 2035 to prevent cells from setting in fluid path element 2053. Container 2010 contains the wash solution and fluid path elements 2050 and 2051 are filled with fluid. To perform a wash cycle, stopcock 2052 is turned to connect syringe 2034 to fluid path 2051. Then stopcock 2055 is turned to connect fluid path 2053 to either waste container 2011 or sampling syringe 2033. The syringe pump 2024 pushes down on plunger 2035 and fluid is expelled through one way valve 2054 to the preselected waste container 2011 or sampling syringe 2033. The plunger 2035 moves down until sufficient liquid is removed, and stopped before a significant number of cells are removed.

Then syringe plunger 2035 is pulled upward, and wash solution is pulled from container 2010, through one way valve 2050 and into the neck of the syringe. This inflowing fluid stream will stir and agitate the cells in the syringe. An asymmetry of flow at the inlet to the syringe may be desirable to improve the mixing. This could be as simple as having the neck of the syringe come in off center or at an angle to the vertical to induce a net rotational force.

Then after sufficient time for the cells to settle, the plunger 2035 is moved down and the waste mixture is expelled.

This sequence of pulling fluid in from the bottom and expelling it from the top can be repeated to wash the cells as many times as desired. By having a sealed wash and delivery subsystem 2070, the fluids in the case will stay cooler longer, increasing the cell lifetime and reducing the pressure to rush the procedure. Additional thermal mass or a phase change material can be incorporated to increase the length of time over which the cells remain cold.

When the washing is completed, the cells can be delivered without the need to make any new connections.

To deliver the cells, for example here through a tubing 2059 and a needle 2060, the wash cycle is stopped, preferably with a little solution remaining above the cells, so that all the cells can be effectively delivered and not trapped in the volume of the syringe neck, tubing 2059, or needle 2060. Then stopcock 2055 is closed and stopcock 2052 is adjusted so that syringe 2034 is connected to fluid path 2059. Next, sufficient fluid is delivered to fill fluid path element 2059 and needle 2060. A sample can be taken by injecting cells out needle 2060 to verify cell viability, type, the lack of contamination, or other important properties or characteristic. This also ensures that the fluid path is filled with cells.

To deliver the cells, the needle is placed in the tissue and the syringe pump, either under direct operator control or as part of a delivery system, delivers the selected volume(s) at the selected flow rate(s) at the selected time(s).

The unit can be place in the sterile field, close the area of use. The unit can be hung vertically so that cells remain at the neck or outflow of the syringe. As illustrated in FIG. 13D, the needle holder that can be closed to improve the contamination prevention for the needle. The needle is held tip up to minimize any leakage of the cells. However, this may cause some cells to settle away from the tip of the needle. To avoid this, the needle may be stored horizontally, preferably along the bottom of the subsystem 2070, which is not shown in this figure.

When the procedure is complete, the unit can placed back in its bag, back into outer case and returned to the manufacturer. This procedure can, for example, enable after-the-fact verification that the cells were not contaminated during the procedure and allow for reuse and resterilization of the more expensive parts of the system.

As described above, pre-delivery processing of cells and transport of cell to a delivery system from a processing system (if necessary) is preferably via a closed or substantially closed system. In that regard, exposure of the cells to a non-sterile environment (for example, by opening a cryovial in non-sterile air) is preferably minimized in both the number of occurrences and in the length of time. Moreover, in case that the cells are exposed to, for example, non-sterile air, the occurrences are limited to, for example, one or two occurrences and the amount of time of each such occurrence in merely the amount of time required for an operator to make one or more fluid connections. Further, the systems and devices of the present invention can, for example, be used in a cath lab or neurosurgery suite in which it is anticipated that the environmental air will be quite clean.

While the embodiments of this invention have generally been described with respect to the therapeutic delivery or injection of live cells, it will be apparent to those skilled in the art that this application of this invention can provide the benefits described herein to other fluid delivery situations, for example in the medical field including viral delivery, large molecule delivery, and drug delivery, and fluid delivery needs outside medical treatment arena, including cell, viral, or molecular delivery in laboratory or industrial applications.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A container adapted to store and transport an injectate, the container comprising:
    an open top end, a closed bottom end, and a central axis extending between the open top end and the closed bottom end;
    an inlet port at a first axial position within the container;
    a first piercing member having a distal end and extending through an end closure of the container enclosing the open top end, the first piercing member extending toward the closed bottom end of the container;
    at least an outlet port at a second axial position within the container, the first axial position and the second axial position being different;
    a second piercing member having a distal end extending through the end closure of the container toward the closed bottom end of the container; and
    a divider disposed within the container, the divider extending from the open top end toward the closed bottom end and spaced apart from the closed bottom end and defining an opening, the divider separating the container into a first fluid path on a first side of the divider through which fluid can enter the container through the inlet port and a second fluid path on a second side of the divider through which fluid can enter the opening and exit the container through the outlet port, the second fluid path including at least one filter between the opening and the open top end through which fluid can pass from the first fluid path to the second fluid path but through which at least one component of the injectate cannot pass, wherein the inlet port is disposed on the distal end of the first piercing member and the outlet port is disposed on the distal end of the second piercing member; and wherein, in use, the container encompasses viable cells within a first fluid and at least one of the first axial position and the second axial position is above an axial position of cells settled on or adjacent to the closed bottom end of the container.

2. The container of claim 1, wherein the cells are retinal pigment epithelial cells supported on microspheres, mesenchymal stem cells, multipotent adult progenitor cells, embryonic stem cells, cardiac precursor cells, cardiac cells, beta-islet precursor cells, beta-islet cells, neural precursor cells, or neural cells.

3. The container of claim 1, wherein the container encompasses the viable cells within the first fluid and the at least one filter prevents the viable cells from passing therethrough.

4. The container of claim 1, wherein the container is adapted to be subjected to freezing and thawing.

5. The container of claim 1, wherein an interior surface of the closed bottom end of the container is rounded.

6. The container of claim 1, wherein the inlet port is configured for filling the container with buffer solutions, washing solutions or other medical or therapeutical solutions.

7. The container of claim 1, wherein the outlet port is configured for removing an effluent from the container.

8. The container of claim 1, wherein the inlet port operates as an outlet port for removing the viable cells for injection to a patient.

9. The container of claim 1, wherein the container is part of a system, the system containing at least a first syringe and a second syringe, wherein the first syringe and the second syringe are connected to the inlet port and outlet port respectively.

10. The container of claim 1, wherein the outlet port operates as an inlet port for a flushing fluid for flushing the viable cells out of the at least one filter.

11. A container adapted to store and transport an injectate, the container comprising:

an open top end, a closed bottom end, and a central axis extending between the open top end and the closed bottom end;

an inlet port at a first axial position within the container;

a first tubing having a distal end and extending through an end closure of the container enclosing the open top end, the first tubing extending toward the closed bottom end of the container;

at least an outlet port at a second axial position within the container, the first axial position and the second axial position being different;

a second tubing having a distal end extending through the end closure of the container toward the closed bottom end of the container, wherein the inlet port is disposed on the distal end of the first tubing and the outlet port is disposed on the distal end of the second tubing; and a divider disposed within the container, the divider extending from the open top end toward the closed bottom end and spaced apart from the closed bottom end and defining an opening, the divider separating the container into a first fluid path on a first side of the divider through which fluid can enter the container through the inlet port and a second fluid path on a second side of the divider through which fluid can enter the opening and exit the container through the outlet port, the second fluid path including at least one filter through which fluid can pass from the first fluid path to the second fluid path but through which at least one component of the injectate cannot pass, wherein, in use, the container encompasses viable cells within a first fluid and at least one of the first axial position and the second axial position is above an axial position of cells settled on or adjacent to the closed bottom end of the container.

12. The container of claim 11, wherein at least one of the tubing comprises a spike and at least one of the cap and the end closure is a piercable septum.

13. The container of claim 11, wherein the cells are retinal pigment epithelial cells supported on microspheres, mesenchymal stem cells, multipotent adult progenitor cells, embryonic stem cells, cardiac precursor cells, cardiac cells, beta-islet precursor cells, beta-islet cells, neural precursor cells, or neural cells.

14. The container of claim 11, wherein the container encompasses the viable cells within the first fluid and the at least one filter prevents the viable cells from passing therethrough.

15. The container of claim 11, wherein an interior surface of the closed bottom end of the container is rounded.

16. The container of claim 11, wherein the inlet port is configured for filling the container with buffer solutions, washing solutions or other medical or therapeutical solutions.

17. The container of claim 11, wherein the outlet port is configured for removing effluent from the container.

18. The container of claim 11, wherein the inlet port is configured for removing the viable cells for injection to a patient.

19. The container of claim 11, wherein the container is part of a system, the system containing at least a first syringe and a second syringe, wherein the first syringe and the second syringe are connected to the inlet port and outlet port respectively.

20. The container of claim 11, wherein the outlet port operates as an inlet port for a flushing fluid for flushing the viable cells out of the at least one filter.

* * * * *

UNITED STATES PATENT AND TRADEMARK OFFICE
CERTIFICATE OF CORRECTION

| | |
|---|---|
| PATENT NO. | : 9,629,780 B2 |
| APPLICATION NO. | : 13/845713 |
| DATED | : April 25, 2017 |
| INVENTOR(S) | : Uber et al. |

It is certified that error appears in the above-identified patent and that said Letters Patent is hereby corrected as shown below:

On the Title Page

On Page 3, in Item (56), under "OTHER PUBLICATIONS", in Column 1, Lines 1-2, delete "Endocardioal Solutions Website (www.endocardioalsolutions.com/patient/index.html)" and insert -- Endocardial Solutions Website (www.endocardialsolutions.com/patient/index.html) --, therefor.

In the Specification

In Column 2, Line 53, delete "class 100" and insert -- class --, therefor.
In Column 5, Line 16, delete "measure" and insert -- measured --, therefor.
In Column 5, Lines 35-36, delete "sensor being can be connection" and insert -- sensor can be in connection --, therefor.
In Column 7, Line 65, delete "can adapted" and insert -- can be adapted --, therefor.
In Column 9, Line 33, delete "a normally closed, a push-button" and insert -- a normally closed push-button --, therefor.
In Column 9, Line 39, delete "use needle" and insert -- use of the needle --, therefor.
In Column 9, Line 40, delete "needle" and insert -- needle is placed --, therefor.
In Column 13, Line 14, delete "microprocessors 200," and insert -- microprocessors 210, --, therefor.
In Column 15, Line 7, delete "431" and insert -- 431n --, therefor.
In Column 20, Line 17, delete "plunger/indicator 1034c" and insert -- plunger/indicator 1032c --, therefor.
In Column 20, Line 19, delete "plunger 1034c" and insert -- plunger 1032c --, therefor.
In Column 20, Line 28, delete "a normally closed, a push-button" and insert -- a normally closed push-button --, therefor.
In Column 21, Line 10, delete "defection" and insert -- deflection --, therefor.
In Column 23, Lines 50-51, delete "dimmeric" and insert -- dimeric --, therefor.
In Column 24, Line 5, delete "Sculpta," and insert -- Sculptra, --, therefor.
In Column 27, Line 41, delete "BD" and insert -- Bd --, therefor.
In Column 30, Line 16, delete "syringe 100"." and insert -- syringe 50". --, therefor.
In Column 33, Line 54, delete "infracted" and insert -- infarcted --, therefor.

Signed and Sealed this
Twenty-ninth Day of May, 2018

Andrei Iancu
*Director of the United States Patent and Trademark Office*

CERTIFICATE OF CORRECTION (continued)
U.S. Pat. No. 9,629,780 B2

In Column 38, Line 35, delete "CYROVIAL®." and insert -- CRYOVIAL®. --, therefor.
In Column 38, Line 38, delete "Plasiques" and insert -- Plastiques --, therefor.
In Column 41, Line 35, delete "Plunger chamber 1656" and insert -- Plunger chamber 1654 --, therefor.
In Column 45, Line 24, delete "syringe 2031 plunger." and insert -- syringe plunger 2031. --, therefor.
In Column 45, Line 50, delete "tube 2106" and insert -- tube 2016 --, therefor.
In Column 45, Line 67, delete "the was" and insert -- the --, therefor.
In Column 46, Line 18, delete "tube 2050" and insert -- tube 2017 --, therefor.